(12) United States Patent
Wang et al.

(10) Patent No.: US 9,642,370 B2
(45) Date of Patent: May 9, 2017

(54) BACTERIA AND METHOD FOR IMPROVING PLANT HEALTH AND GROWTH

(71) Applicant: University of Florida Research Foundation, Inc., Gainesville, FL (US)

(72) Inventors: Nian Wang, Auburndale, FL (US); Jinyun Li, Winter Haven, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/018,849

(22) Filed: Feb. 8, 2016

(65) Prior Publication Data

US 2016/0227789 A1 Aug. 11, 2016

Related U.S. Application Data

(60) Provisional application No. 62/113,048, filed on Feb. 6, 2015, provisional application No. 62/199,327, filed on Jul. 31, 2015.

(51) Int. Cl.

| | | |
|---|---|---|
| *A01N 63/00* | (2006.01) | |
| *A01N 63/02* | (2006.01) | |
| *C12N 1/20* | (2006.01) | |
| *C12R 1/01* | (2006.01) | |
| *C12R 1/11* | (2006.01) | |
| *C12R 1/125* | (2006.01) | |

(52) U.S. Cl.
CPC .............. *A01N 63/02* (2013.01); *C12N 1/20* (2013.01); *C12R 1/01* (2013.01); *C12R 1/11* (2013.01); *C12R 1/125* (2013.01)

(58) Field of Classification Search
None
See application file for complete search history.

(56) References Cited

U.S. PATENT DOCUMENTS

2015/0020239 A1* 1/2015 von Maltzahn ........ A01N 63/02 800/298

OTHER PUBLICATIONS

Hu et al., Crop Protection, Oct. 2013, vol. 52, p. 151-158.*

* cited by examiner

*Primary Examiner* — Kade Ariani
(74) *Attorney, Agent, or Firm* — Timothy H. Van Dyke; Beusse, Wolter, Sanks & Maire PLLC

(57) ABSTRACT

This application describes and claims a method of improving the health and vigor of a plant, comprising administering to the plant an effective amount of a bacterial composition which comprises a botanically compatible vehicle and an isolated bacterial strain selected from the group consisting of *Bacillus megaterium* PT6, *Bacillus subtilis* PT26A, *Paenibacillus* sp. ATY16, and any combination thereof. Improvement in health and vigor is one or more of the following: a) improved resistance to disease; b) improved ability to defend against disease; c) reduction of disease symptoms; d) faster growth; e) improved crop productivity; f) improved crop quality; g) improved seed germination; h) improved seedling emergence; or any combination thereof. Isolated bacterial strains and mixtures of bacteria are provided, as well as compositions comprising the isolated bacterial strains.

31 Claims, 13 Drawing Sheets

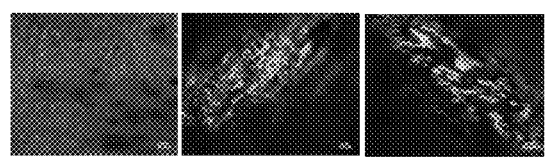
Fig. 4A
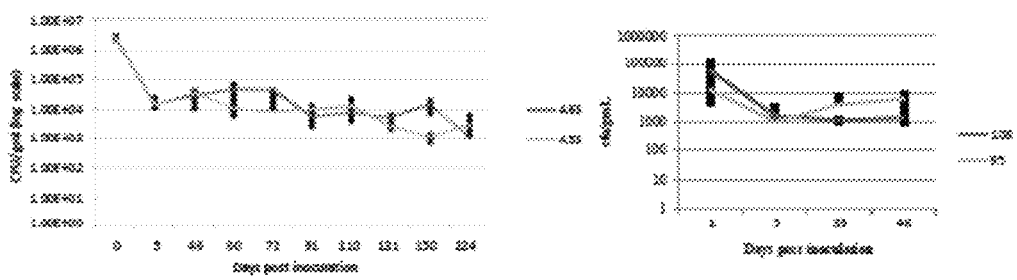
Fig. 4B
Fig. 4C

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agagtttgat cctggctcag                                              20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2

```
ggttaccttg ttacgactt                                                  19
```

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
cagcmgccgc ggtaatac                                                   18
```

<210> SEQ ID NO 4
<211> LENGTH: 2361
<212> TYPE: DNA
<213> ORGANISM: Paenibacillus sp.

<400> SEQUENCE: 4

```
atgtttaatc cgataaatat tgatcaagcc gtacagaagc tgaaccctcc tcagagggat      60
gccgttcaag cgacggatgg accattgctt atcatggcgg gagcgggctc cggcaagacc     120
cgcgtcctta ctcaccgtat tgcctattta atcgagaaga agcgggttgc cccttggagc     180
attctggcca ttaccttac gaataaagcg gccagggaga tgcaggcgag ggtggcggcg     240
cttattggcc cttccggtca ggatatttgg gtctctacct tccactccat gtgcgtacgg     300
attctccgca gggatatcga ccgcatcggc tttacctcca atttctcgat cctggattcc     360
gccgaccagc tgtcggtcat cgcaattgc atgaaagagc ttaatatcga cgtgaaaaag     420
tttgaaccga agccgttca ggctgaaatc agcggcgcga agaatgagct gattacgccg     480
gagcgttatg agcagaagat aggcgactat tttaccgata ttgtggcgaa agtatttaag     540
atgtaccaga agcggctgaa gagcaacaac tcgctggact ttgacgatct gatcatgacg     600
acgattcagc tgttcaagga aatgccggaa gtgcttgagt tctaccagaa caaattccgt     660
tatatccacg tggacgagta tcaggatacg aaccgcgcgc aatacatgct ttgccgcatg     720
ctggctgaca agcatcacaa tatttgcgtt gtcggcgaca cgaccagtc gatctaccgc     780 tggcgcggag cggacattac gaacatcctg aactttgagg atgactatcc ggaagcccgt     840
accattatgc tcgagcagaa ttaccgttct acggccaaca ttctggaagc ggccaatgcc     900
gtcatcaagc tgaacacggg ccgcaagccg aagaagctgt ggaccgacca aggagaaggc     960
gacatgatca ccttgtacca agccgactcc gagcatgatg aaggatattt cgtaaccggc    1020
acgatcagca aaacgtgaa aagcggccgc aggtacgatg accatgcgat tctgtaccgc    1080
accaacgccc agtcccgcgt aatcgaggaa atactgatca agtcggacat tccgtatcag    1140
attgtcggcg gcatcaagtt ctacgaccgc aaagagatta aggatttgct cgcttacctc    1200
agactgatct ccaatccgga cgacgatatc agcttcagc ggatcatcaa tgttccgaag    1260
cggggaatcg gcgatacgac ggtagcgaag ctggcggaag aagcagttcg tcaaggcacg    1320
tctatcttta acgtgcttgg caatctgcaa gggatagatc tgaacgcccg gcacagggc    1380 ctgctgcatg aattccggga tatgatcgat aatctaacgc agatggtcga ttatctgtcc    1440
gtaaccgagc tgacggagaa agtgttggaa atgtcgcaat accgcatgga gttgcagcgc    1500
gagaagacgc ttgagtcgac tgcccgcctc gagaacatcg acgagttcct gtccgttacg    1560
atggacttcg agaagcgcaa cgaagacaag acgttagtcg ctttcctgac ggatcttgcc    1620
cttatcgcgg atattgattc catggacaag gacgatgacg gaaaaccggc ggacaacaat    1680
```

-continued

| | |
|---|---|
| tccgttgttc tcatgacgat gcatagcgcg aaaggcctgg agttcccggt tgtctttatt | 1740 |
| atcgggatgg aggaaagcat cttcccgcac agccgtgcgt taaacgataa cgaagagctc | 1800 |
| gaagaagagc gccgccttgc ttacgtaggg attacccgcg cggagaagca gctttacctg | 1860 |
| acttgcgcgc gcagccggac tctcttcggc cgcatcagcg ccaacctgcc ttcgcgtttc | 1920 |
| ctgcaggaag tgccggacaa cgtgaagacg ctggcttcgc cgggcggtac gatcggccgc | 1980 |
| tccggcagct tgccggcgg cgcaagccgc gcaagcttcg gcagcagcgg tagcggagcc | 2040 |
| agctttggcg cagggcgcgc gccatccttt ggcgcttccg gcgccggagc ccgaaccccg | 2100 |
| ggaccatcgg gggcgggagt gcgcgtgagc acgccgcttg acgcggccgc gaaagcggcg | 2160 |
| tctaccgccg gatcggccgc ggggaatgcc gcggaccgga acttcgtagc cggcgacaag | 2220 |
| gttgcgcacg gcaaatgggg cgaaggcgtc atcgtttccg tcaaagggac gggcaacgat | 2280 |
| atggagctgc aaatcgcttt ccctgcgccg gttggcgtca aacggctttt ggccggattt | 2340 |
| gcaccaataa caaaagtcta a | 2361 |

<210> SEQ ID NO 5
<211> LENGTH: 2508
<212> TYPE: DNA
<213> ORGANISM: Paenibacillus sp.

<400> SEQUENCE: 5

| | |
|---|---|
| atgctcggac tagtgaaaaa aatattcggt gatgcgaacg agcgcgaggt caagcgtctc | 60 |
| acgcgtacgg tagaagaaat taacggactt gagtccaaga tatcgccgct gtcagacgat | 120 |
| gagctgcgta ataaaacgga agagttcaag ggacgtcttg aaaaaggcga ggatattgac | 180 |
| tcgattctgc cggaagcttt cgcggttgtg cgcgaagcat cgaagcgtac gcttggcatg | 240 |
| cgccatttcg acgtacagct gatgggtggt atggtgctgc acgaaggcaa gatcgcagag | 300 |
| atgagaaccg gtgaaggtaa aacgctcgtt gcgacgcttc ctacttatct gaatgcattg | 360 |
| caaggcaaag gcgtacacgt tattacggtc aatgattacc ttgcatctcg cgacagccag | 420 |
| atcatggctg aactttataa tttcctcgga ctgactgtcg gctgcaacct gcacggcttg | 480 |
| acgcatgaag agaagcaaga agcttatgcc tgcgatatta cttacggaac caataatgag | 540 |
| ttcggctttg actatttgcg cgataacatg gtgctgtaca agagcaaat ggttcaacgc | 600 |
| ccgctttatt atgcaatcat agacgaagtg gactccatcc tggtcgacga ggcgcgtacg | 660 |
| ccgctgatca tctccggaca agcacaaaaa tcgacggagc tgtattatgc cgctgaccgt | 720 |
| ttcgtcagcc gtttgaaaga ggaagaggat tacacggttg atattaagct tcgcaacgta | 780 |
| acgctgacgg aagccggcgt tgagaaagcg gagaaagcat tcggcatcga aacttattc | 840 |
| gatcatgcga acgtaacgct gaaccatcac gtgcaacaag cgcttaaagc gcatgtcatc | 900 |
| atgaagcgcg acgtggatta cgtggttaac gaagacgaag tcgtcatcgt cgacgaattc | 960 |
| acgggccgtc tgatggcggg ccgccgttac agcgacggtc tgcaccaagc gatcgaagcg | 1020 |
| aaggagcagc tgaaggttca gaacgagagc atgacgcttg cgacgattac gttccagaac | 1080 |
| tacttccgta tgtaccggaa gctgtcgggc atgaccggta cggcgaagac ggaggaagaa | 1140 |
| gagttcaaac ggatctacgg tctcgaggtt attcaaattc cgacaaaccg cgctctgatc | 1200 |
| cgtaaagata tgcaggacgt ggtctacaaa tccgagaatg gcaagtttaa agccgttgtt | 1260 |
| gaggaaatcg tagaacgtca caagaagaac cagccggtac tcgtgggtac aatctccatc | 1320 |
| gagaactcgg agcgtctgtc cgacatgctg aaaaagcgcg gcgtgcagca taaagtactg | 1380 |

```
aacgcgaagt tccatgcgga ggaagcggaa atcatctccc gcgcgggtca agcgggcgcg     1440
gttacgatcg cgacaaacat ggcgggacgc ggtacggaca ttttgctcgg cgaaggcgtt     1500
catgacgtag gcggtctgca cattatcggt acggagcgcc atgagagccg tcgtatcgat     1560
aaccagctgc gcggtcgtgc cggccgtcaa ggcgacccgg gctcctcgca gttctatctc     1620
tcccttgagg atgaactgat gcgccgcttt ggcgcggaga acattatggg catgatggac     1680
cgtctgggtc tggaagaaga ccagccgatc gagagccgcc tcattacgcg tgccgttgag     1740
tccgctcaga agcgcgtaga gggcagcaac ttcgataccc gtaaagtcgt cctgcaatat     1800
gacgatgtca tgaaccagca gcgggaagtg atttacaagc agcgccgtga cgtattgtac     1860
tcggagaaca tccgcgagat cgttatggaa atgatcatac cggttatcga gcatgtggtt     1920
gaagcccata cggaaggcga tattccggaa gagtgggatc tgcaggaaat cgcggattac     1980
gcgaactcga accttctccc tgaagatacg ttctcgaagg acgatctgtg gggcaaagag     2040
aaggaagata ttatcgagct tatcaaggat aaggttgttg cttattacga tgagcgcgag     2100
gctgagcttg gcgccgaaac gatgcgcgaa ttcgagaagg ttgtcgtact gcgcgcggta     2160
gacagcaaat ggatggatca catcgatgcg atggatcagc tccgccaagg tatccacctc     2220
cgtgcatacg gcgtacgga tccgcttcgc gagtaccaat tcgaaggctt cgagatgttt     2280
aaggaaatga tctacagcat ccaggaagaa gtcgcgaagt acatcatgaa ggcacgagtg     2340
gagagcaacc tggagcgtca agaggttgcg caaggccaga cgacgaccaa cagcccggcg     2400
gaagcggaaa acgccctgc gaagcgtgaa gagcgtacgg gacgcaacga cctttgccca     2460
tgcggcagcg gcaagaaata caaaatgtgc catggcatgg gcaagtaa                 2508
```

<210> SEQ ID NO 6
<211> LENGTH: 1146
<212> TYPE: DNA
<213> ORGANISM: Paenibacillus sp.

<400> SEQUENCE: 6

```
atgcaagcaa gattattgtt ggaagacgga acgttgttta ccggacaatc tttcggcgcg       60
gagacgcaaa cgttcggaga ggttgttttt aatacaggga ttacggggta ccaggaagta      120
ttgtccgatc catcctactg cggacaaatc gtatcgatga cttatccgct gattggcaac      180
tacggcattt cgcgcgatga cttcgagtcg atccgcccaa gcattcacgg gtttgttgta      240
cgccgttatg agccggtgcc aagcaactgg cgcgcgcaat attcgctcgg cgacctgctg      300
aaggaataca acattccggg catcacaggc atcgatacgc gcatgctgac tcgtattctg      360
cgtcagcacg gtacaatgaa aggcgttctg acaaccggca ccgaacgcgt ggaagagctt      420
caggaacgtc ttggcggcat tcagctgatg acggatcaag ttgcgcgcac atcgaccaaa      480
tcggtcttct cgagcccggg ctttggccct cgcatcgtgc ttgtcgactt cggagctaag      540
agcggtatcc ttcgcgagct gacgcagcgc ggctgcgacg ttgtggttgt tcctcataac      600
acaacggcgg acgagattcg caaattggct ccggacggca ttcagctgtc caacggcccct     660 ggggatccga agacgttcc ttatgcggtt caaatgatca agagctgct cggcgagatt      720 cctatcttcg gcatctgcct tggtcaccag ctgttcgctc tggcttgcgg cgcggatacg      780
acaagactta agttcggtca ccgcggcggc aaccatccgg ttaaagaact ggctaccggc      840
cgatgctacg ttacttcgca gaaccatggc tacacggttc tcgaagattc gatcaacagc      900
acggaactat ccgttacgca catcaataac aatgacaaga ccattgaagg tctgaaacat      960
aacaaatacc cggcattctc ggtgcaatac catccggaag ctgcgccagg cccgtttgat     1020
```

-continued

```
tccagctatc tgttcgatga attcctggac atgatccgcg accacaaaca aaacaacccg    1080
caaaaacctc gtcaagctgt gctggcggca acgttgaaag gagaacttca atatgcccaa    1140
aaataa                                                                1146
```

<210> SEQ ID NO 7
<211> LENGTH: 960
<212> TYPE: DNA
<213> ORGANISM: Paenibacillus sp.

<400> SEQUENCE: 7

```
atgcaagttg aaaccgtacc aagcggttca attgctttag atattgctct tggaatcggc      60
ggtatgccaa gaggccgtat tattgaatgc tacggaccgg aatcctccgg taaaacaacc     120
gttgcgcttc acgctattgc ggaagtacaa cggatcggcg acaagctgc atttatcgat      180 gcggagcatg cgcttgatcc attgtacgcg agcaagctgg gcgtaaatat cgacgaactg     240
ctgttgtcgc agccggatac gggtgaacag gcgcttgaga tcgcagaagc gcttgtacga     300
agcggcgcgg tcgacattat cgttatcgac tccgtagcag cacttgtacc gaaagcagag     360
attgaaggcg atatggggga ttcccatgtc ggtctgcagg cacgtctgat gtcgcaggct     420
ctgcgtaaat gggtggcgc gatcagcaag tcgaagacaa tcgccatctt tattaaccag      480
ttgcgcgaga aagtcggcgt tatgttcggt aacccggaaa ctacgcctgg cggccgcgca     540
ctgaagttct attccagcgt gcgtctggaa gtacgccgga ttgagacaat caagcaaggc     600
aacgatatgg ttggtaaccg tacgcggatt aaagtcgtga agaacaaagt agctcctccg     660
ttcaagcaag cggagattga tatcatgtac ggcgaaggca tttcgagaga aggcagcctt     720
gtagatattg gcgtagagat ggatatcgtt cagaagagcg gagcttggtt ctcctacaat     780
ggcgaccgtc ttggccaagg tcgcgagaat gccaagcagt tcctgaagga tcatccggaa     840
gtggctgctg taatcgagag acaaatccgc gagcaaagca atttgtccgc ttccgcgcag     900
cctgcgaact tctcgcagga tgatgacgat gactttgatg agtcggaact tgacgattaa     960
```

<210> SEQ ID NO 8
<211> LENGTH: 1845
<212> TYPE: DNA
<213> ORGANISM: Paenibacillus sp.

<400> SEQUENCE: 8

```
atgagtaaag ttatcggtat tgaccttggt actacaaact cttgtgttgc tgtaatggaa      60
ggcggcgaag ctgtcgttat cccgaatccg gaaggcaacc gcacaacgcc atccgttgta     120
ggcttcaaaa aagacggaga gcgcattgtc ggcgaaacgg cgaaacgcca agccatcacg     180
aatcccgacc gtacggtaat gtcgatcaaa cgtcatatgg gtactaacca taaagaagtt     240
attgacggca agaatatac ggctcaagag atttcggcta ttattttgca aaaactgaaa      300
tccgatgcgg aagcctatct ggggccaatcc gtaacgcaag cggttattac cgttccggct    360
tacttcaacg acagccagcg ccaagcaaca aaagacgcag gcaaaatcgc gggacttgaa    420
gttcttcgta tcgtcaacga gccaacggcg gctgcgctgg cttacggtct tgagaaaaca    480
gaagaccaaa cgatcctcgt ctatgacctt ggcggcggta cattcgacgt atcgatcctg    540
gaacttggcg acggcttctt cgaagttaaa gcaacaagcg gcgacaacaa gctgggcggc    600
gacgactttg accaagtcat catcgactac ctcgtagccg aattcaagaa agagcaaggc    660
gttgacctgt ccaaagacaa agcggctgtt caacgtttga aagacgctgc cgaaaaagcg    720
```

```
aaaaaagatc tgtccggcgt aatgtcgacg acgatttcgc ttccgttta  cacaatggcc      780 gatggcgttc cacagcactt ggagcttaac ctgactcgcg cgaaattcga agaattgtcc      840
gctcatctgg ttgaacgttc cctcgctcct acgcgccaag ctttgagcga ttccggtctc      900
tccgtaaatg acatcgataa agttgttctt gtcggcggtt cgactcgtat ccctgccgtt      960
caagaagcgg ttaagaagct gatcggcaaa gagccgcaca aaggcgttaa cccggatgaa     1020
gtcgttgccc tcggcgcagc ggttcaagcc ggcgtattga ctggcgacgt aaaagacgtg     1080
gtattgcttg acgtcactcc gctgtccctc ggcatcgaga ctgcaggcgg cgtcttcacg     1140
aagatgattg accgcaatac gacgatccct acaagcaaat cccaagtgtt ctccacttat     1200
gcggataacc aaccgggcgt tgaaattcac gttctgcaag gcgagcgtca aatggctgcc     1260
ggcaacaaaa cgcttggccg cttcacgctg aacgatattc ctctcgcacc gcgcggcgtt     1320
ccgcaaatcg aagttacctt cgacatcgat gcgaacggta tcgttaacgt atccgctctt     1380
gataaaggca caggcaagag ccaaaaaatt acgatcactt cctcgggcgg tctgagcgag     1440
gctgaaatcg agcaaatgat gaaggatgcc gagctgaacg cggaagaaga tcgcaaacgc     1500
cgcgagcttg ttgaagcgaa gaacagcgca gaccaactcg tttactcggt tgacaaaaca     1560
ttgaaagatc tgggcgataa agtagatgct tccgagatcg agaaagctaa cgccgcgaaa     1620
gagaaagtaa caagcgcggt agcgacagac gatctggatc aaattacgaa agctaccgaa     1680
gagctgactg aaatcgtgca acagctgtcc gtgaagctgt atgagcaagc gcaagctgct     1740
caaggcggcc cggaagcagg cgctgaagca gccgatgcag gcgctcgcgg caaagacaat     1800
gttgtggacg ctgactatga agtagttgac gaaaacaaga aataa                    1845

<210> SEQ ID NO 9
<211> LENGTH: 1629
<212> TYPE: DNA
<213> ORGANISM: Paenibacillus sp.

<400> SEQUENCE: 9
atggcaaaag aaattaaatt tagcgaagac gctcgtcgcg caatgctgcg cggtgttgat       60
caacttgcaa acgcggttaa agtaacgctt ggtcctaaag ccgcaacgt ggtactggag       120 aagaaatttg gcagcccgct catcacgaac gacggcgttt ccatcgcgaa agaaatcgag      180
ctggaagacg cattcgagaa catgggcgct caactggtta agaagtagc gactaaaaca       240 aacgacgttg ccggcgacgg tacaacgacg gctaccgttc tggctcaagc gatgattcgc      300
gaaggcctga aaacgttac ggcaggcgct aacccaatgg ttatccgcaa aggcatcgaa       360
aaagcggtta agctgcggt tgaagagctg aaagctatcg ctaaaccaat cgaaggcaaa       420
caatcgatcg cgcaagtagc ttcgatctcc gctgctgacg atgaagttgg ccaactgatt      480
gcggaagcta tggaaaaagt gggcaacgac ggcgttatca ccgttgaaga gtcgaaaggc      540
ttcgtaacgg aacttgaagt ggttgaaggc atgcaattcg accgcggtta cgtttccccg      600
tacatgatca cggatacgga taaaatggaa gctgtcctcg acaatccata cattctgatc      660
acggacaaaa agatctcgaa catccaagag atcctgcctg ttctggagaa agtcgttcaa      720
tccggcaaac agctcctgat catcgcggaa gacatcgaag gcgaagcgca agctacgctc      780
gtactgaaca aactgcgcgg cacattcact tgcgtaggcg ttaaagctcc gggcttcggc      840
gaccgccgca aagcgatgct ggctgatatc gcggctctga ctggcgcgca agtcgtaacg      900
gaagaactcg gccttgagct gaaatccgct actgtgacc aactcggttc cgctcgccaa       960
gttcgcatta cgaaagaaaa cacgatcatc gttgacggca gcggcaaccc tgacgacatc     1020
```

```
caagctcgcg ttaaccaaat ccgcgtgcag ctggaagaaa caacttccga gttcgaccgt   1080
gagaagctgc aagagcgtct ggctaaactg gctggcggcg tagcggtaat caaagtcggc   1140
gcggctaccg aaaccgaact gaaagagcgc aagctccgca ttgaagatgc cctgaactcg   1200
actcgcgcag cggttgaaga aggcatcgta tccggcggcg gtacagctct gatcaatgta   1260
tacaaagcag ttgcggctat tcaaattggc ggcgacgagc aaacaggcgt taacatcgta   1320
ttgcgctccc tcgaagagcc gcttcgcaca atcgctgcga acgctggcca agaaggttcc   1380
gtcatcgttg agcgtctgaa aaacgaaaaa gttggcattg ttacaatgc cgcaaccggc   1440 gaatgggtga acatgttcga agcgggtatc gttgaccctg cgaaagtaac tcgttccgct   1500
ctgcaaaacg cagcttccgt agcggctatg ttcctgacta ccgaagcggt tgttgccgac   1560
aagcctgaga agacaaaacc ggctatgcct gatatgggcg gcatgggcgg tatgggcggc   1620
atgatgtaa                                                           1629
```

<210> SEQ ID NO 10
<211> LENGTH: 1404
<212> TYPE: DNA
<213> ORGANISM: Paenibacillus sp.

<400> SEQUENCE: 10

```
atgaaaaaag gacgcgttgt atccgtcatg ggtccagtcg ttgacttgga gttcgaacgc     60
ggtaacctgc cggaaatttt gaacgccgtc aaaatcgttc aacaggcccc agcaggcggc   120
atcgatatta atctgacgct tgaagtagca gttcacctgg gtgataacct ggttcgtgct   180
gttgcgatga gcacaactga cggtctggtc cgcggcatgg aagctgtaga cacaggcgcg   240
ccaatcacaa ttccagttgg tgcgccaaca ctcggccgcg tatttaacgt actgggcgag   300
ccaatcgacc aagctggcga cgcaacttcg gaaattaacc ttccgattca ccgtcaagct   360
cctgcattcg acgaattgtc cacgcaatcg gaaattctcg aaacaggcat caaagttatc   420
gacttgcttg ctccgtacgc aaaaggcggt aaaatcggtc tgttcggcgg cgcgggcgta   480
ggcaaaacgg taacaatcca ggaacttatc aacaacatcg cgcaagagca tggcggtatc   540
tccgtattcg ccggcgtagg cgagcgtact cgtgaaggta atgaccttta ccacgagatg   600
aaagattccg gcgtacttcc aaaaacagcg atggtattcg gacaaatgaa cgaaccgccg   660
ggcgcacgtc aacgcgtagc cctgacgggt ctgacaatgg ctgaatactt ccgtgacgct   720
gaaggcaaag acgtacttct gttcgtcgac aacatcttcc gcttcacgca agcaggttcc   780
gaggtttcgg cccttctcgg ccgtatgcct tccgcggtag gttaccagcc aacgctggca   840
actgaaatgg gtcaattgca agagcgtatc acatcgacga aaaaggttc ggttacttcg   900 atccaagcga tctacgtacc tgccgatgac tatactgacc cggctcctgc aacgacgttt   960
gctcacttgg acgctacaac taaccttgag cgtaaaatct ccgagatggg tatcttccca  1020
gcggtagatc cacttgcttc gtcgtcccgt atcctgaacc cggacattct gggcgaagag  1080
cattacaacg tagctcaagg cgttaagaaa attcttcagc gctataaaga gcttcaagat  1140
atcatcgcaa tccttggtat ggacgagttg actgaggaag acaagctgac tgtatcgcgc  1200
gcgcgccgca ttcaattgtt cctgtcccaa ccgttccacg ttgccgagcc gttcacaggt  1260
atcaaaggta atacgtacc tgttaaagaa tccgttcgca gcttcaaaga aattctcgag  1320
ggcaaacatg acgaccttcc ggaagaagct ttccggtatg taggtgtgat tgaagaggcc  1380
gtggagaaag ccaaaacgct gtaa                                         1404
```

<210> SEQ ID NO 11
<211> LENGTH: 1967
<212> TYPE: DNA
<213> ORGANISM: Paenibacillus sp.

<400> SEQUENCE: 11

| | |
|---|---|
| atggcagagc aagtagatct tttcgcaaaa acagcggccc cggaacggaa ttacgaggcc | 60 |
| gatgacatac aagtgctcga aggcttgacc gctgtcagaa agcggccggg catgtacatt | 120 |
| ggcagcacga gcagctccgg ccttcatcat ctggtctggg aaatcgtcga taacgccgtg | 180 |
| gacgagcatt tagcgaaatt ttgtacggcg atcgacgtca cgctgcacaa gaatggcgcg | 240 |
| gttaccgtgc aggataacgg gcgcggcatt ccgacaggga tgcataagac aggaattccg | 300 |
| acgccgcagg tcgtattcac catcctgcac gcgggcggca agttcggcgg cggaggatac | 360 |
| aagaaatccg gcggtctgca cggcgtaggc gcttcggtaa caaacgcatt gtccgagtgg | 420 |
| cttgaagtgg aaattttccg tgacgggaaa atacataaga tgcgcttcga atactgggta | 480 |
| gacgataaag gcaaggagca tgtcggcgag ccggtaacag ggcttgagat tacggggaac | 540 |
| acgaaccgaa cgggtagcaa ggtaacgttc aaaccggacg cgcgcgtctt ccagggcggc | 600 |
| acctcgctga actacgatac cctggccgag cgcctgcagg agattgcatt cctgaactcg | 660 |
| ggccttaagg ttacgatcaa ggacgaccgc agcggcaaag aggatatttt ccactacgaa | 720 |
| ggcggcgccc gccagttcgt gcaatatttg aacgacgaca agaccgtcct gcacgatgtc | 780 |
| gttcatttca cgggagagaa ggacgagatt gaagtggaag tagcacttca gtacaacgac | 840 |
| ggatataccg agacgatcgc atccttcgta aactcgatcc cgacacgcgg cggcggtacg | 900 |
| catgagaccg gtttcaaaac cgcttatacg cgggttatga cgaatatgc ccgcaaggct | 960 |
| ggtctcctga aggaaaagga aagaatcta gaaggcaatg atctgcgcga aggcatgatg | 1020 |
| tcggtcatta acatcaagat gtccgaggtc gaattcgtcg ccagacgaa ggaccagctg | 1080 |
| ggcagcgcgt cggctcgcag cgcggtagac gccgtagtct ccgacaagat gcaggtgttc | 1140 |
| ctggaagaga atccacaggt cgcgcaaatg ctgctgaaga aggcggtaca agcctccaag | 1200 |
| gcaagagaag cggcacgcaa agcgcgcgaa gagatccgca gcggcaagaa gaagagcgaa | 1260 |
| agctccaatc tgaacggcaa gctgacgccg gctcagtcga agatttctc gcgcaacgag | 1320 |
| ctgtttatcg tcgaaggcga ttcggcgggc ggctcggcga agcagggccg ggattcgaag | 1380 |
| catcaggcta ttctgccgct gaagggcaag ccgatgaacc cggaaaaagc gaaattgctg | 1440 |
| gatattctga gaacgagga atacaaagcc ataataagcg cgattggagc gggcgttggc | 1500 |
| ccggagtttg acgcggatga atgcaattac agcaaaatca ttattatgac cgacgcggat | 1560 |
| acggacggcg cgcatatcca agtgctgctg ctgacgttct tctatcggta catgaaaccg | 1620 |
| ctgatcgaca ccggggcgcgt ctatatcgct cagccgcctt tatacaagat cactcgcaaa | 1680 |
| tcgggcaagc tggagacggt ccggtatgca tggacggatg accagctgca aaattatttg | 1740 |
| aaggaattcg gcaagaactt tgagcttcag cgctataaag gcttggcga atgaatccc | 1800 |
| gatcagctgt gggagaccac gatggatccg gagacgcgga cgctgctgca ggtgcagatc | 1860 |
| atgcggcaaa agcggaacgc cgcgtgtccg ccctgatggg cgacaaggtt gacccgcgca | 1920 |
| agcgttggat tattgagaac gtagacttca cagtatacgt agaatag | 1967 |

<210> SEQ ID NO 12
<211> LENGTH: 2838
<212> TYPE: DNA
<213> ORGANISM: Paenibacillus sp.

<400> SEQUENCE: 12

```
ttgagcaaac aacaggacaa cagcaaggac aataaagata aaacacgcgt atacgaatac      60
gcgaaatcgc taaacatgag cagtaaagaa attataacga ttcttaaacg gcttaatctg     120
cccgttaata atcatatgag tgtcatggaa aacgaaatgg ttcaaaaagt ggaaggcttc     180
ttccgcgata tcaagcaaaa tgcggctgcg aagcgtgccc aggaatcggg cagtgctacc     240
gtatcggcgg cacctcagcc acaggcacag accgcaagca agcagcaaaa tcaaacggta     300
caaaaaaatc tatctcagga cagacagggg cctatgaatt ctattaaaac gacatccgaa     360
accaaccaat cgcaacaaga acaacgtccg caaagtcagc aaggaaacga aagtcaaacg     420
aacgctagcc aggctaacgc cggcacaagc gacaatagcg caagcagcaa taacagaccg     480
cagaacagcg gcaaccgtca aggttcttat caaggccaag gcggtcaagg cggcaatcgt     540
ccgcaaggcg gcggcggata caaccgtccg caaggtcaag gcggtcaagg tggcaatcgt     600
ccgcaaggcg gcggcggata caaccgtccg caaggtcaag gcggtcaagg cggcaatcgt     660
ccgcaaggcg gcggcggata caaccgtccg caaggtcaag gcggccaagg cggcaatcgt     720
ccgcaaggtc aaggcggcgg cggatttaac cgtccgcaag gtcaaggcgg cgcaccgggc     780
ggcaaccgtc cgcaaggcgg cggcgcacca ggcggtaacc gtccgcaagg tcaaggcggc     840
ggacaaaacc gtacgttcga ttcgtcccgt ccggcaccaa cttcgcgtgg tactgcggca     900
ggcgaaacca acaaccgtaa aggcaacaat gcggtaaaca aaaacagaac gggtggcaac     960
aacggaagcc aaaagcgttt cgacgacggg aagccgaact ttagaacgaa tcctaacggt    1020
cgcggcaaag gcggcagaaa caaccgtaac cattcgcagc agcctccacg cgagaaaatc    1080
gacaatacgc ctaagaaaat cattgtgcgc ggtacgatga cagtaggcga tttggctaag    1140
ctgcttcata aggatgcttc cgaagttatc aagaagctta tttctcttgg cgtaatggct    1200
actatcaacc aagaacttga catggatacc attcttttga tcgctcaaga atttggcgta    1260
gaggttgaag tgaaaattcc ggttgaagaa gataccttcg aaaccgtgga agaagtggat    1320
gacgaagcgg atttgacgac tcgtccaccg gttgtaacga ttatgggtca cgttgaccat    1380
ggtaaaacaa cccttctcga cgctatccgt catacaaacg taacgggcgg cgaagcaggc    1440
ggcatcactc agcatatcgg tgcttaccaa gttgagatca accataagaa aattacgttc    1500
ctcgatacac cgggtcacga agcgtttacg ctcatgcgcg cacgcggtgc tcaagtaacg    1560
gatattacga tcatcgttgt tgcagccgat gacggcgtta tgcctcagac ggttgaagca    1620
gtcaaccatg cgaaagcggc tggcgtgcct attatcgtag cggttaacaa aatcgataaa    1680
ccggacgcgg atcctgacaa aatcaaacag gcgcttacgg aatacgaact cgttccggaa    1740
gaatggggcg gcgataccat cttcgttaac gtatcggcta gcaacgcct tggtctggaa    1800
gagctgctcg agatgattct gctcgtggct gaagttaatg attacaaagc gaattccgac    1860
aaacgcgcac gcggtacggt tattgaagcc gagctggata aggtaaagg tccggtagca    1920
cgcgttctcg tacaacacgg ctcgctgaag attggcgatg ctttcgttgc cggtaactgc    1980
ttcggtcgtg tccgcgcaat ggtgaacgat aaaggccgcc gtatcaaaga agccggtcct    2040
tctactccgg ttgagattac cggtttgaca gaagtaccgc ttgcaggcga tccgtttatg    2100
gtatttgaag acgagcgcaa agcaagagcg attgctgacc gtcgttcgat caaacaacgt    2160
cagtcggagc ttggcgcgaa ttcccgcgtt acgcttgacg atctgttcaa gcatattcaa    2220
gaaggcgaga tcaaagatct taacatcatt atcaagtctg acgttcaagg ctcgacagag    2280
```

| | | |
|---|---|---|
| gccctcaaag | gctcccttgg gaaaattgaa atcgaaggcg ttcgcatcaa gatcattcac | 2340 |
| agcggcgtag | gcgcgatcac ggaatccgat atcaacttgg ctgcggcatc caacgctatc | 2400 |
| gtaatcggat | ttaacgttcg tcctgagccg caagctgatc ttgccgcaca gcaagagaaa | 2460 |
| gtggatgttc | gtctgcaccg cgttatttac aacgtaatcg aagagattga gcaagccatg | 2520 |
| aaaggcatgc | tggatccaat cttcaaagaa gttgttcaag gtcaagcgga agtccgcaac | 2580 |
| atctttaagc | tcagcaaggt tggcgctatt gccggatgta tggttatcag cggcaaaatt | 2640 |
| acgcgtaact | ccgaagttcg cgtcatccgc ggcggtatcg ttgtattcga aggcaaaatg | 2700 |
| gataccgtta | aacgcttcaa ggatgatgtt aaagaagttg ctcaaggcta cgagtgcggt | 2760 |
| attacgatcg | agcggtttag cgacttcaaa gaaggggata ttattgaagc cttcgtaatg | 2820 |
| gagtccgtag | agaggtga | 2838 |

<210> SEQ ID NO 13
<211> LENGTH: 2250
<212> TYPE: DNA
<213> ORGANISM: Bacillus megaterium

<400> SEQUENCE: 13

| | | |
|---|---|---|
| atgttcgata | taggcggtga aaacgtgaat tttttaagtg aaaaattatt aacaggatta | 60 |
| aaccctcagc | aacaagaggc agttaaaacg acagacggac cactattact tatggccggt | 120 |
| gcaggaagtg | aaaaacacg tgtattaacg catcgaattg cgtttttaat ggcagaaaaa | 180 |
| gaagttgcac | cttggaatat tttagccatt acttttacaa caaagcagc tcgtgaaatg | 240 |
| agagagcgtg | tttcaaatat cgttggcgga gtggcagaag atatctggat ttcaacgttc | 300 |
| cactcgatgt | gcgtgcgtat tttacgaaga gatattgatc gtattggctt taatcgtaac | 360 |
| tttacgattt | tagattcaac ggatcagctg tccgttatta aaatattttt aaagatcaa | 420 |
| aacatcgatc | cgaaaaaatt cgatccgcgc tcgttattag gaagcattag ttcagctaaa | 480 |
| aatgaactga | aagtagcgga agaatttgat aaaacagcag cgggaccgta tgaagaagtt | 540 |
| gtaagcaaag | tctacaaaga gtatgaaaag cgtttaaaga aaaccaagc gcttgatttt | 600 |
| gatgatttga | ttatgacaac gattcagcta tttaaacgag ttcctgaagt gttaacttac | 660 |
| tatcagcgca | agtttcaata tattcatgtg gacgagtatc aagatacaaa ccatgcacag | 720 |
| tatatgctgt | tcgcttgct agctgcaaga tttgaaaatg tatgcgtagt aggggattca | 780 |
| gatcagtcta | tttaccgctg cgcgggggct gatattacaa atatcttgtc atttgaaaaa | 840 |
| gattacccaa | aagcgaaaac catttttgctt gaacaaaatt atcgttcaac taaaacgatt | 900 |
| ttggctgcgg | caaacggcgt cattgcaaac aatatgaatc gtaaagtgaa aaacttatgg | 960 |
| acggaaaacg | atgaaggcca gaagatttac cattaccaag caatgagtga gcatgatgag | 1020 |
| gcacagtttg | tagcacgtaa aattaaagaa gcagtagaca gcggaaagcg taaatacagt | 1080 |
| gattttgcca | ttttgtatcg tacaaatgca cagtctcgtg tgatggagga agtgctgtta | 1140 |
| aaatccaata | ttaattatac aattgtcggc ggcattaagt tctacgaccg caaagagatt | 1200 |
| aaagatttac | ttgcgtactt gcgcttaatt gccaaccaag atgatgacat tagcttagct | 1260 |
| cgtattgtga | acgttccaaa gcgcggagtt ggagctactt cagtcgataa agtggccaat | 1320 |
| tacggaaacg | ttcatgacat ttcgattttc aaagcactgg atgaagtaga attaatgggg | 1380 |
| ttaacaggca | aagcaacaaa agcccttcgt gatttccaat cgatgatttc gaacttagct | 1440 |
| caaatgcaag | actatatgtc tgttacagag cttgtggaac aagtattaga agaacggga | 1500 |
| taccgtgaag | cgcttaaagt ggaaaaaaca attgaagcac aaagccgctt agagaatatt | 1560 |

```
gatgagtttt tatctgtcac aaaaacgttt gaagaagcaa gtgaagataa aagcttagta    1620
gcatttttaa ccgatttagc acttgttgct gatatcgata agcttgacga cgaggaagaa    1680
gaagagaacg aacaagtgat tctgatgacg cttcactcgg caaaaggtct agagttcccg    1740 gttgttttc taatgggtat ggaagaaggc gtattccctc atagccgatc attattcgaa    1800
gataatgaaa tggaagagga acgacgctta gcctatgtag gaattacgcg tgctgaacaa    1860
gaattatatt tattaaatgc tcaaatgcgc acactatttg gtaaaacaaa cgttaatcca    1920
aaatcgcgct tcattggaga atcccaagc gagcttgtgg aatctttaaa tgaagcaatg    1980
cgcaaacctg ctgctggtcg ttcagggct tcagcttcgc cgtttgcagc gcgccgacaa    2040
gcggccgtgg caaaaacgaa gcttgtgtca acaggcagtg aatcaattgg atggagcgtt    2100
ggagacaagg ctgagcataa aaaatgggga attggtacag ttgtaagtgt aaaaggagaa    2160
ggagattcaa agaattaga cattgctttt cctagtccta caggtgtaaa aagactgctt    2220
gctaaatttg ccccggttac gaaagtgtaa                                    2250
```

<210> SEQ ID NO 14
<211> LENGTH: 2517
<212> TYPE: DNA
<213> ORGANISM: Bacillus megaterium

<400> SEQUENCE: 14

```
atgcttggat tatttaaaaa agtgtttgac ggcaatcagc gccaaatcgg ccgtttagaa      60
aaaatggcgg accaaattga tgcgttaggt cctgaaatag cgtctttaac agacgatcag     120
cttcgtgaaa aacggctga atttcaacaa cgctaccaaa atggcgaatc gctcgataac     180
ctattagatg aagcttttgc ggttgtacgt gaagcagcga acgtgtgtt aggcatgtat     240 ccgtacaaag ttcagctaat gggggtatt tctctgcatg aagggaatat ctcggaaatg     300
aaaacgggtg aaggtaaaac gttgacagct actatgcctg tatacttaaa cgccattaca     360
ggaaaaggtg tacatgtagt aacagtcaat gaatacttag cgagccgtga tgctagtgaa     420
atgggtcgtt tatatgaatt cctaggtttg aaagtaggtt taaatttaaa ccatttaacg     480
cgtgaagaaa agcaagaagc atatgcagcg gatattacgt atagtacaaa taatgaactc     540
ggatttgact atttacgtga taacatggtg ctttacaaag aacaaatggt tcaacgtccg     600
cttcattttg ccgtaatcga tgaagttgac tctatcttaa ttgatgaagc acgtacgccg     660
cttattatat cgggcagcgc gcagaaatcg actgctcttt atattcaagc taatgcattc     720
gttcgcacgc ttgataaaga aaccgatttt acttttgata tcaaaacaaa aagcgttcag     780
ctaaccgaag aaggtatgtc aaaagcagag cgcgcatttg gcattgaaaa cttatttgat     840
atttcacacg tagcgctaaa ccatcacatc aaccaagcgc ttaaagcaca tgtaacgatg     900
caaaatgatg tggattacgt aattgatgaa gatcaggtcg taatcgttga ccaatttact     960
ggtcgtttaa tgaaggaag acgttttagc gacggcttgc atcaagctat cgaagctaaa    1020
gagaatgttg agattcaaaa tgaaagcatg acgttagcta caattacatt ccaaaactac    1080
ttccgtatgt atgaaaaatt atcaggtatg acgggtacag ctaaaacgga agaagaagaa    1140
ttccgtaata tctacaacat gcacgttgtt gttattccga caaacaaacc aatttcacgt    1200
gatgataaag cggatttaat ttataagtcg atggaaggca gtttaatgc ggtagtagaa    1260 gatattgccg agcgccacgc aaaaggacag cctgttcttg ttggtacagt tgcgatcgaa    1320
acatctgaag ttttatcagc tttattaaag aaaaaaggca ttcgccatca cgtgttaaat    1380
```

-continued

| | |
|---|---|
| gcaaaacagc atgagcgtga agcggatatt attgaaaatg cgggtcacaa aggtgcggta | 1440 |
| acaatcgcaa cgaatatggc cggtcgtggt acggatatca aactaggtga aggtgtcgtt | 1500 |
| gaagctggcg gtcttgctgt aattggtaca gagcgtcatg aatcacgccg tattgataat | 1560 |
| cagcttcgcg gacgtgctgg acgtcaaggt gatccagggg tatctcaatt ctatctatcc | 1620 |
| atggaagatg aattaatgcg ccgatttggt tcagataata tgatggcaat gatggatcgc | 1680 |
| cttggcatgg atgactcaca gccaattcaa agtaaaattg taacaagagc tgttgaatcc | 1740 |
| gctcaaaaac gcgttgaagg taataacttc gatgcgcgta acaattgct tcaatatgat | 1800 |
| gacgtgcttc gtcaacagcg tgaagttatt tacaaacagc gctttgaagt acttgattca | 1860 |
| gacaacctgc gtgcgattgt agaacgtatg attgaatcaa ctctacagcg tgtggttgaa | 1920 |
| gtaaacacac cgcgtgaaga attagaagaa gaatggaatt tacaagcgat tattgattac | 1980 |
| gtaaatgcta atgttcttga ggaaggtgaa gtcacagaag aagatcttcg ccgtaaagag | 2040 |
| cctgaagaaa tggtagaact gctggtagat catgcaaaag ctcgttataa tgaaaaagaa | 2100 |
| gagcagctcc ctgaagaaca aatgcgtgaa tttgaaaaag ttgttgttct tagagcagtt | 2160 |
| gattctaaat ggatggatca tatcgatacg atggatcagc ttcgccaagg tatccacctt | 2220 |
| cgtgcgtacg gccaaacaga tcctcttcgc gaataccaaa tggaaggttt tgcgatgttt | 2280 |
| gaaaatatga ttgcaaccat tgaagaagaa gtgacgaagt atatcatgaa agcagaaatt | 2340 |
| aacaacaacc ttgagcgtca agaggtagcg caaggtcagg cggctgttca tccaaaagaa | 2400 |
| ggagacgcgc cggctaagaa gaagccaaaa gtaaatgcaa tagaagttgg ccgaaatgat | 2460 |
| ccttgtatct gcggaagtgg caaaaagtat aaaaactgct gcggtaaaga atcataa | 2517 |

<210> SEQ ID NO 15
<211> LENGTH: 1074
<212> TYPE: DNA
<213> ORGANISM: Bacillus megaterium

<400> SEQUENCE: 15

| | |
|---|---|
| atgaacggat atttacactt agcaaacggc gattcgttcg ccggacacat tgaacataca | 60 |
| gcaacgcacc aggcagaagg agaaattgtt ttctttactg gaatgactgg ttatcaagaa | 120 |
| gttgtgactg atccatctta caaagatcaa attatcgtct ttacgtaccc tttgattggg | 180 |
| aactatggta tcaatgaaaa agattatgaa agcaaaaagc ctcacgtagc aggcgttgtc | 240 |
| gtatacgaat gttcagatga agggttccat tacgaagcga tgtacagctt taaacaatat | 300 |
| ttaaagaaat ggaacattcc gcttattaca catgtggata cgagagcggt cgtaaaacga | 360 |
| attcgaaaag aaggtacgat gcaatctgcc ttttcgacat ctgctgagcc gccagcattt | 420 |
| actgctgaat gcgatggata tgtagtaaaa gaagtatcaa caaagagcc tgttacttac | 480 |
| ggaaacggtg aaaaacacgt tgtattaatg gactttggct ataaaaatc aattttacaa | 540 |
| gagctgttaa tcgagagtg caaagtaaca gttgttcctt attctacaag ctcttcaaaa | 600 |
| gtaaaagagc tgcagccgga tggcattgtc ttatcaaacg gacctggaga tccaacccaa | 660 |
| gtgagcagtc agctggatga attaaaagaa attatttcat cgtatccaac tttgggaatt | 720 |
| tgctttggac atcagttaat tgggcttgct tttgggcac aaaccaaaaa gctggcgttc | 780 |
| ggtcaccgag gagctaatca gcctgtaatt gatttaacga ataacaaagt gtgtatgact | 840 |
| tctcaaaacc atagctatgt cgtggacgaa cagacgatta cgtctacgcc attaaatgtt | 900 |
| cggtttaaaa atgtgaatga cggatcggtt gaaggtttaa tgcataaaga ccttcctgtt | 960 |
| atgtcggttc aatatcatcc agaagcacac cctggaccaa gtgacagcac gtatatcttt | 1020 | gatgaattta tgacgaaagt acagcaagta gggagcggaa aagtatatgc ctaa        1074

<210> SEQ ID NO 16
<211> LENGTH: 1038
<212> TYPE: DNA
<213> ORGANISM: Bacillus megaterium

<400> SEQUENCE: 16
gtgaacgatc gtcaagcagc ccttgatatg gctttaaaac aaattgaaaa gcaatttggt        60
aaaggttcaa ttatgaaatt aggtgaacaa acggaaaaaa gaatttctac aattccaagt       120
ggttcattag cgttagatat agccttaggt gtaggtggat atccacgtgg acgtgtagtt       180
gaagtatatg gtccagaaag ctcaggtaaa acaacagttg ctcttcatgc gattgcagaa       240
gttcaacagc agggcggaca ggctgcattt atcgatgcgg agcacgcgtt agatcctgta       300
tatgctcaaa aattaggtgt gaatattgat gagctattat tatctcagcc tgatacggga       360
gaacaagctt tagaaattgc tgaagcttta gttcgaagcg tgcagtagaa tattatcgtt       420
gttgactcag tagcagcatt agtgccaaaa gcagaaattg aaggagaaat gggagactct       480
cacgtgggtc tacaagctcg tttaatgtct caagcattgc gtaaactatc tggagctatc       540
aacaagtcta aacaatcgc tatctttatt aaccaaattc gtgaaaagt cggcgttatg       600
tttggtaacc ctgaaacaac tcctggtgga cgtgcgctta aattctattc ttcagtgcgt       660
ctagaagtgc gtcgtgcaga gcagttaaag caaggaaacg atattgtagg taacaaaaca       720
agaattaaag ttgtgaaaaa caaagtagct ccgccattcc gtgctgctga agtagatatt       780
atgtacggag aaggtatttc aaaagagggc gaaattttgg atatcgcttc tgaactagat       840
attgttcaaa aagtggatc ttggtattca tataatgacg agcgtctagg tcaaggtcgt       900
gaaaatgcaa acaattctt aaaagaaaat actgatattc gtcaggaaat tgcgggacaa       960
gtgcgtgaac atcatggttt agaccaagat ggagagccag ctcctgagga tgacgatcaa      1020
ggcgatttaa atatttaa                                                    1038

<210> SEQ ID NO 17
<211> LENGTH: 1818
<212> TYPE: DNA
<213> ORGANISM: Bacillus megaterium

<400> SEQUENCE: 17
atgagtaaga tcattggtat cgatttaggt acaactaact cttgtgtcgc tgtattagaa        60
ggcggcgaac aaaagtaat tccaaatcca gaaggaaacc gtacaacacc atcagttgtg       120
gcattcaaaa acggtgagcg tcaagttggg gaagtagcga acgtcaagc tattacaaac       180
cctaacacaa ttatttcagt taaacgtcat atgggtacag accataaggt ggaagctgaa       240
ggcaagcaat acacgcctca agaaatgtca gctatcattc ttcaacattt aaaaggttat       300
gctgaagagt atttaggtga gcctgtaaca aaagctgtta tcacagttcc tgcttacttt       360
aatgatgctg agcgtcaagc aacaaaagat gctggtaaaa ttgctggttt agaagtagag       420
cgtattatta cgagcctac tgcagcagca cttgcatacg gattagaaaa acagatgaa       480
gatcaaacag ttttagttta tgaccttggt ggcggtacgt ttgacgtatc tattctagaa       540
cttggcgacg gcgtatttga agttcgcgca actgcaggtg acaaccgcct tggtggtgac       600
gactttgacc aagtaatcat cgactatttta gtcgctgaat tcaaaaaaga aaacggcgtt       660
gatttaagca aagataaaat ggcgcttcaa cgtttaaaag atgcggctga aaaagcgaaa       720

```
aaagatttat caggtgtaac atctacacaa atttctttac catttatcac tgctggagaa    780
gctggccctc ttcacttaga ggtatcttta tcacgtgcta aatttgatga gttatcagca    840
ggtcttgtag agcgtacaat ggctcctgtg cgtcaagctt aaaagatgc aggcctttct    900 gcaagcgaac ttgataaagt aatcttagtt ggtggttcaa ctcgtatccc agcggtacaa    960
gatgcgatca aaaagaaac tggtcaagat cctcacaaag gtgtaaaccc tgatgaagta    1020
gttgcacttg gtgcagcaat tcaaggtggc gtattaactg gtgatgtaaa agacgttgta    1080
ttactagacg taacgccttt atcactaggt atcgaaacaa tgggtggcgt atttacaaag    1140
ctaattgagc gtaatacgac gattccaaca agtaaatcac aagtattctc aacggctgca    1200
gatagccaaa cggctgtaga tattcatgtt cttcaaggtg agcgtccaat gtctgcagac    1260
aataaaacgc taggtcgttt ccagttaact gatattccac ctgcaccacg cggagtacct    1320
caaatcgaag tatcattcga tattgacaaa aacggtatcg taaacgttcg tgcaaaagat    1380
ttaggtacaa acaaagagca agctattaca attaaatctt caacaggttt atcagatgat    1440
gaaatcgacc gtatggtaaa agaagcggaa gaaaacgcag atgctgataa gcaacgtaaa    1500
gaagaagtgg aactacgcaa tgaagcagat caattagtgt ttacaactga aaaaacatta    1560
aaagatcttg aaggaaaagt agaagaagct gaagtaacaa aagctaacga agcaaaagat    1620 gcttttaaaag cagcgattga aaagaatgac cttgaagaaa tcaaagcgaa aaagatgaa    1680 cttcaagaaa tcgttcaagc gttaactgta aaattgtatg agcaagctca acaagctcag    1740
caagcaggtg aacaaggcgc tcaaaatgat gatgttgtag atgcagagtt tgaagaagta    1800
aacgacgaca aaaaataa                                                  1818

<210> SEQ ID NO 18
<211> LENGTH: 1632
<212> TYPE: DNA
<213> ORGANISM: Bacillus megaterium

<400> SEQUENCE: 18
atggcaaaag acattaaatt tagcgaagaa gcacgtcgcg caatgctacg tggtgtagat     60
acattagcaa atgctgtaaa agtaacgctt ggaccaaaag gtcgtaacgt tgtattagaa    120
aagaaattcg gttcaccgct tattacaaat gacggtgtaa caattgcaaa agaaatcgaa    180
ttagaagacg catttgaaaa tatgggtgct aaattagtag cggaagttgc tagcaaaaca    240
aacgacgttg ctggtgacgg tacaactact gcaacagttt tagcgcaagc aatgatcaga    300
gaaggtctta aaacgtaac ggctggtgct aacccaatgg gtatccgtaa aggtatggaa    360
aaagcagtag ctgtagcggt tgaagaacta aaagcaatct ctaaaccaat tcaaggtaaa    420
gattcaattg ctcaagtagc ggctatctca gcagctgacg aagaagtagg tcaattaatt    480
gctgaagcaa tggagcgcgt tggtaacgac ggcgttatca cacttgaaga atcaaaaggt    540
ttcacaactg aattagaagt ggtagaaggt atgcagtttg accgtgggta tgcatctcct    600
tacatggtaa ctgattcaga taaatggaa gctgtattag atgatccata catcttaatc    660
acagacaaaa aaatcggtaa cattcaagaa atcttaccgg tattagagca agttgttcaa    720
caaggcaagc tctattaat catcgctgaa gacgtagaag cgaagcatt agcaacatta    780 gttgtgaaca acttcgtgg tacattcaca gctgtagctg ttaaagctcc tggtttcggt    840
gatcgtcgta agcaatgct acaagatgtt gcaatcctaa caggcggaga agtaatcact    900
gaagagcttg gtcttgacct aaaaacagca agcatcgatc aattaggtcg cgcttctaaa    960
attgttgtaa caaaagaaaa tacaacggtt gtaaacggtg caggaaacgc agaagatatc   1020
```

```
ctagcacgcg taaaccaaat caaagctcag cttgaagaaa caacttcaga gtttgaccgt    1080
gaaaaattac aagagcgctt agcaaaactt gctggtggcg tagctgtaat taaagttggt    1140
gcggcaactg aaactgagtt aaaagaacgt aaattacgta ttgaagatgc attaaactct    1200
acgcgtgctg cggttgaaga aggtatcgta gctggtggtg gtactgcatt agtaaatatc    1260
tataataaag tagcaagcat cgaagctgac ggtgacactg ctacaggtat caacatcgta    1320
ttacgtgcga ttgaagagcc tgtacgtcaa atcgctcaca cgctggttt agaagggtca    1380 gtaatcgttg agcgtctaaa aggcgaagct gttggaactg gatttaacgc tgcaactggc    1440
gagtgggtaa atatgctaga cactggtatc gttgacccaa caaaagtaac gcgttcagct    1500
cttcaaaatg cttcttctgt agcggctatg ttcttaacaa ctgaagcagt tgttgctgac    1560
aagccagaag aaggcggagc acctgcaatg cctgacatgg cggcatgggt ggaatgggc    1620 ggcatgatgt aa                                                       1632
```

<210> SEQ ID NO 19
<211> LENGTH: 1422
<212> TYPE: DNA
<213> ORGANISM: Bacillus megaterium

<400> SEQUENCE: 19

```
atgacaaaag gacgcgttac tcaaatcatg ggtccagttg tagacgtaaa gtttgacaac      60
ggacaccttc cggcaattta taacgcccct aaaatttcac ataaaccgag cagtgcaagt     120
gaagttgcaa tcgaattaac attagaagtt gcgattcact taggtgataa cacagttcgt     180
acagtagcaa tgtcatccac tgacggctta gttcgtggat tagaagtaga agatacaggt     240
gcagcaatct cagtaccagt tggtgacgtt acattaggtc gtgtatttaa cgtattaggt     300
gaaaaaatcg acttagacgc tccaatcgat gcaggtgcac gtcgtgatcc aatccaccgt     360
caagcaccaa agttcgaaaa tctatctaca caagctgaaa ttcttgaaac aggtattaaa     420
gtagtagact tattagctcc ttacattaaa ggtggaaaaa tcggtctatt cggtggtgcc     480
ggtgtaggta aaacagtatt aattcaagag ttaatcaata acattgctca agagcacggc     540
ggtatttcgg tattcgctgg tgtaggtgag cgtacgcgtg aaggtaatga cttataccat     600
gaaatgacag attccggtgt tattaagaag acggctatgg tatttggaca aatgaatgag     660
ccacctggtg cacgtcaacg tgttgcatta acaggattaa caatggcaga atacttccgt     720
gacgaacaag gtcaagacgt attattcttt atcgataata tcttccgttt cacacaagcg     780
ggttcagaag tatcagcatt acttggccgt atgccatcag cagtaggtta tcagccaaca     840
ttagcgacgg aaatgggtca gcttcaagag cgtatcacgt caacaagcgt aggttctgta     900
acatcgattc aagcgattta cgtaccagcc gatgactata cggatccagc tccagcgaca     960
acatttgctc acttagatgc aacaacaaac ttagagcgta aattatcaga gatgggtatt    1020
taccctgcgg tagatccatt agcatctaca tctcgcgctt tatctcctga aattgttgga    1080
gaagagcact atgcaattgc gcgtcaagtt caacaaacgt tacagcgtta taagagtta    1140 caagatatca ttgcaatcct aggtatggat gagttatctg atgaagataa acttgttgta    1200
caacgtgctc gtcgcgttca attcttcttg tctcaaaact tccacgtagc agagcaattt    1260
acaggtcaaa aaggttctta tgttcctgta aaagaaactg ttaaaggatt taaagagatc    1320
ttggaaggta aatacgatca tttacctgaa gatgcgttcc gtttagttgg tcgcattgaa    1380
gaagttattg aaaatgcgaa acgtatggga gtagaagttt aa                      1422
```

<210> SEQ ID NO 20
<211> LENGTH: 1917
<212> TYPE: DNA
<213> ORGANISM: Bacillus megaterium

<400> SEQUENCE: 20

| | | | | | |
|---|---|---|---|---|---|
| atggaacaaa | aagaagtaca | agcatatgaa | gctgatcaga | tacaagtatt | agaaggatta | 60 |
| gaagctgttc | gtaaacgtcc | ggggatgtat | attggatcga | cgagcgcaaa | gggtttacat | 120 |
| catcttgtat | gggaaattgt | agataatagt | attgatgaag | cgctggccgg | ctattgcgat | 180 |
| gaaattaatg | ttattatcga | aaaggataat | agtattacag | tcaaagataa | cggtcgtgga | 240 |
| attccggttg | gtattcaaga | aaaaatgggc | agacctgctg | ttgaagttat | cttaacggtt | 300 |
| cttcatgccg | gaggtaaatt | tggcggtggc | ggctataaag | tatccggtgg | attacacggt | 360 |
| gtaggtgcct | cagttgttaa | cgcactttct | acctctttgg | aagtgcacgt | acatcgtgac | 420 |
| ggtaaagttc | attatcaaaa | atatgaacga | ggtgtaccgg | ctgctgactt | aaaagtagtt | 480 |
| ggagaaacag | ataaaacagg | tactgttatt | caattccgtc | cagacagtga | aattttaca  | 540 |
| gaaacgcttg | aatacgattt | tgatacgtta | gctaatcgtc | tgcgtgagtt | agctttctta | 600 |
| aatcgcggca | ttaaaattac | gattgaagat | aaacgtgaag | aagataaaag | acgtgaatat | 660 |
| cactatgaag | gcggaattaa | gtcttacgtt | gaacacttaa | accgttcgaa | agaagtgatt | 720 |
| cacgaagagc | cgatctatat | tgaaggtaat | cgagacaaca | tttctgtaga | aattgctatt | 780 |
| caatataacg | atagctatac | aagtaattta | tattcttttg | caaacaacat | tcacacatat | 840 |
| gaaggtggaa | cgcacgaagc | aggatttaaa | acagcgttaa | cgcgtgtaat | taacgactat | 900 |
| gcacgtaaaa | acagcgtatt | taaagacagt | gacgccaatc | taacgggtga | agatgttcgt | 960 |
| gaaggaatta | cagctatcat | ctctattaag | cacccagatc | cgcagttcga | aggacaaaca | 1020 |
| aaaacaaagc | tgggaaatag | tgaagcaaga | acaattactg | actctgtgtt | tgcagaacac | 1080 |
| ttagaaactt | acttgctaga | gaaccctatt | gtggcgaaaa | aggtaattga | aaaaggttta | 1140 |
| atggctgcaa | gagcaagaat | ggcagctaaa | aaagctcgtg | agcttacacg | ccgtaaaagc | 1200 |
| gcgcttgaaa | tttcaaactt | accgggtaaa | ttagcagatt | gttcatcaaa | agatccttct | 1260 |
| attagcgaac | tttatgtagt | agagggtgac | tctgccggag | gttcagctaa | gcagggaaga | 1320 |
| agccgtcatt | tccaagctat | tttgcctttg | cgtggtaaaa | ttatcaacgt | agagaaagcg | 1380 |
| cgtttagata | aaatttttatc | taataacgaa | attcgtacaa | tcattaccgc | tctaggaacg | 1440 |
| ggtattggtg | acgattttga | tatttcgaaa | gcccgctacc | ataaaattgt | gattatgaca | 1500 |
| gatgcagacg | tagacggtgc | gcatattcgt | acgcttcttc | taacgttctt | ctatcgctat | 1560 |
| atgagacaga | ttattgagca | cggatatgtg | tacattgccc | agccgcctct | ttacaaagtt | 1620 |
| acacagggta | aaaagtgga  | gtatgcgtac | aacgatcgtc | aattagaaga | ggtattagct | 1680 |
| tctttccctg | aaggtgcaaa | accaaaacctt | cagcgttaca | aaggtttagg | agagatgaat | 1740 |
| cctgaacaat | tatgggaaac | aacaatggat | ccagagttcc | gtaccttct  | tcaggtgaac | 1800 |
| ttgcaagatg | caattgaagc | tgatgagaca | tttgaaattt | taatgggcga | caaagtagaa | 1860 |
| ccacgccgta | atttcattga | agaaaatgct | cagtacgtaa | aaaatcttga | tatttaa    | 1917 |

<210> SEQ ID NO 21
<211> LENGTH: 1887
<212> TYPE: DNA
<213> ORGANISM: Bacillus megaterium

<400> SEQUENCE: 21

```
atgggggtga aagtattgaa taaaaataca aaatcaacag ctaacaaagg aaacaataaa       60
ggtaacaaaa agccacaggc acaaaagtca caggcaccaa aaggtagacc agctccagca      120
gctgcaaaag agttaccgga aaaagtaacg tttgtcggaa gcttaacggt ttctgagtta      180
gcaaaagaat taggcaaaga gccttctgaa attattaaaa aactatttat gcttggtgta      240
atggcaacaa ttaaccaaga gttagataaa gattctatcg aactaattgc cggagaatac      300
ggtgtagaag ttgaagaaga agtagtagta gatgacactg cttttgaatc attagaaatc      360
attgatgacg aaaaagacct tcaagtgcgt cctccagttg ttacaatcat gggtcacgtt      420
gaccacggta aaacgacgct tcttgactct atccgtaaca caaagtaac ggctgcagaa      480 gcaggcggta tcacgcagca tatcggtgct tatcaagttg tggttgatga aaagaaaatt      540
acattccttg atacaccagg gcatgctgca tttacaacga tgcgtgctcg cggtgcgcaa      600
gtaacggata ttacaatcct tgttgttgca gcagacgatg gtgtaatgcc tcaaacaatt      660
gaagcgatta accatgcaaa agcggcagaa gtgccaatta ttgttgcggt taacaaaatg      720
gataaagaag cagcaaatcc agatcgcgtg atgcaagaac taatggagca cggccttgta      780
gctgaagagt ggggcggaga aacaatcttc tgtaagcttt cagccatttc aggtgaaggg      840
atcgatcaat tgcttgaaat gattttactt gtaagtgaag tagaagagtt aaaagcaaat      900
ccgaaccgtc gtgcagcagg tacagttgta gaagcacagc tagataaagg ccgtgggtct      960
gtagcaacgc ttcttgttca aactggtaca ctacgcgtag gtgatccaat cgtagtcgga     1020
aatacgtttg ccgtgttccg cgcaatggta aatgatatcg gccgccgtgt gaaggaagta     1080
ggaccatcta ctccggttga gattactggc ttaaacgaag ttccgttagc tggagatcgt     1140
ttcttagtgt ttgaagatga gaaaacagct cgtcaaatcg gagaagctcg tgctcaaaag     1200
cagcttgaac aacagcgcgg tgaaaaatct cgcgtaagct tagatgattt atttgaaaaa     1260
attaaacaag gcgaaatgaa agacttaaac cttatcgtaa aagcagacgt acaaggttct     1320
gtagaagcat tggctgctgc tcttcaaaag attgatgtag agggtgtaaa tgttcgtatt     1380
atccatacgg gtgtaggtgc gattacagaa tctgatatca ttcttgcaac tgcttctaac     1440
gcaatcgtta tcggctttaa cgtgcgtccg gatgctggag caaaacgtac agctgacgta     1500
gaaaacgtag atattcgtct tcaccgcatt atttataaag taattgaaga aattgaatct     1560
gcgatgaaag aatgcttga tcctgagttt gctgaaaaaa tcatcggtca gtggaagta     1620 cgtcaaacat tcaaagtatc aaaagttggt acaatcgcag aagttacgt aacagatggt     1680 aaaattacac gtaacagtgg aattcgttta atccgtgacg gaattgttat ctttgaaggt     1740
gaagtagatg tgctaaaacg ctttaaagac gatgcaaaag aagtcgctca aggatatgag     1800
tgtggtatta caattaaaaa cttcaacgat attaaagaag gagatattat tgaagcatat     1860
gtaatggagc aaattgatcc taaatga                                          1887
```

<210> SEQ ID NO 22
<211> LENGTH: 2220
<212> TYPE: DNA
<213> ORGANISM: Bacillus subtilis

<400> SEQUENCE: 22

```
ttgaattata ttagcaatca attactaagc ggtttaaacc ccgttcagca ggaagcagtc       60
aaaacaacgg acgggcccct tttgctgatg gcgggagcgg gaagcggaaa gacgcgtgtc      120
ctgacacaca gaattgctta tttaatggca gaaaagcatg tggcgccgtg gaacattctg      180
```

```
gcgatcacat ttacaaataa agcggcacgc gaaatgaaag aacgtgtgga aagcatcctc    240
ggacccggcg cggacgatat ctggatttcc acattccaca gcatgtgcgt gcggatcttg    300
cgcagagata tcgaccggat tgggatcaac cgaaatttct ccatccttga tacggctgac    360
cagctttcag tgattaaggg gattttgaag gagcgcaatc ttgatccgaa gaagtttgac    420
ccgagaagca tcctcggcac gatcagcagt gcgaaaaacg aattgaccga accggaggaa    480
ttctctaagg ttgccggcgg ctactacgat caggtggtca gcgatgtata tgctgattat    540
cagaagaagc tattgaaaaa ccagtcgctc gatttcgacg atttgattat gacgacgatt    600
aaactgtttg accgagtgcc ggaagtactt gaattttatc agcgcaaatt ccaatacatc    660
catgttgatg agtatcagga tacgaacagg gcgcaataca tgcttgttaa gcagcttgcc    720 gagcgttttcc agaacctttg cgttgtgggg gattctgatc agtcaatcta cagatggcgc    780
ggcgcggata tcaccaacat cctttcattt gaaaaagatt atccgaatgc aagcatgatt    840
ttgctagaac aaaactatcg ttcaacgaaa cggattttgc gtgcggctaa cgaggtcatc    900
aaaaacaact ctaaccgcaa accgaaaaat ttgtggacgg aaaacgatga aggcataaaa    960
atttcctatt atcgcggtga taatgaattc ggagaaggac agtttgtggc cggtaaaatt   1020
catcagcttc acagctcagg caagcggaag ctgtctgata tcgccatatt ataccggaca   1080
aacgcgcagt cccgtgtgat tgaggaaacg cttctcaaag cgggcttgaa ctataacatt   1140
gtcggcggca caagttcta tgacagaaaa gaaattaaag acattcttgc gtacctgcgc   1200
ctcgtatcca atccggatga cgatatcagt ttcacgcgca ttgtcaatgt gccgaagcgc   1260
ggagtcggcg cgacatcact tgaaaaaatc gcttcgtatg cggccataaa cggcttgtca   1320
tttttccaag cgattcagca ggttgatttt atcggcgtca gtgccaaagc ggcaaacgcg   1380
cttgacagct ttagacagat gattgagaat ctgaccaata tgcaggatta cttatccatt   1440
acagagctga cagaagaaat tcttgataag acggaataca gagaaatgct gaaggctgag   1500
aaatcgatcg aagcccaaag ccgtttagaa aatatcgacg agttcctgtc tgttacgaaa   1560
aactttgaac agaaaagtga agacaagaca ctcgttgcgt tcctgacaga cttggcattg   1620
atcgcagata ttgatcagct cgatcagcag gaggaagagt caggcggcaa ggatgcgatc   1680
accctgatga cactgcacgc cgcgaaagga ctggagttcc cggttgtttt cttgatgggg   1740
cttgaagaag cgtcttccc gcacagccgt tctctcatgg aggaagcgga aatggaagaa   1800
gaacgccgcc ttgcgtacgt tgggattaca agggcggaac aggagcttta tctgaccaat   1860
gctaaaatgc gcaccttgtt tggccggaca aatatgaacc cggaatctcg cttcattgct   1920
gaaataccgg atgatttatt ggaaaaccta atgagaaaa agaaacgag agcgacgtct   1980 gcgagaaaaa tgcagccgag acgcggccct gtttcacgcc cggtatccta cgccagcaaa   2040
acaggcggcg acaccttgaa ctgggcagtc ggagataagg cgggccataa aaaatgggga   2100
acaggaactg ttgtcagcgt gaaaggagaa ggagaaggga cggagctcga tattgccttc   2160
ccgagccctg tcggcgtgaa acgcctgtta gcagcatttg ctcctattga aaagcagtaa   2220
```

<210> SEQ ID NO 23
<211> LENGTH: 2526
<212> TYPE: DNA
<213> ORGANISM: Bacillus subtilis

<400> SEQUENCE: 23

```
atgcttggaa ttttaaataa aatgtttgat ccaacaaaac gtacgctgaa tagatacgaa     60
aaaattgcta acgatattga tgcgattcgc ggagactatg aaaatctctc tgacgacgcg    120
```

```
ttgaaacata aaacaattga atttaaagag cgccttgaaa aagggcgac aacggatgat    180 cttcttgttg aagctttcgc tgttgttcga gaagcttcac gccgcgtaac aggcatgttt    240
ccgtttaaag tccagctcat gggggggcgtg gcgcttcatg acggaaatat cgcggaaatg    300
aaaacagggg aagggaaaac attaacgtct actctgcctg tttatttaaa tgcgttaaca    360
ggtaaaggcg tacacatcgt gactgtcaac gaatacttgg caagccgtga cgctgagcaa    420
atggggaaaa ttttcgagtt tctcggtttg actgtcggtt tgaatttaaa ctcaatgtca    480
aaagacgaaa aagggaagc ttatgccgct gatattactt actccacaaa caacgagctt    540
ggcttcgact atttgcgtga caatatggtt ctttataaag agcagatggt tcagcgcccg    600
cttcattttg cggtaataga tgaagttgac tctatttaa ttgatgaagc gagaacaccg    660
cttatcattt ctggacaagc tgcaaaatcc actaagctgt acgtacaggc aaatgctttt    720
gtccgcacgt taaaagcgga gaaggattac acgtacgata tcaaaacaaa agctgtacag    780
cttactgaag aaggaatgac gaaggcggaa aaagcgttcg gcatcgataa cctctttgat    840
gtgaagcatg tcgcgctcaa ccaccatatc aaccaggcct taaaagctca cgttgcgatg    900
caaaaggacg ttgactatgt agtggaagac ggacaggttg ttattgttga ttccttcacg    960
ggacgtctga tgaaaggccg ccgctacagt gaggggcttc accaagcgat tgaagcaaag    1020
gaagggcttg agattcaaaa cgaaagcatg accttggcga cgattacgtt ccaaaactac    1080
ttccgaatgt acgaaaaact tgccggtatg acgggtacag ctaagacaga ggaagaagaa    1140
ttccgcaaca tctacaacat gcaggttgtc acgatcccta ccaacaggcc tgttgtccgt    1200
gatgaccgcc cggatttaat ttaccgcacg atggaaggaa agtttaaggc agttgcggag    1260
gatgtcgcac agcgttacat gacgggacag cctgttctag tcggtacggt tgccgttgaa    1320
acatctgaat tgatttctaa gctgcttaaa aacaaaggaa ttccgcatca agtgttaaat    1380
gccaaaaacc atgaacgtga agcgcagatc attgaagagg ccggccaaaa aggcgcagtt    1440
acgattgcga ctaacatggc ggggcgcgga acggacatta agcttggcga aggtgtaaaa    1500
gagcttggcg ggctcgctgt agtcggaaca gaacgacatg aatcacgccg gattgacaat    1560
cagcttcgag gtcgttccgg acgtcaggga gacccgggga ttactcaatt ttatcttct    1620 atggaagatg aattgatgcg cagattcgga gctgagcgga caatggcgat gcttgaccgc    1680
ttcggcatgg acgactctac tccaatccaa agcaaaatgg tatctcgcgc ggttgaatcg    1740
tctcaaaaac gcgtcgaagg caataacttc gattcgcgta aacagcttct gcaatatgat    1800
gatgttctcc gccagcagcg tgaggtcatt tataagcagc gctttgaagt cattgactct    1860
gaaaacctgc gtgaaatcgt tgaaatatg atcaagtctt ctctcgaacg cgcaattgca    1920
gcctatacgc aagagaaga gcttcctgag gagtggaagc ttgacggtct agttgatctt    1980
atcaacacaa cttatcttga tgaaggtgca cttgagaaga gcgatatctt cggcaaagaa    2040
ccggatgaaa tgcttgagct cattatggat cgcatcatca aaatataaa tgagaaggaa    2100 gagcaattcg gcaaagagca aatgcgcgaa ttcgaaaaag ttatcgttct tcgtgccgtt    2160
gattctaaat ggatggatca tattgatgcg atggatcagc tccgccaagg gattcacctt    2220
cgtgcttacg cgcagacgaa cccgcttcgt gagtatcaaa tggaaggttt tgcgatgttt    2280
gagcatatga ttgaatcaat tgaggacgaa gtcgcaaaat ttgtgatgaa agctgagatt    2340
gaaaacaatc tggagcgtga agaggttgta caaggtcaaa caacagctca tcagccgcaa    2400
gaaggcgacg ataacaaaaa agcaaagaaa gcaccggttc gcaaagtggt tgatatcgga    2460
```

| | |
|---|---|
| cgaaatgccc catgccactg cggaagcggg aaaaaatata aaaattgctg cggccgtact | 2520 |
| gaatag | 2526 |

<210> SEQ ID NO 24
<211> LENGTH: 1095
<212> TYPE: DNA
<213> ORGANISM: Bacillus subtilis

<400> SEQUENCE: 24

| | |
|---|---|
| atgaagagac gattagtatt ggaaaacgga gcggtattcg agggagaagc cttcggaagc | 60 |
| ttagaacaca acatgggaga agtcgttttt aatactggga tgacaggcta tcaggaaatt | 120 |
| ttatctgacc cttcttactg cggacagatc gtaacattaa catcccgct tatcggaaat | 180 |
| tacggcatta accgtgatga ttttgaatcc attacccctt ttgtgaaagg gctgatcatc | 240 |
| aaagaattat gtgagctgcc ttccaactgg cgttcagcat acaccttaga cgagtattta | 300 |
| aaaataaaaa acattcccgg actccagggg attgatacaa ggaagctgac aagaatgatc | 360 |
| cgcacggcag gcgcgctaaa aggaacattc gcttcatctg atgaagatat cgaagcagtg | 420 |
| ctgaaaagac tgaacgaaac ggaattgcca agaaatcaag tatcccaagt atcagccaaa | 480 |
| acagcatatc cgagcccggg aagaggcaaa cgcattgtct tggttgactt cggcacgaaa | 540 |
| cacgggattc taagagagct gaacaaacgg aaatgtgacg tcatcgttgt gccttacaac | 600 |
| attacagcgg aagaggtgct tcagctgaaa ccggacggta tcatgctttc taacggacct | 660 |
| ggagacccga aggatgtgcc tgaagcgatt gaaatgatta aggtgttct tggaaaagtg | 720 |
| ccattattcg gaatatgtct cggccaccaa ttattcgcgc tggcgtgcgg ggcgaatact | 780 |
| gaaaaaatga attcggcca caggggctca accacccgg taaaagagct ggctacagga | 840 |
| aaagttgcct taacatctca aaaccatgga tatacagttt cgtctatcag taaaacagaa | 900 |
| ctggaagtga cgcatatcgc aattaacgac gatacgattg aagggctgaa gcataaaaca | 960 |
| ttgccggcat ttacggttca atatcatccc gaagcctcac ctggtcctga ggatgccaac | 1020 |
| catctatttg acagattcat cgaaatgatc gaaacaacag agaagaagg ggaagcggta | 1080 |
| tgccaaaacg cgtag | 1095 |

<210> SEQ ID NO 25
<211> LENGTH: 1047
<212> TYPE: DNA
<213> ORGANISM: Bacillus subtilis

<400> SEQUENCE: 25

| | |
|---|---|
| atgagtgatc gtcaggcagc cttagatatg gctcttaaac aaatagaaaa acagttcggc | 60 |
| aaaggttcca ttatgaaact gggagaaaag acagatacaa gaatttctac tgtaccaagc | 120 |
| ggctccctcg ctcttgatac agcactggga attggcggat atcctcgcgg acggattatt | 180 |
| gaagtatacg gtcctgaaag ctcaggtaaa acaactgtgg cgcttcatgc gattgctgaa | 240 |
| gttcagcagc agggcggaca agccgcgttt atcgatgcgg agcatgcgtt agatccggta | 300 |
| tacgcgcaaa agctcggtgt taacatcgaa gagcttttac tgtctcagcc tgacacaggc | 360 |
| gagcaggcgc ttgaaattgc ggaagcattg gttcgaagcg gggcagttga cattgtcgtt | 420 |
| gtcgactctg tagccgctct cgttccgaaa gcggaaattg aaggcgacat gggagattcg | 480 |
| catgtcggtt tacaagcacg cttaatgtct caagcgcttc gtaagctttc aggggccatt | 540 |
| aacaaatcga agacaatcgc gatttcatt aaccaaattc gtgaaaaagt cggtgttatg | 600 |
| ttcgggaacc cggaaacaac acctggcggc cgtgcgttga aattctattc ttccgtgcgt | 660 |

```
cttgaagtgc gccgtgctga acagctgaaa caaggcaacg acgtaatggg gaacaaaacg      720
aaaatcaaag tcgtgaaaaa caaggtggct ccgccgttcc gtacagccga ggttgacatt      780
atgtacggag aaggcatttc aaaagaaggc gaaatcattg atctaggaac tgaacttgat      840
atcgtgcaaa aagcggttc atggtactct tatgaagaag agcgtcttgg ccaaggccgt       900
gaaaatgcaa acaattcct gaaagaaaat aaagatatca tgctgatgat ccaggagcaa       960
attcgcgaac attacggctt ggataataac ggagtagtgc agcagcaagc tgaagagaca     1020
caagaagaac tcgaatttga agaataa                                          1047
```

<210> SEQ ID NO 26
<211> LENGTH: 1836
<212> TYPE: DNA
<213> ORGANISM: Bacillus subtilis

<400> SEQUENCE: 26

```
gtgagtaaag ttatcggaat cgacttagga acaacaaact catgtgtggc agtgcttgaa       60
ggcggcgagc ctaaagttat tgctaacgct gaaggaaacc gcacaacgcc atcagttgtt      120
gcatttaaaa acggcgaacg tcaagtaggg gaagtggcta acgccaatc tattacaaac       180 cctaacacaa ttatgtctat caaacgtcat atgggtactg attataaagt tgaaattgaa      240
ggaaaggatt acactccaca agaagtgtct gctatcatcc ttcaacacct taaatcatac      300
gctgaaagct atcttggcga aacagtatca aaagcagtta tcacagttcc agcatacttt      360
aacgatgctg agcgtcaagc tacaaaagac gctggtaaaa ttgcaggtct tgaagtagaa      420
cgtatcatca acgagccgac tgcagcagcg cttgcatacg acttgataa acagatgaa       480 gatcaaacga tcctagtata cgaccttggc ggcggtacat tcgacgtttc catccttgag      540
cttggcgacg gtgtattcga agttcgttca actgccggcg acaaccgtct gggcggggac      600
gattttgacc aagttatcat cgatcatctt gtgtctgaat tcaaaaaaga aaacggcatt      660
gatttgtcaa aagacaaaat ggcgcttcag cgtttgaaag acgcagctga aaaagcgaaa      720
aaagatcttt ccggcgtatc ttctacgcaa atttctttac cgtttatcac agctggagaa      780
gcaggaccgc ttcaccttga acttacatta acacgcgcta aattcgaaga gctttcttct      840
catttagtag agcgcacaat gggtcctgtc cgtcaagcgc ttcaagatgc aggacttttct     900 gcaagcgaaa tcgacaaagt catccttgtc ggcggatcaa ctcgtatccc tgccgtacaa     960
gaagcaatca aaaagaaac tggaaaagaa gcgcataaag gcgtaaaccc ggatgaagtt     1020
gtagcgcttg gtgctgcgat tcagggcggc gttatcacag gtgacgtaaa agatgttgtt     1080
cttcttgacg ttacaccgct ttctctcggt atcgaaacaa tgggcggcgt gtttacaaaa     1140
ctgatcgacc gcaacacgac gatcccgaca agcaaatctc aagtgttctc aactgctgct     1200
gataaccaaa cagctgttga tatccatgtt cttcaaggtg agcgcccaat gtctgccgac     1260
aacaaaacac tcgccgcctt ccagcttact gatatcccgc cagcaccgcg cggcgtgcct     1320
caaatcgaag tttctttcga tattgacaaa aacggtatcg taaacgtaag agcaaaagac     1380
ttaggcacag ggaagaaca aaacattaca atcaaatctt cttcaggtct ttcagatgaa     1440
gagatcgaac gcatggtaaa agaagcggaa gaaaatgctg acgctgatgc gaagaaaaaa     1500
gaagaaatcg aagtccgcaa cgaagcagat cagcttgttt tccaaactga gaaaacatta     1560
aaagatcttg aaggcaaagt agacgaagaa caagtgaaaa agccaacga tgccaaagat     1620 gctttaaaag cagcgattga gaaaaacgaa tttgaagaga tcaaagcgaa aaagatgag      1680
```

```
cttcaaacaa tcgttcaaga gctttctatg aagctttatg aagaagctgc taaagcacag    1740
caagctcaag gcggagcaaa cgctgaaggc aaagcggatg acaacgttgt cgacgctgaa    1800
tacgaagaag taaacgacga ccaaaacaaa aaataa                              1836

<210> SEQ ID NO 27
<211> LENGTH: 1632
<212> TYPE: DNA
<213> ORGANISM: Bacillus subtilis

<400> SEQUENCE: 27
atggcaaaag aaattaagtt tagtgaagaa gctcgccgcg caatgcttcg cggtgtcgat      60
gcacttgctg atgctgttaa agtaaccttta ggaccaaaag acgcaacgt ggttctagag     120 aaaaaattcg gttctccgtt aatcacaaat gacggtgtaa caatcgctaa agaaatcgag     180
ctagaagacg cgtttgaaaa catgggtgct aagcttgttg ctgaagtagc cagcaaaaca     240
aacgacgttg ccggtgacgg tacaacaact gcaacagttc ttgcgcaagc aatgatccgt     300
gaaggcctta aaacgtaac agcaggcgct aaccctgtag gcgtgcgtaa agggatggaa     360
caagctgtag cggttgcgat cgaaaactta aagaaatttt ctaagccaat cgaaggcaaa     420
gagtctatcg ctcaggttgc tgcgatctct gctgctgatg aggaagtcgg aagccttatc     480
gctgaagcaa tggagcgcgt aggaaacgac ggcgttatca aatcgaaga gtctaaaggc     540 ttcacaactg agcttgaagt tgttgaaggt atgcaattcg accgcggata tgcgtctcct     600
tacatggtaa ctgactctga taagatggaa gcggttcttg acaatcctta catcttaatc     660
acagacaaaa aaatcacaaa cattcaagaa atccttcctg tgcttgagca ggttgttcag     720
caaggcaaac cattgcttct gatcgctgag gatgttgaag gcgaagcact tgctacactt     780
gttgtgaaca aacttcgcgg cacattcaac gcagttgctg ttaaagctcc tggcttcggt     840
gaccgccgta agcaatgct tgaagacatc gctgtcctta ctggcggaga agtcatcaca     900
gaagatcttg gccttgacct gaaatctact caaatcgctc aattgggacg cgcttctaaa     960
gttgtcgtta ctaaagaaaa cacaacaatc gttgaaggcg ctggcgaaac agacaaaatt    1020
tctgcccgcg tgactcaaat ccgcgctcaa gtggaagaaa caacttctga attcgacaga    1080
gaaaaattac aagagcgtct tgctaaactt gctggcggcg tagctgtcat caaagtcggt    1140
gctgcgactg aaactgaact gaaagagcgt aaacttcgca tcgaagacgc cctgaactca    1200
actcgcgcag ctgttgaaga aggcatcgta tccggtggtg gtacagcgct tgtaaacgta    1260
tataacaaag tcgctgcagt tgaagctgaa ggcgatgctc aaacaggtat caacatcgtg    1320
cttcgcgcgc ttgaagagcc aatccgtcaa atcgcacaca tgctggtct gaaggatct    1380 gtcatcgttg aacgcctcaa aaacgaagaa atcggcgtag gcttcaacgc tgcaactggc    1440
gaatgggtaa acatgatcga aaaaggtatc gttgacccaa cgaaagttac acgctcagct    1500
cttcaaaacg ctgcgtctgt agctgcaatg ttcttaacaa ctgaagccgt tgtcgctgac    1560
aagccagaag aaaacgctgg cggcggaatg cctgatatgg gcggcatggg cggtatgggc    1620
ggaatgatgt aa                                                        1632

<210> SEQ ID NO 28
<211> LENGTH: 1422
<212> TYPE: DNA
<213> ORGANISM: Bacillus subtilis

<400> SEQUENCE: 28
atgaagaaag gacgcgttag ccaggtatta ggaccggtcg tcgacgtgcg ttttgaagac      60
```

```
ggtcacttgc ctgaaattta taatgcgatt aaaatttcac agccagctgc aagtgaaaac      120
gaagtaggta ttgatttaac gcttgaggtc gctcttcatt taggtgatga tacagtccgt      180
acaatcgcaa tggcatctac ggatggtgtt cagcgcggta tggaagctgt agatacagga      240
gcgccaatct cagtaccggt tggtgatgta acacttggac gtgtatttaa cgttctcgga      300
gaaaatattg atttgaatga gccggttcct gcggatgcga aaaggatcc gattcacaga       360 caggcgcctt cattcgatca gctttcaaca gaagttgaaa ttcttgaaac aggtattaaa      420
gttgttgatt tgcttgctcc ttacattaag ggcggtaaaa tcggattgtt cggtggtgcc      480
ggtgtaggta aaaccgtatt aatccaggaa ttaatcaaca acatcgcgca agagcacggc      540
ggtatctctg tattcgccgg cgtaggagag cgtactcgtg aagggaacga cctttctac      600 gaaatgagtg actctggcgt aatcaacaaa acagccatgg tattcggaca aatgaacgag      660
ccgccgggcg cacgtatgcg tgttgctttg acaggcctta caatggctga gcacttccgt      720
gatgtacaag gacaggacgt actgttcttc atcgataaca ttttccgttt cacacaagcg      780
ggttcagagg tttcagccct tcttggccgt atgccttcag cggttggtta tcagccgacg      840
cttgcaactg agatgggtca gctccaagag cgtatcacgt ctacgaacgt tggatcagtt      900
acatctatcc aggcgatcta cgtgcctgcc gatgactaca ctgacccggc gccggcgaca      960
acgttcgctc acttggatgc gacaacaaac cttgagcgta aattaactga aatgggtatt     1020
taccctgcgg ttgatccgtt ggcatctaca tcacgcgccc ttgctcctga aattgtcgga     1080
gaagagcatt atgcagttgc gcgtgaagta cagtcaacgc ttcagcgtta caaagagctt     1140
caagatatca ttgcgattct cggtatggat gaattaggcg aggaagacaa acttgtcgtt     1200
caccgcgcac gccgtatcca gttcttcctt tctcagaact tccacgtggc tgaacagttc     1260
actggacaaa aaggttctta cgtgcctgta aaagagacgg tacaaggctt caaagaaatc     1320
ttagccggta aatacgacca tcttccagaa gatgcgttcc gtcttgtagg ccgtatcgaa     1380
gaagttgttg agaaagcaaa agaaatgggt gtagaagttt aa                        1422

<210> SEQ ID NO 29
<211> LENGTH: 1116
<212> TYPE: DNA
<213> ORGANISM: Bacillus subtilis

<400> SEQUENCE: 29
atggctgata acaaaccca cgagacagaa ttaacattcg accaagtaaa agagcaatta       60
acagagtctg gtaaaaaacg tggcgttttg acatatgaag aaattgctga gcgtatgtcc      120
agctttgaaa ttgaatcaga ccaaatggat gagtattatg aattttttagg tgaacaaggt     180 gttgaattaa ttagtgagaa tgaagaaaca gaagatccta atattcagca gcttgccaaa     240
gccgaagaag aatttgacct taatgaccta agtgtaccgc ctggcgttaa aatcaatgac     300
ccagttcgta tgtatttaaa ggaaatcggt cgggttaacc ttctttctgc aaaagaagaa     360
atcgcctacg ctcaaaagat tgaagaaggt gacgaagaat ctaaacgcag attggctgaa     420
gcgaacctgc ggcttgttgt cagtatcgca aaacggtatg tcggacgcgg tatgctgttc     480
cttgatctga tccaggaagg aaacatgggc ctgatgaaag ccgttgaaaa atttgattat     540
cgcaaaggtt ataaattcag tacgtatgct acgtggtgga tcagacaggc gattacacgc     600
gccattgccg atcaggcgag aacgatccgg attcccgttc atatggttga aaccattaat     660
aaattaatcc gtgtgcagcg tcaattactg caagacttag gcagagaacc aacacctgaa     720
```

| | |
|---|---:|
| gaaattgcgg aagatatgga tttaacgcct gaaaaagtac gcgaaatctt aaagattgct | 780 |
| caagagccgg tatctctgga aacaccgatc ggtgaagagg atgactcgca ccttggtgat | 840 |
| ttcattgaag accaagaagc aacttcacct tctgaccacg ccgcatacga gctattgaaa | 900 |
| gagcagctgg aagatgtgct tgatacgtta actgatcgtg aagaaaatgt attgcgtctt | 960 |
| cgattcggtc ttgatgacgg ccgtacaaga acattagaag aggtcggcaa agtatttgga | 1020 |
| gtaacgagag agcgtattcg acaaatcgaa gccaaagcgt tgcggaaact aagacatcct | 1080 |
| agcagaagta aacgtttgaa agatttcctt gaataa | 1116 |

```
<210> SEQ ID NO 30
<211> LENGTH: 2151
<212> TYPE: DNA
<213> ORGANISM: Bacillus subtilis

<400> SEQUENCE: 30
```

| | |
|---|---:|
| atggctaaaa tgagagtata tgaatatgca aaagcgttaa atgtttcaag taaggaaatt | 60 |
| ttgaccgcac tgaagaacat ggatttagaa gtgaataatc acatggccat gcttgaagaa | 120 |
| aaggccatta aaaagctaga tgccaaatat aaaaaaggcg gcgcagctgc taaatctcaa | 180 |
| aagccagcag atacgaacaa aaacaaacag ccacaagggg ttaatcagca atcagctgga | 240 |
| aatcaaccaa ataaaattcg agacggaaag aagaatgacg tgcagaataa tcaatttaac | 300 |
| aaaaacaaga gaataacaa caacaaaaaa ataaacgca acaacaacaa taataaaaac | 360 |
| caacatcagc aaaagcctgt aaagccgaaa aaagagcttc ctgagaaaat tacattctct | 420 |
| ggcactttaa cagttggcgc acttgctgaa gagcttggca aagagccttc agaaatcatt | 480 |
| aaaaagctga tgcttcttgg cgtaatggca accattaacc aagagcttga taagacaca | 540 |
| atcgaactca ttgcatcaga atatggtgtt gaaacagaag aggtcattgt gcttgaagaa | 600 |
| acagagctgg aaaaatacga agagcctgat aatgaagagg atcttgaaat tcgtcctcct | 660 |
| gtcgtgacaa tcatgggcca cgttgaccat gggaaaacaa cgcttcttga cagcatccgt | 720 |
| aaaacaaagg ttgttgaagg agaagcaggc ggaatcactc agcatatcgg cgcttatcaa | 780 |
| attgaagaga acggcaagaa aatcacgttc ttggatacac cgggccacgc cgcatttaca | 840 |
| acaatgcgtg cacgcggtgc agaagtaact gatattacga ttcttgtcgt agctgccgat | 900 |
| gacggtgtca tgccgcaaac agttgaagcg attaaccatg caaaagcagc agaggttcca | 960 |
| atcatcgttg ctgtgaataa aatagataaa gaatctgcaa accctgaccg tgtaatgcaa | 1020 |
| gaactgacga aatacggact tgtccctgaa gcttggggcg agaaaccat ttttgtgccg | 1080 |
| ctttccgctt taactggaaa aggcattgat gagctcgttg aaatgatttt gcttgtcagt | 1140 |
| gaggtagagg aactgaaagc gaatccgaac cgtcaggcaa aggaacggt tattgaagct | 1200 |
| gaactcgata aaggcagagg gtcagttgcg acgttgctcg tacagactgg aacactgcat | 1260 |
| gtcggtgatc cgatcgtagt cggcaataca tttggccgtg tccgtgcaat ggtcaacgac | 1320 |
| attggccgcc gtgtgaaaac tgccggcccg tcaactccgg ttgaaattac cggtttgaat | 1380 |
| gatgtccctc aagcgggaga ccaattcctt gtctttaagg atgaaaaaac agctcgttct | 1440 |
| gtcggtgaag cccgtgcttc gaaacagctt gaagagcagc gcagcgataa agcgaagctc | 1500 |
| agtcttgatg atttattcga gcaaattaag caaggtgatg taaaagacat caacctcatc | 1560 |
| gtaaaagctg acgttcaagg atctgctgaa gctttaacgg ctgcgcttca aaaaattgaa | 1620 |
| gtagaaggcg ttaaagtgaa aatcatccat acaggcgttg gtgcgattac tgaatctgac | 1680 |
| attatcttgg catctgcttc caatgcaatt gttatcgggt ttaatgtgag accggacgga | 1740 |

```
aatgctaaga gtacggctga agctgaaaat gtagatattc gacttcaccg tatcatttac    1800
aaagtaatcg acgagattga agctgccatg aaaggtatgc ttgatcctga atatgaagaa    1860
aaagtaattg gtcaagtaga agtacgccaa acattcaaag tatctaaaat cggtacaatt    1920
gccggcggat atgttactga aggaaccatt acgcgcgaca gcggcctccg tttaattcgt    1980
gatggcgtcg tcatctttga aggcgaagta gatgttctga aacgctttaa agacgatgtg    2040
aaagaagttt cacaaggcta tgaatgtggt attacaatta agaaatacaa tgacattcgt    2100
gaaggtgaca tcctagaagc gtttgtcatg caagaaattg aaagaacgtg a             2151
```

BACTERIA AND METHOD FOR IMPROVING PLANT HEALTH AND GROWTH

SEQUENCE LISTING

The instant application contains a Sequence Listing which has been submitted electronically in ASCII format and is hereby incorporated by reference in its entirety. Said ASCII copy, created on Apr. 11, 2016, is named 10457-238_SL.txt and is 65,376 bytes in size.

BACKGROUND

1. Field of the Invention

The present invention relates to bacteria and bacterial combinations which can be used in methods to improve the health and vigor, including enhancement of the growth of plants, including important crop plants, while improving the sustainability of the agro-ecosystem. The bacterial strains herein include *Paenibacillus* sp. (ATY16); *Bacillus megaterium* (PT6); *Bacillus subtilis* (PT26A); and combinations thereof, and can be useful for treatment of healthy plants and plants which are susceptible to plant disease or which have been infected with plant disease. Although the methods and compositions are useful for administration to any plant or seed, preferred plants are those which are commercial crops, for example citrus, corn, soybean, and tomato. The methods and compositions of embodiments of the invention can ameliorate the effects of plant diseases, including microbial diseases such as huanglongbing (HLB) disease (also known as citrus greening disease).

2. Description of the Related Art

Conventional pest control technologies based on the use of agricultural chemicals have contributed to efficient agricultural productivity. However, their use also has led to increasing public concerns regarding their negative impacts on the environment. Environmentally-beneficial agriculture using no or reduced amounts of agricultural chemicals and satisfying cultivation efficiency, while assuring human safety is desired and necessary. Therefore, pest and disease control technology fulfilling such demand is needed in the art.

Crops in different ecosystems around the world may suffer less than ideal conditions due to soil or weather conditions, or various stresses, as well as diseases that can negatively affect the health and vigor of the crop plants. Such factors can reduce productivity of the crops to a greater or lesser degree, even under good growing conditions. Thus, crop plants can benefit from treatment that will increase the health and vigor of the plants, whether the plants are stressed by poor conditions, by disease, or even when the plants are healthy or grown under favorable conditions.

A number of plant diseases have negative effects on crop plants worldwide. Microbial plant pathogens can lead to losses in yield, and can even kill crop plants. Therefore, strategies to improve plant defenses against pathogens are needed to improve cultivation, crop yield, and crop quality, while avoiding environmental pollution of the plants and the soil in which they are grown. Biological approaches, such as the use of beneficial bacteria as described herein, therefore are helpful to improve crop plant health generally, and to reduce the effects of plant pathogens.

An example of a harmful plant disease is HLB or citrus greening disease also sometimes referred to as yellow shoot or yellow dragon. This is a major bacterial disease of citrus crops and can be found in Asia, in the Americas and in Africa. It has been spreading worldwide, resulting in economic loss. Huanglongbing (HLB) is currently the most economically devastating disease of citrus worldwide and no established cure is available. All commercial citrus varieties currently available are susceptible to HLB and the citrus industries in affected areas have suffered a decline in both production and profit (Bové, 2006; Gottwald et al., 2007; Wang and Trivedi, 2013). In Florida, HLB is now present in all commercial citrus-producing counties and is destroying the $9 billion citrus industry at a rapid pace. It was estimated that HLB has played a key role in the loss of about 100,000 citrus acres since 2007 in Florida and has cost Florida's economy approximately $3.6 billion in lost revenues since 2006 (Gottwald, 2010; Wang and Trivedi, 2013).

Citrus HLB is associated with a phloem-limited fastidious α-proteobacterium belonging to the 'Candidatus' genus *Liberibacter*, formerly known as *Liberobacter* (Jagoueix et al., 1994). Currently, three species of 'Ca. Liberibacter' have been identified to cause HLB disease: 'Ca. L. asiaticus' (Las), 'Ca. L. africanus', and 'Ca. L. americanus' (Gottwald, 2010). These bacteria have not been cultivated in pure culture. HLB pathogen is mainly spread by the insect (psyllid) vector *Diaphorina citri* in the field. There are two psyllid species transmitting Liberibacters: Asian citrus psyllid (*Diaphorina citri*) in Asia and the Americas (Bové, 2006; Halbert, 2005; Teixeira et al., 2005) and African citrus psyllid (*Trioza erytreae*) in Africa (Bové, 2006). Las and Asian citrus psyllid are the most prevalent and important throughout HLB-affected citrus-growing areas worldwide (Bové, 2006). Las propagates in the phloem of the host plants, resulting in die-back, small leaves, yellow shoots, blotchy mottles on leaves, corky veins, malformed and discolored fruit, aborted seed, premature fruit drop, root loss, and eventually tree death (Bové, 2006; Gottwald et al., 2007; Wang and Trivedi, 2013). The life span for the profitable productivity of infected citrus trees is dramatically shortened as the disease severity increases and the yield is significantly reduced while the tree is still alive (Gottwald et al., 2007). The understanding of virulence mechanism of the bacterial pathogen is limited, due to the difficulty in culturing Las. So far, most molecular insights of the HLB biology and Las pathogenicity are derived from the genome sequences of Las and other related Liberibacters (Duan et al., 2009; Lin et al., 2011; Leonard et al., 2012; Wulff et al., 2014).

Particularly sensitive citrus includes *Citrus halimii*, 'Nules' clementine mandarin, Valencia sweet orange, 'Madam Vinous' sweet orange, 'Duncan' grapefruit, 'Ruby' red grapefruit, and 'Minneola' tangelo, however, any Citrus species is vulnerable to HLB. In addition, some related plants in the genus *Rutaceae*, and other plants may become infected with *Ca. Liberibacter* species. Those of skill in the art are able to test for infection by *Ca. Liberibacter*, and therefore are able to determine which plants suffer from HLB or *Ca. Liberibacter* infection. Treatment of such plants is considered part of this invention.

Current methods in use for HLB control include the use of HLB-free citrus seedlings, destruction of infected trees, and application of insecticides such as aldicarb (Temik®) or imidacloprid (Admire®). These insecticides are aimed at controlling psyllids, a possible insect vector for the disease, although it is not known if insecticides have a direct effect on the spread of HLB. These insecticide treatments do not reduce disease in trees already infected, in any case. An integrated control program has been recommended for HLB in commercial orchards by the United Nations Development Program, Food and Agriculture Organization (UNDP, FAO)

Southeastern Asian citrus rehabilitation project (Aubert, 1990). The program highlights controlling psyllid vectors with insecticides, reducing inoculum through removal of HLB-symptomatic trees, propagating and using pathogen-free budwood and nursery trees. In Florida, foliar nutrition programs coupled with vector control are often used to slow down the spread of HLB and reduce devastating effects of the disease (Gottwald, 2010). These control practices have shown limited effect for preventing the further spread of HLB. Other than destruction and removal of diseased trees, there is no effective control for HLB in infected trees, and there is no known cure for HLB. New and improved treatments for citrus (and other) HLB disease therefore are needed in the art.

Other plant pathogens of the greatest interest include the bacterium *Xanthomonas citri* causing citrus canker, *Xanthomonas axonopodis* pv. *citrumelo* causing citrus bacterial spot disease, and *Xylella fastidiosa* causing citrus variegated chlorosis; the pathogenic fungus *Alternaria citri* causing leaf and stem rot and spot, *Phytophthora* spp. causing foot and root rot, and *Guignardia citricarpa* causing citrus black spot, all of which can result in crop loss.

Induced resistance can confer long-lasting protection against a broad spectrum of plant diseases either locally or systemically (Durrant and Dong, 2004; Walters et al., 2013). Plant defense mechanisms can be activated by pathogens (Durrant and Dong, 2004), beneficial microorganisms (Weller et al., 2012; Zamioudis and Pieterse, 2012), or by chemical inducers (Walters et al., 2013). Overall, maximizing crop plant health and vigor has been a difficult problem with no comprehensive solution. Therefore, the embodiments of the invention described herein are provided for the control of crop pathogens such as HLB, *Xanthomonas citri* causing citrus canker, *Xanthomonas axonopodis* pv. *citrumelo* causing citrus bacterial spot disease, and *Xylella fastidiosa* causing citrus variegated chlorosis; the pathogenic fungus *Alternaria citri* causing leaf and stem rot and spot, *Phytophthora* spp. causing foot and root rot, and *Guignardia citricarpa* causing citrus black spot and to improve plant health and vigor, including germination, growth, disease resistance, and improvement of crop quality and quantity.

SUMMARY OF THE INVENTION

Techniques are provided for improving the health and disease resistance of plants, including important crop plants such as citrus, corn, soybeans, tomatoes and others. The bacterial strains according to embodiments of the invention described herein can be applied to plants to improve health and vigor, increase seed germination, increase growth, enhance crop or fruit production, and increase plant defense mechanisms. Therefore, the bacterial strains can be used to benefit any plant, including healthy plants and diseased plants. The methods described here involve application of the bacterial strains to the plant, including application to the soil around the plant by soil injection or soil drench methods, application to the surface of the plant, such as by spraying onto the plant or parts of the plant, such as by foliar spraying, or injection into the plant such as by trunk injection. Plants for which the invention is contemplated include any plant, particularly crop plants, but including ornamental plants as well.

Still other aspects, features, and advantages of embodiments of the invention are readily apparent from the following detailed description, simply by illustrating a number of particular embodiments and implementations, including the best mode contemplated for carrying out the invention. Other embodiments also are capable of other and different features and advantages, and its several details can be modified in various obvious respects, all without departing from the spirit and scope of the invention. Accordingly, the drawings and descriptions are to be regarded as illustrative in nature, not as restrictive.

It has now been found that certain bacterial strains have beneficial effects on the growth, general health and vigor, pathogenic defenses, fruit and crop productivity, fruit quality and crop quality of plants. The bacteria have benefits to the cellular health of plants and stimulate growth of the plants, even when the plants are infected with a disease, such as HLB disease. These bacterial strains can be used individually or as mixtures with other beneficial bacteria. The consortia of various compatible bacteria possessing multiple plant beneficial traits and antagonistic ability against plant pathogens may improve disease control, with broad spectrum of action and enhanced reliability and efficacy (Lugtenberg and Kamilova 2009).

Therefore, embodiments of the invention include a bacterial composition for administration to plants, which comprises a botanically compatible vehicle and at least one isolated bacterial strain selected from the group consisting of *Bacillus megaterium* PT6 having accession number PTA-122799, *Bacillus subtilis* PT26A having accession number PTA-122797, *Paenibacillus* sp. ATY16 having accession number PTA-122798. Preferably, the compositions comprise $10^3$-$10^{11}$ cfu/mL of the at least one bacterial strain or at least $10^3$ cfu/mL of the at least one bacterial strain, at least $10^5$ cfu/mL of the at least one bacterial strain, or at least $10^7$ cfu/mL of the at least one bacterial strain.

Additional embodiments of the invention include compositions as described herein wherein the at least one bacterial strain is *Bacillus megaterium* PT6 having accession number PTA-122799, wherein the at least one bacterial strain is *Bacillus subtilis* PT26A having accession number PTA-122797, or wherein the at least one bacterial strain is *Paenibacillus* sp. ATY16 having accession number PTA-122798.

Further embodiments of the invention include a composition which comprises seeds treated or coated with the composition described above in the summary of invention, and also include compositions which further comprise a plant defense inducer compound selected from the group consisting of β-aminobutyric acid (BABA) or a salt thereof, and salicylic acid (SA) or a salt thereof.

A preferred embodiment of the invention is a method of improving the health and vigor of a plant, comprising administering to the plant an effective amount of the bacterial composition described throughout the application and in paragraph 16 herein, wherein the improvement in health and vigor is one or more of: a) improved resistance to disease; b) improved ability to defend against disease; c) reduction of disease symptoms; d) faster growth; e) improved crop productivity; f) improved crop quality; g) improved seed germination; and h) improved seedling emergence. Preferably, the at least one bacterial strain is *Bacillus subtilis* PT26A having accession number PTA-122797.

In certain embodiments of the invention, the plant is a crop plant, preferably a citrus plant. The citrus advantageously can be selected from the group consisting of *Citrus maxima* (Pomelo), *Citrus medica* (Citron), *Citrus micrantha* (Papeda), *Citrus reticulata* (Mandarin orange), *Citrus paradisi* (grapefruit), *Citrus trifolata* (trifoliate orange), *Citrus japonica* (kumquat), *Citrus australasica* (Australian Finger Lime), *Citrus australis* (Australian Round lime), *Citrus glauca* (Australian Desert Lime), *Citrus garrawayae*

(Mount White Lime), *Citrus gracilis* (Kakadu Lime or Humpty Doo Lime), *Citrus inodora* (Russel River Lime), *Citrus warburgiana* (New Guinea Wild Lime), *Citrus wintersii* (Brown River Finger Lime), *Citrus halimii* (limau kadangsa, limau kedut kera) *Citrus indica* (Indian wild orange), *Citrus macroptera*, and *Citrus latipes, Citrus x aurantiifolia* (Key lime), *Citrus x aurantium* (Bitter orange), *Citrus x latifolia* (Persian lime), *Citrus x limon* (Lemon), *Citrus x limonia* (Rangpur), *Citrus x sinensis* (Sweet orange), *Citrus x tangerina* (Tangerine), Imperial lemon, tangelo, orangelo, tangor, kinnow, kiyomi, Minneola tangelo, oroblanco, sweet orange, ugli, Buddha's hand, citron, lemon, orange, bergamot orange, bitter orange, blood orange, calamondin, clementine, grapefruit, Meyer lemon, Rangpur, tangerine, and yuzu.

In the method embodiments for citrus, preferably the at least one isolated bacterial strain is selected from the group consisting of *Bacillus megaterium* PT6 having accession number PTA-122799, *Bacillus subtilis* PT26A having accession number Pta-122797, *Paenibacillus* sp. ATY16 having accession number PTA-122798, or any combination thereof.

In certain embodiments of the invention, the crop plant is selected from the group consisting of almond, apple, banana, cacao, carrot, cassava, chili, citrus, coconut, coffee, corn, cotton, cucumber, grape, legume, lettuce, mango, olive, onion, palm, peach, peanut, potato, rapeseed, rice, rubber, soybean, strawberry, sugar beet, sugar cane, sunflower, sweet potato, tea, tomato, walnut, wheat, and yam. Preferably, the crop plant is selected from the group consisting of corn, soybean, and tomato. In another embodiment, preferably the at least one isolated bacterial strain is selected from the group consisting of *Bacillus subtilis* PT26A having accession number PTA-122797.

In certain method embodiments of the invention, the plant is healthy. In other method embodiments, the plant is affected by a plant disease or plant disease symptoms. The disease can be a bacterial disease or a fungal disease, and can be selected from the group consisting of huanglongbing (HLB) disease, Fusarium, Phytophthora, citrus canker disease, citrus bacterial spot disease, citrus variegated chlorosis, citrus food and root rot, citrus and black spot disease.

In some embodiments of the invention, the administering to the plant is by a method selected from the group consisting of soil injection, soil drenching, application to seed, and foliar spraying. These methods of administering to the plant preferably provide at least $10^2$ cfu or at least $10^3$ cfu of the isolated bacterial strain per gram of plant root thirty days after administration.

Additional embodiments of the invention include a method of improving seed germination in a plant, the method comprising administering to the seed of the plant a composition as described above and a method of enhancing growth of a plant, the method comprising administering to the plant a composition as described above. A highly preferred method is a method of treating a plant disease in a plant in need thereof, which comprises administering to the soil within a ten foot radius surrounding the plant a composition as described above. Preferably, the plant is a Citrus plant and the disease is huanglongbing (HLB) disease.

Additionally, the method can further comprise administering to the plant a plant defense inducer compound selected from the group consisting of β-aminobutyric acid (BABA) or a salt thereof, and salicylic acid (SA) or a salt thereof.

In another embodiment, provided is a container that includes a housing with a composition including a botanically compatible vehicle and at least one isolated bacterial strain selected from the group consisting of *Bacillus megaterium* PT6 having accession number PTA-122799, *Bacillus subtilis* PT26A having accession number PTA-122797, *Paenibacillus* sp. ATY16 having accession number PTA-122798 disposed within the housing. The container may further include a mechanism of administration associated with the housing. The mechanism of administration may include, for example, a conduit in fluid communication with the housing and a spray nozzle in fluid communication with the conduit. The container may further include an access port for accessing the composition. Examples of suitable containers include, but are not limited to, a bin, a bucket, a barrel, a box, and the like.

BRIEF DESCRIPTION OF THE DRAWINGS

Certain embodiments are illustrated by way of example, and not by way of limitation, in the figures of the accompanying drawings.

FIG. 4A is a three-panel fluorescent photomicrograph of green fluorescent protein-expressing bacteria (strains A63, A53, 108 and 95) as indicated at five months after bacterial inoculation on grapefruit seedling roots.

FIG. 4B is a graph showing the cfu of bacteria versus time for the indicated strains.

FIG. 4C is a graph showing the cfu of bacteria versus time for the indicated strains.

DETAILED DESCRIPTION OF THE INVENTION

1. Introduction

Figure 1:
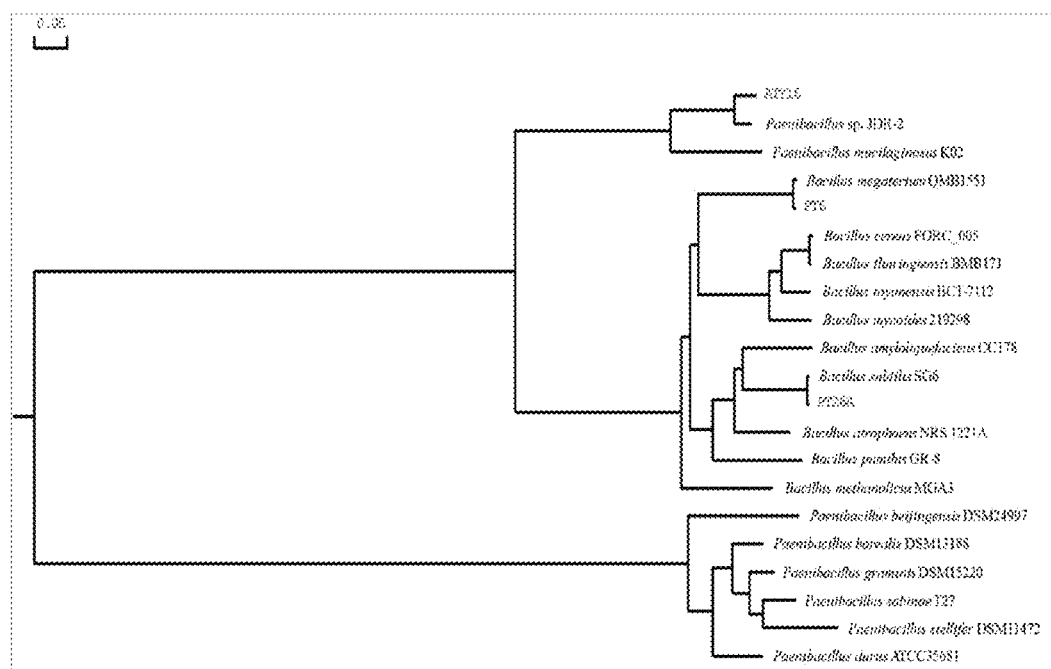
FIG. 1 is a maximum likelihood phylogenetic tree showing the relationships of bacterial strains ATY16, PT6, and PT26A to other fully sequenced *Bacillus* and *Paenibacillus* species. The phylogenic tree was constructed using DNA sequences of nine housekeeping genes (uvrD, secA, carA, recA, groEL, dnaK, atpD, gyrB and infB) aligned using the maximum likelihood method. Horizontal scale bar (0.05) at the top represents the number of nucleotide substitutions per site.

The invention is described herein with reference to specific embodiments. However, various modifications and changes can be made to the invention without departing from its broader spirit and scope. The specification and drawings therefore are to be regarded as illustrative rather than restrictive. Throughout this specification and the claims, unless the context requires otherwise, the word "comprise" and its variations, such as "comprises" and "comprising," are used to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

In this study, the effects of various bacterial strains and combinations of bacterial strains, were evaluated for activation of natural plant defense mechanisms and for improvements in health and growth of the plants. The bacterial strains improve plant defenses against disease, with the effect of increasing the health and growth of plants. Therefore, this approach can be used to treat, for example, plants that have been infected with, plants that are susceptible to infection with, or plants that exhibit symptoms of HLB disease or infection with a *Candidatus liberibacter* species. Examples of such species include *Candidatus liberibacter asiaticus, Candidatus liberibacter americanus, Candidatus liberibacter africanus*, and any combination thereof.

While a number of embodiments of the present invention have been shown and described herein in the present context, such embodiments are provided by way of example only, and not of limitation. Numerous variations, changes and substitutions will occur to those of skill in the art without materially departing from the invention herein. Any means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

2. Definitions

All technical and scientific terms used herein, unless defined herein, are intended to have the same meaning as commonly understood by one of ordinary skill in the art. The techniques employed herein are also those that are known to one of ordinary skill in the art, unless stated otherwise.

The term "applying," "application," "administering," "administration," and all their cognates, as used herein, refers to any method for contacting the plant with the bacteria and bacterial compositions discussed herein. Administration generally is achieved by application of the bacteria, in a vehicle compatible with the plant to be treated (i.e., a botanically compatible vehicle or carrier), such as an aqueous vehicle, to the plant or to the soil surrounding the plant. Any application means can be used, however preferred application is to the soil surrounding the plant, by injection, soaking or spraying, so that the applied bacteria preferably come into contact with the plant roots and can colonize the roots.

The term "bacteria," as used herein, refers to any prokaryotic microorganism, and is intended to include both Gram positive and Gram negative bacteria, and unclassified bacteria. The term "beneficial bacteria," as used herein, refers to the bacteria of strains PT6, PT26A and ATY16, described herein and deposited in the ATCC under accession numbers PTA-122799, PTA-122797 and PTA-122798, respectively, in accordance with the requirements of the Budapest Treaty. Further, strains that have at least 99% identity to the 16s rRNA of these deposited strains are considered "genetic equivalents" of the specific deposited strains. In addition, or alternatively, strains possessing at least 99% identity to at least 2, at least 3, at least 4, at least 5, or all of the uvrD, secA, carA, recA, groEL, dnaK, atpD, gyrB and infB genes of the deposited strains are considered "genetic equivalents" of the deposited strains. See the sequence information for these genes, provided below. In embodiments described and/or claimed herein, genetic equivalents may be used as an alternative in place of beneficial bacteria.

The bacterial strains PT6, PT26A and ATY16 initially were isolated from plants in the St. Lucie County School District, Florida. The genome size of ATY16 is 6,788,192 bp with 50.79% GC. The genome size of PT6 is 5,485,792 bp with 37.76% GC. The genome size of PT26A is 4,360,593 bp with 43.23% GC. At a 16s level, the rRNA of the strains is 99% identical to the deposit of *Bacillus megaterium* PT6 having accession number PTA-122799, *Bacillus subtilis* PT26A having accession number PTA-122797, *Paenibacillus* sp. ATY16 having accession number PTA-122798.

The term "botanically acceptable carrier/vehicle" or "botanically compatible carrier/vehicle," as used herein, refers to any non-naturally occurring vehicle, in liquid, solid or gaseous form which is compatible with use on a living plant and is convenient to contain a substance or substances for application of the substance or substances to the plant, its leaves or root system, its seeds, the soil surrounding the plant, or for injection into the trunk, or any known method of application of a compound to a living plant, preferably a crop plant, for example a citrus tree, or corn, soybean or tomato plant. Useful vehicles can include any known in the art, for example liquid vehicles, including aqueous vehicles, such as water, solid vehicles such as powders, granules or dusts, or gaseous vehicles such as air or vapor. Any vehicle which can be used with known devices for soaking, drenching, injecting into the soil or the plant, spraying, dusting, or any known method for applying a compound to a plant, is contemplated for use with embodiments of the invention. Typical carriers and vehicles contain inert ingredients such as fillers, bulking agents, buffers, preservatives, anti-caking agents, pH modifiers, surfactants, soil wetting agents, adjuvants, and the like. Suitable carriers and vehicles within this definition also can contain additional active ingredients such as plant defense inducer compounds, nutritional elements, fertilizers, pesticides, and the like. In a particular embodiment, the botanically acceptable vehicle pertains to a vehicle component, or vehicle formulation, that is not found in nature. In another embodiment, the botanically acceptable vehicle may pertain to a vehicle found in nature, but where the vehicle and the bacteria strain(s) are not mixed or combined together in nature.

The term "Citrus" or "citrus," as used herein, refers to any plant of the genus *Citrus*, family Rutaceae, and includes *Citrus maxima* (Pomelo), *Citrus medica* (Citron), *Citrus nzicrantha* (Papeda), *Citrus reticulata* (Mandarin orange), *Citrus trifolata* (trifoliate orange), *Citrus japonica* (kumquat), *Citrus australasica* (Australian Finger Lime), *Citrus australis* (Australian Round lime), *Citrus glauca* (Australian Desert Lime), *Citrus garrawayae* (Mount White Lime), *Citrus gracilis* (Kakadu Lime or Humpty Doo Lime), *Citrus inodora* (Russel River Lime), *Citrus warburgiana* (New Guinea Wild Lime), *Citrus wintersii* (Brown River Finger Lime), *Citrus halimii* (limau kadangsa, limau kedut kera) *Citrus indica* (Indian wild orange), *Citrus macroptera*, and *Citrus latipes*. Hybrids also are included in this definition, for example *Citrus x aurantiifolia* (Key lime), *Citrus x aurantium* (Bitter orange), *Citrus x latifolia* (Persian lime), *Citrus x limon* (Lemon), *Citrus x limonia* (Rangpur), *Citrus x paradisi* (Grapefruit), *Citrus x sinensis* (Sweet orange), *Citrus x tangerina* (Tangerine), *Poncirus trifoliata x C. sinensis* (Carrizo citrange), *C. paradisi* "Duncan" grapefruit x *Pondirus trifoliate* (Swingle citrumelo), and any other known species or hybrid of genus Citrus. Citrus known by their common names include, Imperial lemon, tangelo, orangelo, tangor, kinnow, kiyomi, Minneola tangelo, oroblanco, sweet orange, ugh, Buddha's hand, citron, lemon, orange, bergamot orange, bitter orange, blood orange, calamondin, clementine, grapefruit, Meyer lemon, Rangpur, tangerine, and yuzu, and these also are included in the definition of citrus or Citrus.

The term "crop plant," as used herein, includes any cultivated plant grown for food, feed, fiber, biofuel, medicine, or other uses. Such plants include, but are not limited to, citrus, corn, soybean, tomato, sugar cane, strawberry, wheat, rice, cassava, potato, cotton, and the like. The term "crop," as used herein, refers to any of the food (including fruits or juice), feed, fiber, biofuel, or medicine derived from a crop plant. All crop plants are contemplated for use with the invention, including monocots and dicots.

The term "effective amount" or "therapeutically effective amount," as used herein, means any amount of the bacterial strain, combination of bacterial strains or composition containing the bacterial strains, which improves health, growth or productivity of the plant, or which reduces the effects, titer or symptoms of the plant disease, or prevents worsening of the plant disease, symptoms or infection of the plant. This term includes an amount effective to increase seed germination of a plant or a plant population, to increase the speed of seed germination of a plant or a plant population, to increase growth rates of a plant or a plant population, to increase crop yield of a plant or plant population, increase crop quality in a plant or plant population, reduce the plant pathogen titer, to inhibit plant pathogen growth, to reduce the percent of infected plants in a plant population, to reduce the percent of plants showing disease symptoms in a plant or plant population, to reduce the disease symptom severity rating or damage rating of a plant or plant population, to reduce average pathogen population or titer in a plant or plant population by about 2%, about 5%, about 10%, about 20%, about 30%, about 40%, about 50%, about 60%, about 70%, about 75%, about 80%, about 85%, about 90%, or more, compared to plants or a plant population not treated with the active ingredient.

The term "faster growth," as used herein, refers to a measurable increase in the rate of growth of a plant, including seedlings, stems, roots, seeds, flowers, fruits, leaves and shoots thereof.

The term "health," as used herein, refers to the absence of illness and a state of well-being and fitness, and refers to the level of functional or metabolic efficiency of the plant, including the ability to adapt to conditions and to combat disease, while maintaining growth and development. The term "vigor," as used herein, refers to the health, vitality and hardiness of a plant, and its capacity for natural growth and survival. Therefore, the phrase "health and vigor of a plant," as used herein, means the absence of illness, a high level of functional or metabolic efficiency, the ability to combat disease, and the maintenance of good growth and development, and the efficient production of crops.

The term "healthy," as used herein, refers to a plant or plant population which is not known currently to be affected by a plant disease.

The term "Huanglongbing disease," as used herein, is a disease of plants caused by microorganisms of the *Candidatus* genus *Liberibacter*, such as *L. asiaticus, L. africanus*, and *L. americanus*. This disease, for example, can be found in citrus plants, or other plants in the genus *Rutaceae*. Symptoms of Huanglongbing disease include one or more of yellow shoots and mottling of the plant leaves, occasionally with thickening of the leaves, reduced fruit size, fruit greening, premature dropping of fruit from the plant, low fruit soluble acid content, fruit with a bitter or salty taste, or death of the plant. The term "treating" or "treatment," or its cognates, as used herein indicates any process or method which cures, diminishes, ameliorates, or slows the progress of the disease or disease symptoms. Thus, treatment includes reducing bacterial titer in plant tissues or appearance of disease symptoms relative to controls which have not undergone treatment.

The term "improved ability to defend against disease," as used herein, refers to a measurable increase in plant defense against a disease. This can be measured in terms of a measurable decrease in disease symptoms, pathogen titer, or loss of crop yield and/or quality, or a measurable increase in growth, crop quantity or quality.

The term "improved crop productivity," as used herein, refers to a measurable increase in the quantity of a crop in a plant or a population of plants, in terms of numbers, size, or weight of crop seeds, fruits, vegetable matter, fiber, grain, and the like.

The term "improved crop quality," as used herein, refers to a measurable increase in the quality of a crop, in terms of numbers, size, or weight of crop seeds, fruits, vegetable matter, fiber, grain, and the like, or in terms of sugar content, juice content, unblemished appearance, color, and/or taste.

The term "improved resistance to disease," as used herein, refers to an increase of plant defense in a healthy plant or a decrease in disease severity in a plant or in a population of plants, or in the number of diseased plants in a plant population.

The term "improved seed germination," as used herein, means a measurable increase of the chance of successful germination of an individual seed, a measurable increase in the percentage of seeds successfully germinating, and/or a measurable increase in the speed of germination.

The term "improved seedling emergence," as used herein means a measurable increase in the speed of growth and/or development of successfully germinated individual seeds or population of seeds.

The term "measurable increase" (or "measurable decrease"), as used herein, means an increase (or decrease) that can be detected by assays known in the art as greater (or less) than control. For example, a measurable increase (or decrease) is an increase (or decrease) of about 2%, about 5%, about 10%, about 20%, about 30%, about 40%, about 50%, about 60%, about 70%, about 75%, about 80%, about 85%, about 90%, or more, compared to plants or a plant population not treated with the active ingredient.

The term "plant in need thereof," as used herein, means any plant which is healthy or which has been diagnosed with a plant disease or symptoms thereof, or which is susceptible to a plant disease, or may be exposed to a plant disease or carrier thereof.

The term "plant disease," as used herein, refers to any disease of a crop plant, caused by any plant pathogen, including but not limited to, bacterial, viral, fungal nematode, phytomyxean, protozoan, algal and parasite plant pathogens.

The term "plant disease symptoms," as used herein, refers to any symptom of disease, including the detectable presence of a known plant pathogen, or the presence of rot, mottling, galls, discoloration such as yellowing or browning, fruit greening, stunted growth, plant death, cellular death, cell wall breakdown, and/or the presence of spots, lesions, dieback, wilting, dwarfing, Witch's broom and/or knots.

The term "population of plants," as used herein, refers to a group of plants, all of the same species, that inhabit a particular area at the same time. Therefore, the plants in a nursery, a grove, a farm, and the like are considered a population.

The term "reduction of disease symptoms," as used herein, refers to a measurable decrease in the number or severity of disease symptoms.

The term "treating," treatment," and all its cognates, as used herein, refers to any application or administration to a plant, the soil surrounding the plant, the water applied to the plant, or the hydroponic system in which the plant is grown, which is intended to improve the health, growth or productivity of a plant, particularly a crop plant. For example, a treatment intended to increase the health or growth or a crop plant, increase crop yield of a plant or population of plants is contemplated as part of this definition, as well as treatment intended to improve disease symptoms or pathogen titer in the plant.

3. Overview

The invention relates to bacterial strains and combinations of bacterial strains that assist in inducing plant defenses against diseases, which are able to induce plant resistance effective against pathogens involved in HLB disease, and other diseases, in plants, as well as increase the health and vigor of any plants, including healthy plants, and increase seed germination and crop quantity and quality. These bacteria can be incorporated into a botanically acceptable vehicle and administered or applied to a plant of interest by any convenient known method. Preferable methods include injection to the soil surrounding the plant, application to the soil by spraying, soaking/drenching, seed treatment, or any other means conventionally used in agriculture, to induce uptake by the roots, or by injection into the plant itself, such as injection into the trunk, or by application to the leaves or any part of the plant. Application or administration methods that provide contact of the bacteria to the roots of the plant, such as soil applications within about a 10-foot radius of the trunk of the plant are preferred.

4. Description

Introduction

Methods and compounds for use in enhancing the health and vigor of plants are needed in the art, both to improve the productivity of healthy plants, and to increase the plant's natural ability to combat disease. Embodiments of this invention provide methods and compositions to assist in these goals, and to treat plants that are affected by disease as well. For example, plants treated according to embodiments of the invention can exhibit improved growth, seed germination, and defense against disease progression and disease symptoms, for example against HLB or *Ca. Liberibacter* infection. In the following description, for the purposes of explanation, certain specific details are set forth in order to provide a thorough understanding of the present invention. It will be apparent, however, to one skilled in the art, that the present invention may be practiced without these specific details.

Some bacteria have the ability to induce systemic resistance in plants, providing them with an advantage against plant pathogens and generally increasing health and vigor in the plants. The resulting induced systemic resistance (ISR) allows the plant to evoke a stronger and faster defense responses against a broad spectrum of pathogens in a systemic way. Physiologically, the ISR response is similar to the systemic acquired resistance (or SAR), triggered after an encounter with some plant pathogens. Both ISR and SAR are similar in the resulting defense against a broad number of pathogens. However, some differences exist between the responses. While SAR is thought to be activated through the salicylic acid pathway and accumulate PRs as a consequence, ISR is believed to be activated through the ethylene/jasmonate (ET/JA) pathways, and whether PRs accumulate is less understood. Plant defense responses were monitored using qRT-PCR by studying expression of selected defense genes on the leaf tissue. Genes involved in the ethylene/jasmonate (UJ) and salicylic acid (SA) pathways, as well as pathogensis-related (PR) protein-encoding genes were used as markers. Identities of three bacteria were determined by genomic DNA fingerprinting using 16SrRNA gene sequencing based analysis.

Beneficial bacteria have been isolated from the rhizosphere of healthy citrus trees in severely HLB-diseased groves in Florida. The phytobiome associated with such trees were found to harbor microbes able to improve plant defenses against citrus pathogens. It now has been discovered that the bacterial strains described here, alone and in combination, are able to induce systemic resistance and benefits to health and vigor, in a wide variety of plants, including any crop plants, and most preferably citrus, corn, soybean, and tomato crop plants.

Methods of Bacterial Isolation

Molecular identification of beneficial strains was achieved by amplification and sequencing of 16s rRNA. 16s rRNA was amplified from seven antibiotic-producing bacterial strains using primers 27F (5'-AGAGTTTGATCCTG-GCTCAG-3'; SEQ ID NO:1) and 1492R (5'-GGTTACCT-TGTTACGACTT-3'; SEQ ID NO:2). The corresponding amplification products then were sequenced with both primers and the universal primer 519F (5'-CAGCMGCCGCG-GTAATAC-3'; SEQ ID NO:3) to obtain a fragment of 1350 bp or more. Each strain was assigned to its closest microorganism based on BLAST analysis, and a phylogenetic tree was constructed with Neighbor Joining method with a bootstrap of 1000 using MEGA 6.0.

A phylogenetic tree was constructed to show the relationship of strains ATY16, PT6, and PT26A to other known strains. See FIG. 1. The phylogenic tree was constructed using DNA sequences of nine housekeeping genes (uvrD, secA, carA, recA, groEL, dnaK, atpD, gyrB and infB) aligned using the Maximum Likelihood method. Horizontal scale bar (0.05) at the top represents number of nucleotide substitutions per site. The DNA sequences of nine housekeeping genes (uvrD, secA, carA, recA, groEL, dnaK, atpD, gyrB and infB) are provided below. The bacteria can be isolated from soil on Nutrient Agar (NA) medium ((w/v) 0.5% peptone; 0.3% beef extract; 0.5% agar, pH 7) and incubated at 30° C. for 72 hours. Confirmation of the identity of the bacterial strains can be performed using the genome sequencing methods described below.

Bacterial Strains

The phylogenetic tree indicates that the strain ATY16 groups most closely with *Paenibacillus* sp. JDR-2 and *Paenibacillus mucilaginosus* K02, forming a distinct clade from other *Bacillus* and *Paenibacillus* species. The closest relative of the strain PT6 is *Bacillus megaterium* QMB1551. The closest relative of the strain PT26A is *Bacillus subtilis*.

The strain ATY16 shared 99% homology with the *Paenibacillus* sp. strain JDR-2 (Accession No. CP001656), *Paenibacillus glycanilyticus* strain NBRC 16618 (Accession No. NR_113853) and *Paenibacillus* sp. strain A12 (Accession No. KF479531). The strain PT6 shared 99% homology with the *Bacillus megaterium* strain GMA327 (Accession No. AB738784), *Bacillus aryabhattai* strain IHB B 7024 (Accession No. KJ721203), and *Bacillus* sp. strain NH1 (Accession No. JN208177). The strain PT26A shared 99% homology with several strains of *Bacillus subtilis* (Accession No. KJ767313, CP010052, and CP010053, etc.), and *Bacillus tequilensis* strain IHB B 6839 (Accession No. KF668464).

The general features of the three genomes are summarized in Table 1, below. The genome size of ATY16 is 6,788,192-bp, with 50.79% GC, 6,129 predicted CDSs (coding sequences), 85 types of tRNA and rRNA, and 39 estimated missing genes. The genome size of PT6 is 5,485,792-bp, with 37.76% GC, 5,666 predicted CDSs, 124 types of tRNA and rRNA, and 16 estimated missing genes. The genome size of PT26A is 4,360,593-bp, with 43.23% GC, 4,578 predicted CDSs, 84 types of tRNA and rRNA, and 38 estimated missing genes.

Analysis also indicated the presence of putative plant beneficial gene clusters in the three genomes. In *B. subtilis* PT26A, there are nonribosomal peptide synthetase (NRPS) gene clusters encoding surfactin production (comS, srfA, and rapA), genes for bacilysin (bacA, bacB, and bacE) and a bacillibactin siderophore, and several polyketide synthase (PKS) genes. The bacterium was equipped with genes for resistance to drugs and heavy metals, aromatic compound degradation, motility, and chemotaxis and for the synthesis of auxin precursors probably useful in the beneficial relationship with plants. It also harbors genes for synthesis of exopolysaccharides and biofilm, capsule and endospore proteins, and genes for assimilation of nitrogen (moaCDE, mobAB, moeAB; and nar/nas) and minerals, including Phosphate (phoPR), and Magnesium (mgtE, and corA). It also contains genes for the synthesis of 2,3-butandiol that can elicit a plant defense response. In *B. megaterium* PT6, there are genes encoding probable nikkomycin biosynthesis proteins, siderophore biosynthesis proteins, and genes for resistance to drugs and heavy metals, for motility and chemotaxis, for the synthesis of auxin precursors, for endospore proteins, and for assimilation of nitrogen and minerals. In *Paenibacillus* sp. ATY16, there are NRPS genes encoding antimicrobial(s) to be determined, Phenazine biosynthesis protein encoding genes, and genes for resistance to drugs and heavy metals, for motility and chemotaxis, for the synthesis of auxin precursors, for exopolysaccharides biosynthesis, for endospore protein biosynthesis, for assimilation of nitrogen and minerals, for xylan, chitin and N-cetylglucosamine utilization, and genes for putative insecticidal toxin complex.

TABLE 1

General features of the sequenced bacterial genomes

| General traits | B. megaterium | B. subtilis | Paenibacillus sp. |
|---|---|---|---|
| Genome size (bp) | 5,485,792 | 4,360,593 | 6,788,192 |
| Number of protein encoding | 5,666 | 4,578 | 6,129 |
| Hypothetical protein | 1947 | 1142 | 1739 |
| tRNAs and rRNAs | 124 | 84 | 85 |
| Number of missing genes | 16 | 38 | 39 |
| GC % | 37.76 | 43.23 | 50.79 |

Deposit Information

The bacterial strains *Bacillus megaterium* PT6, *Bacillus subtilis* PT26A, and *Paenibacillus* sp. ATY16 have been deposited in an international depository under conditions that assure that access to the culture will be available during the pendency of this patent application and any patent(s) issuing therefrom to one determined by the Commissioner of Patents and Trademarks to be entitled thereto under 37 C.F.R. 1.14 and 35 U.S.C. 122. These strains have been deposited on Feb. 2, 2016, in the American Type Culture Collection (ATCC), at 10801 University Boulevard, Manassas, Va., 20110-2209 United States of America, under the following accession numbers: *Bacillus megaterium* PT6 (accession number PTA-122799), *Bacillus subtilis* PT26A (accession number PTA-122797), and *Paenibacillus* sp. ATY16 (accession number PTA-122798).

Plants

The studies described herein have shown that the bacterial cultures according to embodiments of the invention have desirable effects on the growth of plants, their productivity and their ability to combat disease. The description herein provides data showing effects on a variety of crop plants, including both monocots and dicots, indicating that the effects are generalized and widespread, and can provide benefits to the health and vigor of all plants, and improvements in fighting a wide variety of diseases. Any plant is contemplated for use with the invention, both healthy plants and those which have been exposed to or may be exposed to a plant pathogen or a carrier of a plant pathogen.

Preferred plants for use with the invention include citrus, corn, soybean, potato, tomato, sugar cane, and strawberry, which are major fruit or food crops, however any plant, including both crop and ornamental plants can be treated with the methods and compositions described herein.

The invention is contemplated for use on plants at all stages of development, including seeds, seedlings and mature plants, which are cultivated by any method known in the art which is convenient for the plant in question. Plants in the field, on farms or in a natural environment are included as useful for practicing the invention, as well as plants in a nursery or greenhouse, or a raised bed, home garden, or hydroponics facility, on a large or small scale.

Bacterial Effects

Without wishing to be bound by theory, the bacterial strains described herein beneficially affect plants to which they are exposed, by increasing the expression of certain genes in the plant, at least some of which are related to the natural plant defense mechanisms of the plant. The bacteria improve the metabolism of the plant, thereby enhancing growth, productivity and disease resistance and the ability to combat disease.

The data provided herein show both general effects on growth and productivity in plants, which demonstrate an effect on the health and vigor of the plants, as well as effects on plant pathogens that beneficially affect infected plants. PT26A inoculation promoted germination of seeds in all three crops and also improved the vigor of germinating seeds. See Examples.

Methods for study of the effects of the beneficial bacterial strains include root inoculation with the bacteria (or control), monitoring expression of defense genes in the inoculated plants, a pathogen challenge on leaves, for example *Xanthomonas citri* subsp. *citri*, and monitoring the development of disease in the plants.

Plant Diseases

Diseases for which embodiments of the invention are contemplated for use include diseases of citrus, including, but not limited to:

Bacterial diseases (bacterial spot, black pit (fruit), blast, citrus canker, citrus variegated chlorosis, huanglongbing (citrus greening);

Viral diseases (citrus mosaic, bud union crease, citrus leaf rugose, citrus yellow mosaic, crinkly leaf, infectious variegation, navel infectious mottling, psoriasis, satsuma dwarf, tatter leaf, tristeza, citrus leprosis), Fungal diseases (albinism, alternaria brown spot, anthracnose, areolate leaf spot, black mold rot, black root rot, black rot, blue mold, botrytis, branch knot, brown rot (fruit), charcoal root rot, citrus black spot, dumping off, dry rood complex, dry rot, fly speck, fusarium, green mold, heart rot, leaf spot, mucor fruit rot, phymatotrichum root rot, phomopsis stem-end rot, phytophthora, pink disease, pink mold, pleospora rot, poria root rot, post bloom fruit drop, powdery mildew, rootlet rot, rosellinia root rot, scab, sclerotinia twig blight, septoria spot, sooty blotch, sour rot, sweet orange scab, thread blight, Trichoderma rot, twig blight, ustulina root rot, whisker mold and white root rot);

and diseases of corn, including, but not limited to:

Bacterial diseases (bacterial leaf blight and stalk rot, bacterial leaf spot, bacterial stalk rot, bacterial stripe, chocolate spot, Goss's bacterial wilt and blight, holcus spot, purple leaf sheath, seed rot-seedling blight, Stewart's disease, and corn stunt);

Fungal diseases (phytophthora, anthracnose leaf blight, anthracnose stalk rot, aspergillus ear and kernel rot, banded leaf and sheath spot, black bundle disease, black kernel rot, borde blanco, brown spot, black spot, stalk rot, cephalosporium kernel rot, charcoal rot, corticium ear rot, diplodia, didymella, downy mildews, dry ear rot, ergot, eyespot, fusarium, gibberella, grey leaf spot, cercospora, helminthosporium, hormodendrum, cladosporium, hyalothyridium, late wilt, white blast, stripe, northern corn leaf spot, penicillium ear rot, blue eye, blue mold, phaeocytostroma stalk rot, phaeosphaeria leaf spot, botrysphaeria ear rot, pythium root rot, red kernel disease, sclerotial rot, rhuzoctonia root rot, rust, southern blight, and smut);

Viral diseases (maize bushy stunt, maize chlorotic dwarf, maize chlorotic mottle, maize leaf fleck, maize mosaic, maize pellucid ringspot, maize red leaf, maize ring mottle, maize streak, maize stripe, maize tassel abortion, maize white leaf, and northern cereal mosaic);

and diseases of soybean, including, but not limited to:

Bacterial diseases (bacterial blight, bacterial pustules, bacterial tan spot, bacterial wilt, and wildfire);

Fungal diseases (alternaria leaf spot, anthracnose, black leaf blight, black root rot, brown spot, charcoal rot, choanephora leaf blight, downy mildew, fusarium root rot, fusarium sudden death syndrome, leptosphaerulina leaf spot, mycoleptodiscus root rot, phomopsis seed decay, phyllosticta leaf spot, powdery mildew, Pythium rot, phytophthora, red crown rot, rhizoctonia, rust, scab, southern blight, target spot, and yeast spot);

Viral diseases (bean pod mosaic, bean yellow mosaic, Brazilian bud blight, peanut mottle, soybean chlorotic mottle, soybean crinkle leaf, soybean mosaic, soybean severe stunt, and bud blight);

and diseases of tomato, including, but not limited to:

Bacterial diseases (bacterial canker, bacterial speck, bacterial wilt, pith necrosis, and syringae leaf spot);

Fungal diseases (alternaria stem canker, anthracnose, black mold rot, black root rot, cercospora leaf mold, charcoal rot, didymella stem rot, early blight, fusarium, grey leaf spot, gray mold, late blight, leaf mold phoma rot, phytophthora, powdery mildew, rhizoctonia, rhizopus rot, septoria leaf spot, sour rot, southern blight, target spot, verticillium wilt, and white mold);

Viral diseases (curly top, tomato bushy stunt, tomato etch, tomato mosaic, tomato mottle, tomato necrosis, tomato spotted wilt, tomato yellow top, tomato bunchy top, common mosaic of tomato, and tomato big bud);

and diseases of sugar cane, including, but not limited to:

Bacterial diseases (gumming disease, leaf scald, mottled stripe, ratoon stunting disease, and red stripe);

Fungal diseases (banded sclerotial disease, black rot, black stripe, brown spot, brown stripe, downy mildew, eye spot, fusarium, iliau, leaf blast, leaf blight, leaf scorch, marasmius sheath and shoot blight, phyllosticta leaf spot, phytophthora, phytophthora rot of cuttings, pineapple disease, red leaf spot, rhizoctonia sheath and shoot rot, rind disease, ring spot, common rust, orange rust, schizophyllum rot, sclerophthora disease, seedling blight, smut, wilt, yellow spot, and zonate leaf spot);

Viral diseases (chlorotic streak, Fiji disease, mosaic, streak disease, and yellow leaf);

and diseases of strawberry, including, but not limited to:

Bacterial diseases (angular leaf spot, bacterial wilt and cauliflower disease);

Fungal diseases (powdery mildew, alternaria fruit rot, anthracnose, armillaria crown and root rot, black leaf spot, black root rot, cercospora leaf spot, charcoal rot, common leaf spot, coniothyrium diseases, diplodina rot, downy mildew, brown cap, byssochlamys rot, gray mold leaf blight, hainesia leaf spot, leaf blotch, leaf rust, leaf scorch, powdery mildew, botrytis crown rot, idriella root rot, olpidium root infection, phytophthora, synchytrium root gall, rhizoctonia bud and crown rot, rhizopus rot, southern blight, and verticillium wilt);

Viral diseases (strawberry chlorotic fleck, strawberry crinkle, strawberry mottle, strawberry vein banding, strawberry green petal, strawberry lethal decline, strawberry latent ringspot, strawberry mycoplasma yellows disease, arabis mosaic virus, and strawberry pallidosis).

A person of skill in the art is aware of methods for determining whether a plant is in need of treatment for a plant disease (for example HLB or *Ca. Liberibacter* infection), and which plants may be or may become susceptible to a plant disease. Therefore, the invention described and claimed herein is contemplated for use in any plant which is or which may become infected with a plant disease, as determined by a person of skill. Due to its nature in inducing plant defenses and in improving health and vigor, it is recommended to use it when the trees are firstly planted in the field to prevent disease development, or to treat seeds prior to planting. Methods according to embodiments of the invention preferably are used when the person of skill in the art becomes aware of a plant with early symptoms of HLB disease on leaves, which may be small and upright, with vein yellowing and an asymmetrical chlorosis referred to as "blotchy mottle." Methods according to embodiments of the invention also advantageously can be used when a person of skill in the art becomes aware that a plant is becoming infected by HLB as determined using PCR methods known in the art, for example quantitative real time PCR (qPCR) tests. The inventive methods can also be used prophylactically or in a more severely infected plant with disease of longer standing.

Methods of Administration

Persons of skill are aware of various methods to apply compounds, including live bacteria, to plants for surface application or for uptake, and any of these methods are contemplated for use in this invention. Methods of administration to plants include, by way of non-limiting example, application to any part of the plant, by inclusion in irrigation water, by injection to the plant or to the soil surrounding the plant, or by exposure of the root system to aqueous solutions containing the compounds, by use in hydroponic or aeroponic systems, by seed treatment, by exposure of cuttings of citrus plants used for grafting to aqueous solutions containing the compounds, by application to the roots, stems or leaves, by application to the plant interior, or any part of the plant to be treated. Any means known to those of skill in the art is contemplated.

Application of the bacteria can be performed in a nursery setting, a greenhouse, hydroponics facility, or in the field, or any setting where it is desirable to treat plants which have been or can become exposed to a plant disease, such as HLB or *Ca. Liberibacter* infection, or which can benefit from an enhancement of health and vigor. The methods and bacteria of this invention can be used to treat infection with a plant pathogen and can be used to improve plant defenses or health, growth and productivity in plants which are not infected. Thus, any plant in need, in the context of this invention, includes any plant susceptible to a lack of optimum health and vigor, or susceptible to a plant disease, whether currently infected or in potential danger of infection, in the judgement of the person of skill in this and related arts.

Application to seeds is preferably accomplished as follows, however any method known in the art can be used. Seeds may be treated or dressed prior to planting, by soaking the seeds in a solution containing the bacteria at a concentration of $10^3$ to $10^{11}$ cells/mL over a period of minutes or hours, applying the bacteria at a concentration of $10^3$ to $10^{11}$ cells/mL to seeds during planting, or by coating the seeds with a carrier containing the compounds at a concentration of $10^3$ to $10^{11}$ cells/mL. The concentrations, volumes, and duration may change depending on the plant.

Application to soil is preferably performed by soil injection or soil drenching, however any method known in the art can be used. These methods of administration are accomplished as follows. Soil drenching may be performed by pouring a solution or vehicle containing the bacteria at a concentration of $10^3$ to $10^{11}$ cells/mL at 0.5 to 1 gallon/tree to the soil surface in a crescent within 10 to 100 cm of the trunk on the top side of the bed to minimize runoff, and/or by using the irrigation system. Soil injection may be performed by directly injecting a solution or vehicle containing the bacteria at a concentration of $10^3$ to $10^{11}$ cells/mL into the soil within 10 to 100 cm of the trunk using a soil injector. The concentrations, volumes, and duration may change depending on the plant and can be determined by one of skill in the art, however preferred methods are those wherein the administering to the plant provides at least $10^2$ cfu of the isolated bacterial strain per gram of plant root thirty days after administration or at least $10^3$ cfu of the isolated bacterial strain per gram of plant root thirty days after administration.

Application to hydroponic or culture media preferably is performed as follows, however any method known in the art can be used. A solution or vehicle containing the bacteria at a concentration of $10^3$ to $10^{11}$ cells/mL may be added into the hydroponic or culture media at final concentrations suitable for plant growth and development. The concentrations, and volumes may change depending on the plant, and can be determined by one of skill in the art.

Application to the roots preferably is performed by immersing the root structure in a solution or vehicle in a laboratory, nursery or hydroponics environment, or by soil injection or soil drenching to the soil surrounding the roots, as described above. Emersion of the root structure preferably is performed as follows, however any method known in the art can be used. A solution or vehicle containing the bacteria at a concentration of $10^3$ to $10^{11}$ cells/mL may be applied to the roots by using a root feeder at 0.5 to 1 gallon/tree. The concentrations, volumes, and duration may change depending on the plant and can be determined by one of skill in the art, however preferred methods are those wherein the administering to the plant provides at least $10^2$ cfu of the isolated bacterial strain per gram of plant root thirty days after administration or at least $10^3$ cfu of the isolated bacterial strain per gram of plant root thirty days after administration.

Application to the stems or leaves of the plant preferably is performed by spraying or other direct application to the desired area of the plant, however any method known in the art can be used. A solution or vehicle containing the bacteria at a concentration of $10^3$ to $10^{11}$ cells/mL may be applied with a sprayer to the stems or leaves until runoff to ensure complete coverage, and repeat three or four times in a growing season. The concentrations, volumes and repeat treatments may change depending on the plant and can be determined by one of skill in the art.

Application to the plant interior preferably is performed by injection directly into the plant, for example by trunk injection or injection into an affected limb, however any method known in the art can be used. A solution or vehicle containing the bacteria at a concentration of $10^3$ to $10^{11}$ cells/mL may be applied with an injector into the plant interior, and repeat three or four times in a growing season. The concentrations, volumes and repeat treatments may change depending on the plant and can be determined by one of skill in the art.

Preferred methods of administration are soil application methods, including soil injection, soil soaking or soil spraying. A highly preferred method according to the invention for treatment of trees is application to the soil by soil injection within a 10-foot radius of a plant to be treated, for example a plant exhibiting infection with or symptoms of infection with a plant pathogen. Any method of administering the bacteria which contacts the bacteria with the roots of the plant is preferred. The concentrations, volumes, and duration may change depending on the plant and can be determined by one of skill in the art, however preferred methods are those wherein the administering to the plant provides at least $10^2$ cfu of the isolated bacterial strain per gram of plant root thirty days after administration or at least $10^3$ cfu of the isolated bacterial strain per gram of plant root thirty days after administration.

Typically, the bacterial strain or strains are administered so as to achieve at least $10^2$-$10^3$ cfu, preferably at least about $10^2$ cfu, of each bacterial strain administered per gram of root after a thirty day period, or preferably more than $10^2$-$10^3$ cfu of each bacterial strain per gram of root, or more than $10^5$ cfu or $10^9$ cfu of each bacterial strain per gram of root. In a specific embodiment, administering involves administering bacterial strains according to an amount and frequency to achieve at least $10^2$ or $10^3$ cfu/g of root for each bacterial strain after a thirty day period. The composition administered preferably contains more than $10^3$ cfu/mL of each bacterial strain or $10^3$ to $10^{12}$ cfu/mL, or $10^4$-$10^{10}$ cfu/mL, or $10^5$-$10^9$ cfu/mL or $10^7$ cfu/mL of each bacterial strain. A preferred goal of the administration of the bacteria according to embodiments of the invention is to increase the colony-forming units of the bacterial strains at the roots of the plants, and particularly to increase those levels above any natural levels, if any. Therefore compositions are administered to deliver an amount of bacteria to achieve this goal.

A particularly preferred embodiment involves providing the at least one bacterial strain in an amount and with a frequency to achieve at least $10^2$ cfu, $10^3$ cfu, $10^4$ cfu, $10^5$ cfu or more of each bacteria per gram of root after a thirty day period. In one embodiment, the composition administered contains a botanically acceptable vehicle and at least $10^3$ cfu/mL of each bacterial sample. The method can include one bacterial strain, two bacterial strains, three bacterial strains, four bacterial strains, or more, provided in separate carriers or provided together as a mixture.

Compositions

Compositions according to embodiments of the invention preferably include a botanically acceptable vehicle or carrier, preferably a liquid, aqueous vehicle or carrier such as water, and at least one bacterial strain. Preferably, the composition contains $10^3$ cfu/mL to $10^{10}$ cfu/mL of each bacterial strain, most preferably about $10^7$ cfu/mL to about $10^9$ cfu/mL of each bacterial strain. The composition may be formulated as an emulsifiable concentrate(s), suspension concentrate(s), directly sprayable or dilutable solution(s), coatable paste(s), dilute emulsion(s), wettable powder(s), soluble powder(s), dispersible powder(s), dust(s), granule(s) or capsule(s).

The composition may optionally include a botanically acceptable carrier that contains or is blended with additional active ingredients and/or additional inert ingredients. Active ingredients which can be included in the carrier formulation can be selected from any combination of pesticides, herbicides, plant nutritional compositions such as fertilizers, and the like. Plant inducer compounds such as salicylic acid or β-aminobutyric acid (BABA) also can be included in the compositions. Additional active ingredients can be administered simultaneously with the bacterial strains described here, in the same composition, or in separate compositions, or can be administered sequentially.

Inert ingredients which can be included in the carrier formulation can be selected from any compounds to aid in the physical or chemical properties of the composition. Such inert ingredients can be selected from buffers, salts, ions bulking agents, colorants, pigments, dyes, fillers, wetting agents, dispersants, emulsifiers, penetrants, preservatives, antifreezes, evaporation inhibitors, bacterial nutrient compounds, anti-caking agents, defoamers, antioxidants, and the like.

5. Examples

Example 1. Experimental Methods

A. Isolation and Identification of Bacteria

Endophytic bacterial strains were isolated from healthy citrus rhizosphere of asymptomatic Valencia orange (*Citrus sinensis*) trees in a heavily Huanglongbing (HLB) diseased grove of citrus in Fort Pierce, Fla., and were isolated and morphologically characterized as described by Trivedi et al., 2011. The bacteria were isolated using nutrient agar (NA) (BD, Sparks, Md., USA) or tryptone yeast (TY) extract agar medium (Sigma, St. Louis, Mo., USA). The bacterial isolates were also evaluated in vitro for plant growth promoting activity and biocontrol ability, using the methods described by Trivedi et al., 2011. Then the bacterial isolates were subjected to molecular identification using 16S rDNA analysis. DNA extraction, 16S rRNA gene amplification, and sequencing was performed as previously described (Trivedi et al. 2011). Homology was determined using the Blastn programme within the NCBI database (http://www.ncbi.nlm.nih.gov/BLAST/). Bacterial strains also were screened for the ability to elicit induced systemic resistance (ISR) as described in the art.

Genomic DNA was extracted from bacterial culture grown overnight at 28° C. in Luria-Bertani (LB) broth medium (Bertani, et al., 1951) using the Wizard genomic DNA purification Kit (Promega, Madison, Wis.) according to the manufacturer's instructions. Quantity and quality of the DNA samples were determined spectrophotometrically (Nanodrop ND-1000; NanoDrop Tech. Inc., Wilmington, Del.). Whole-genome sequencing was performed using an Illumina HiSeq 2000 system at the Beijing Genomic Institute (BGI, Shenzhen, China). All generated paired-end reads were qualitatively assessed, trimmed to remove the vector sequences, and assembled de novo using the Short Oligonucleotides Alignment Program (SOAP) according to the instructions (http://soap.genomics.org.cn/index.html#intro2). The draft genome sequence was annotated using both RAST server (Aziz et al., 2008) and NCBI Prokaryotic Genomes Automatic Annotation Pipeline (PGAAP). The annotations were manually refined by direct comparison to closely related completed genomes.

To determine the phylogenic relationship of the three bacterial isolates of ATY16, PT6, and PT26A to other *Bacillus* spp. and *Paenibacillus* spp., nine housekeeping genes, uvrD, secA, carA, recA, groEL, dnaK, atpD, gyrB, and infB, from 18 completely sequenced *Bacillus* spp. and *Paenibacillus* spp. were used to construct a phylogenic tree. Nucleotide sequences of the nine genes from the above genomes were aligned using DNAMAN and the resulting alignments were presented as a phylogenic tree with the maximum likelihood method.

Almost the full-length nucleotide sequence of the 16S rDNA region of the strain was determined and homology search was performed between the thus determined nucleotide sequence and the DDBJ/EMBL/GenBank international nucleotide sequence database using the Blastn homology search program. The ATY16, PT6, and PT26A strains were preliminarily identified by genomic DNA fingerprinting using 16S rRNA gene sequencing based analysis. The near full-length nucleotide sequence (about 1470 bp) of the 16S rDNA region of the strain was determined and homology search was performed using the GenBank/DDBJ/EMBL international nucleotide sequence database with the Blastn homology search program. The three bacterial strains ATY16, PT6, and PT26A were selected from 39 bacterial isolates for further characterization as they showed the potential to enhance plant growth and/or suppress plant diseases in preliminary tests for plant growth promoting (PGP) and biocontrol ability.

Genomic DNA fingerprinting was performed using housekeeping genes (uvrD, secA, carA, recA, groEL, dnaK, atpD, gyrB, and infB) which were determined by whole genomic sequencing according to methods well known in the art. For this analysis, bacteria with complete known genomes were used, and draft genomes were excluded due to their limitations. To further determine the position of the three bacterial strains in the groups of *Paenibacillus* spp. and *Bacillus* spp., a phylogenetic tree was constructed using the maximum-likelihood method for complete sequences of nine housekeeping genes (uvrD, secA, carA, recA, groEL, dnaK, atpD, gyrB, and infB) derived from sequenced genomes of *Paenibacillus* spp., along with the sequences of some members of the *Bacillus* spp. These genes have provided robust analysis and resolved evolutionary relationships reliably in other studies. For this analysis, we focused on bacteria with complete genomes and excluded draft genomes due to the limitations of draft genomes. An alignment of the nine genes were created and a phylogenetic tree constructed. See FIG. 1 and the sequence data below. The phylogenetic tree (FIG. 1) indicates that the strain ATY16 groups most closely with *Paenibacillus* sp. JDR-2 with a 98% similarity and *Paenibacillus mucilaginosus* K02 with a 94% similarity, forming a distinct clade from other *Bacillus* and *Paenibacillus*. The closest relative of the strain PT6 is *Bacillus megaterium* QMB1551 with a 97% similarity. The closest relative of the strain PT26A is *Bacillus subtilis* with a 97% similarity.

The 16S rDNA sequence analysis showed that the strain PT6 shared 99% homology with the *Bacillus aryabhattai* strain IHB B 7024 (Accession No. KJ721203), *Bacillus megaterium* strain GMA327 (Accession No. AB738784), and *Bacillus* sp. strain NH1 (Accession No. JN208177). The strain PT26A shared 99% homology with several strains of *Bacillus subtilis* (Accession No. KJ767313, CP010052, and CP010053, etc.), and *Bacillus tequilensis* strain IHB B 6839 (Accession No. KF668464). The strain ATY16 shared 99% homology with *Paenibacillus* sp. strain JDR-2 (Accession No. CP001656), *Paenibacillus glycanilyticus* strain NBRC 16618 (Accession No. NR_113853) and *Paenibacillus* sp. strain A12 (Accession No. KF479531).

The 16S rDNA sequences of these bacterial strains are available in the NCBI GenBank database with the accession number listed above. See also the sequence information below.

Based on the foregoing information, one skilled in the art would be able to identify the bacterial strains described above. Furthermore, the bacterial strains *Bacillus megaterium* PT6, *Bacillus subtilis* PT26A, and *Paenibacillus* sp. ATY16 have been deposited under the Budapest treaty in in the American Type Culture Collection (ATCC), under the following accession numbers: *Bacillus megaterium* PT6 (accession number PTA-122799), *Bacillus subtilis* PT26A (accession number PTA-122797), and *Paenibacillus* sp. ATY16 (accession number PTA-122798).

The deposit was received by the ATCC on Feb. 2, 2016 under the provisions of the Budapest Treaty, and all restrictions upon public access to the deposit will be irrevocably removed upon the grant of a patent on this application. The deposits will be available as required by foreign patent laws in countries wherein counterparts of the subject application, or its progeny, are filed. It should be understood, however, that the availability of the deposits does not constitute a license to practice the subject invention in derogation of patent rights granted by governmental action.

B. Assays for Plant Beneficial Traits

Qualitative and quantitative assays were performed for traits related to mineral nutrition (phosphate (P) solubilization, siderophore production, nitrogen (N) fixation), plant development (indole acetic acid (IAA) synthesis), plant health (production of antibiotic and lytic enzymes (chitinase)), induction of systemic resistance (salicylic acid (SA) production), and stress relief (production of 1-aminocyclopropane-1-carboxylate (ACC) deaminase) using methods available in the art and described by Trivedi et al., 2011. All the experiments were done in triplicate and repeated three times.

Plant defense responses were studied by measuring the expression of genes involved in plant defense. A one-step qRT-PCR was performed with a 7500 fast real-time PCR system (Applied Biosystems, Foster City, Calif.) using a QuantiTect SYBR green RT-PCR kit (Qiagen, Valencia, Calif.) following the manufacturer's instructions. Total RNA was extracted from leaf samples by grinding two leaves per sample in liquid nitrogen and 200 mg of tissue was processed using the RNeasy® Mini kit for plant tissue (Qiagen, MD, USA), Contaminated genomic DNA was removed using a TURBO DNA-free kit (Ambion, Austin, Tex.), following the manufacturer's instructions. RNA purity and quality were assessed with a NanoDrop ND-1000 spectrophotometer (NanoDrop Technologies, Wilmington, Del.). RNA concentration was adjusted to 50 ng/µL, and 2 µL of sample was used for quantitative reverse transcription-PCR (qRT-PCR) relative quantitation of gene expression. See Table 2, below for a list of genes of interest. The housekeeping gene encoding glyceraldehyde-3-phosphate dehydrogenase-C (GAPDH-C) was used as the endogenous control. The relative fold change in target gene expression was calculated using the formula $2^{-\Delta\Delta CT}$ (Livak and Schmittgen, 2001), where $\Delta\Delta CT=(Ct_{target}-Ct_{reference})_{Treatment}-(Ct_{target}-Ct_{reference})_{Control}$. qRT-PCR was repeated twice with three independent biological replicates each time.

TABLE 2

Defense-related Genes.

| Short name | Encoded protein |
| --- | --- |
| AOS | Allene oxidase synthase (JA synthesis) |
| HPL1 | Fatty acid hydroperoxide lyase |
| GPX | Phospholipid hydroperoxide glutathione peroxidase |
| NPR1 | Transcriptional regulator of defense genes (JA/ET and SA pathways) |
| MYC2 | Transcriptional activator (JA dependent defenses) |
| PR1 | Pathogenesis related protein 1 |
| PR5 | Pathogenesis related protein 5 |
| PAL | Phenylalanine ammonia lyase (JA/ethylene signal pathway) |
| SAM-SACM | S-adenosyl-L-methionine-salicylic acid carbosyl methyltransferase, (synthesis of SA) |
| CAT | Catalase |
| MPK4 | mitogen-activated protein kinase 4 |

C. Exemplary Crop Yield Measurements

Crop yield is calculated by harvesting the crop and comparing the weight of the crop obtained. For example, the yield of a citrus tree is estimated as the number of boxes of fruit per tree. One box is equivalent to approximately 90 lbs (40.8 kg) of fruit. A composite sample of the crop, randomly chosen from plants can be used for quality analysis. For example, fruit can be juiced and the percentage juice calculated according to Gottwald et al., 2012. Juice quality can be determined following standard methods as well (Gottwald et al., 2012). Fruit acidity can be expressed as percent citric acid. Total soluble solids are expressed as fruit brix (the measure of sugar content in fruit; i.e., 1 g of sugar/100 g of juice is equivalent to 1° of Brix). The fruit brix acidity ratio can be calculated, also according to known methods from the data collected.

D. Quantitative Real-Time PCR (qPCR) to Estimate Las Titer in Leaf Samples

For the treatments which showed a suppressive effect against HLB disease development or progress after the initial application, the expression pattern of three plant defense-related genes in the treated citrus was determined by quantitative real time PCR. Samples were taken at four time points (1, 2, 3 or 4, and 6 days after a single application of the treatments). To estimate the Las bacterial titer in treated trees, eight leaves with mottling symptoms were collected from each tree and a combined sample of 100 mg of mid-rib was excised for DNA extraction. DNA from leaf samples was extracted using the Wizard Genomic DNA purification kit (Promega Corp., Madison, Wis., USA) following the protocol for isolating genomic DNA from the plant tissue. The extracted DNA was quantified using a nano-drop spectrophotometer (NanoDrop Technologies, Wilmington, Del.) and adjusted to 100 ng/µL.

qPCR assays were performed in a 96-well plate using an ABI 7500 fast real-time PCR system (Applied Biosystems, Foster City, Calif., USA). The primer/probe set CQULA04F-CQULAP10P-CQULA04R targeting the β-operon region of Las was used (Wang et al., 2006) and qPCR reactions were performed according to the conditions described by Trivedi et al. (2009). Each individual sample was replicated three times and the whole reaction was repeated twice. Raw data were analyzed using ABI SDS software with the default settings of the software except that the threshold was adjusted to 0.02 following the instruction of the QuantiTect Probe PCR Kits (Qiagen, MD, USA). The standard equation Y=11.607−0.288X, where Y is the estimated log concentration of templates and X is the qPCR Ct values, as described by Trivedi et al. (2009), was used to convert individual Ct values into bacterial population as genome equivalents or cells (1 cell=1 genome equivalent) per gram of samples.

E. Bacterial Formulation Shelf Life.

The shelf life of three different formulations of the bacterial culture (AY16, PT6 and PT26A) were evaluated as follows. The bacterial strains were prepared in the following formulations: (1) solid alginate beads, and (2) broth-based preparations.

Solid alginate formulations were prepared following the method of Bashan (1986) with modifications under sterilized conditions. The bacterial strains were cultured in Luria-Bertani (LB) broth at 28° C. with shaking at 180 rpm for 24 hours to obtain a final concentration of $10^{10}$ CFU/mL. Bacterial suspension was aseptically mixed with autoclaved sodium alginate solution (2.0% wt/vol; Sigma, St. Louis, Mo., USA) and stirred gently for 1 hour. For preparing the beads, this mixture was added dropwise into sterilized 0.1 M $CaCl_2$ (Sigma, St. Louis, Mo., USA). The resulting alginate beads were maintained in the solution at room temperature for 2 hours for further solidification. The beads were then washed twice with sterile distilled water and incubated in fresh LB broth for an additional 24 hours in a rotary shaker at 28° C. to allow bacteria to multiply inside the beads. Then the beads were washed twice with sterile distilled water and air dried overnight in a laminar flow hood.

Broth based formulations were prepared in LB and orange peer based broth (OPB) respectively. The broth was inoculated with a loop full of freshly grown bacterial culture and incubated at 28 at 28° C. with shaking at 180 rpm for 24 hours raising the final concentration of $10^8$ cfu/mL. Fresh bacterial cultures were also diluted in sterilized tape water for viability determination.

Viable bacteria in the stored formulations were counted by dissolving 1 g in the case of the solid formulation or 1 mL of liquid formulation in 9 mL 0.85% NaCl in a test tube for 16-24 hours at 28° C. Further enumeration was performed using dilution-plate technique with NA medium. The plates were incubated at 28° C. and CFU were counted after 24 hours. The formulations were stored at two temperatures, 4±2° C. and room temperature (~23° C.), and viability was checked at an interval of two months. The plate counts were conducted in triplicate and the final values (log 10 cfu/g or /mL) of viable bacteria were the average of three readings. Under room temperature, after a 20-month storage, the bacterial populations in LB broth, OPB broth and sterilized tap water were about $10^2$-$10^3$ cfu/mL with initial populations of $10^8$ cfu/mL. At 4±2° C., after 20-month storage, the bacterial populations in LB broth, OPB broth and sterilized tape water are around $10^5$-$10^6$ cfu/mL with an initial population of $10^8$ cfu/mL.

The bacterial viability of alginate bead formulations was also determined and the results were presented in Table 3, below. After a period of 9 months storage at 4±2° C., there was no loss in viability of AY16, PT6 and PT26A in alginate bead formulations; while at room temperature (~23° C.), there was no loss in viability over a period of 4 months, and after 6 months, the loss in viability was observed readily.

TABLE 3

Viability of bacterial strains in alginate bead formulations under storage.

| Storage period | Lg (cfu/g) at 4 ± 2° C. | | | Lg (cfu/g) at room temperature (about 23° C.) | | |
|---|---|---|---|---|---|---|
| (month) | ATY16 | PT6 | PT26A | ATY16 | PT6 | PT26A |
| 0 | 8.72 a | 9.21 a | 9.72 a | 8.44 a | 9.43 a | 9.85 a |
| 2 | 8.43 a | 9.42 a | 9.48 a | 8.56 a | 9.62 a | 9.52 a |
| 4 | 8.52 a | 9.57 a | 9.51 a | 8.22 a | 9.18 a | 9.26 a |
| 6 | 8.24 a | 9.26 a | 9.06 a | 7.08 b | 8.23 b | 8.11 b |
| 9 | 8.35 a | 9.19 a | 9.25 a | 5.15 c | 6.32 c | 6.04 c |

Note:
The means of three replicates were shown. Data with different letter in the same column are significantly different at P < 0.05 (Student's t-test).

F. Germination and Plant Growth

For assays with *Arabidopsis*, corn, soybean and tomato, sterile Petri dishes (150 mm diameter) containing 40 mL autoclaved water agar (0.65%) was used for seed germination. Petri dishes were partially sealed with parafilm to prevent water loss from evaporation. The experiment was repeated three times with 40 seeds per replicate and arranged in a completely randomized design with three replications. The experiments were conducted in the light and temperature-controlled growing cabinet with constant temperature of 28° C. and a daily cycle of 12 h light and darkness.

For assays with citrus (*Citrus paradisi* 'Duncan' Grapefruit), Deepot cell containers containing sterilized Metro-Mix professional growing soil was used for seed germination in a quarantine greenhouse at the Citrus Research and Education Center, Lake Alfred, Fla. The greenhouse was maintained at approximately 25-30° C. and 60% relative humidity. *Arabidopsis*, citrus, corn, soybean and tomato seeds were surface sterilized using 1% NaClO and 70% ethanol. Seeds were then washed with autoclaved Millipore water four times to remove the residual bleach and ethanol.

Inoculum of each strain of ATY16, PT6, and PT26A was taken from a pure culture stored with glycerol in −80° C. and streaked onto the nutrient agar plate and incubated at 28° C. for 2 days. A loop full of each culture was transferred separately into the nutrient broth (25 mL) (for ATY16, added 0.5% yeast extract and 0.5% xylan) and incubated for 16 h at 28° C. with constant agitation (180 rpm). Prior to inoculation, bacterial cultures were pelleted by centrifugation (4000×g, 15 min), washed with autoclaved 0.85% (w/v) NaCl, and resuspended in the same buffer solution. The number of colony forming unit (CFU) was determined after series of dilution and agar plating. Seeds were inoculated at population of $10^{8-9}$/mL by soaking the surface sterilized seeds in bacterial suspension for 1 hour to allow bacteria bind to the seed coat and for seed imbibition. A similar procedure was used for control except the seeds were soaked in buffer solution. Inoculated *Arabidopsis*, corn, soybean and tomato seeds were spread out in sterile Petri dishes with autoclaved water agar (0.65%), and grapefruit seeds planted in the Deepot cells and maintained in the greenhouse.

For *Arabidopsis*, corn, soybean and tomato, daily germination was recorded and the germination rate (percent of germinated seeds) was calculated. Seedlings from germinated seeds were weighed at the final day of the experiment. For citrus, weekly germination was recorded and germination rate was calculated. Student's t-test (P<0.05) was used to test the significance of the difference between the means.

Example 2. Compatibility of Bacteria with UV Protectant and SAR Inducers

Bacteria were subjected to the following conditions. The compatibility of bacterial strains with ultraviolet (UV) protectant was determined by growing the tested bacterium in LB broth medium with different concentrations of a water soluble sodium salt of lignin (Sigma, St. Louis, Mo., USA), or without lignin, under short-wave UV radiation (254 nm in a biological safety cabinet) at a distance of 60 cm for 1 hour. The bacterial population was measured by counting the number of colonies using spread plate techniques on NA plates after incubating at 28° C. for 24 hours. The change in bacterial cell number in LB with or without UV protectant supplementation was determined. The compatibility of bacterial strains with SAR inducers was determined by growing the tested bacterium in LB broth medium with or without different concentrations of salicylic acid (SA), acibenzolar-S-methyl (ASM), and 2,6-dichloroisonicotinic acid (INA) (Sigma, St. Louis, Mo., USA), at 28° C. for 20 hours. The bacterial population was measured, and the change in bacterial cell number in LB with or without SAR inducer supplementation was determined. The tests were repeated three times with three replicates each time. Student's t-test was used to test the significance of the differences.

A water soluble sodium salt of lignin (Sigma, St. Louis, Mo., USA) at concentrations 0.2 and 0.3% (wt/vol) were able to enhance the survival of bacterial cells of ATY16, PT16 and PT26A versus controls when cells were exposed to UV for 1 hour. See Table 4, below. The assays for compatibility of ATY16, PT6 and PT26A with soil applied SAR inducers ASM and INA showed that these three bacteria could survive well at a 10-20 ppm concentration that is usually applied under field conditions. After 1 hour of exposure to UV radiation, there were less reduction in numbers of surviving cells of the bacterial strain incubated with 0.2% or 0.3% lignin, compared with the control. See Table 4. The results suggested that the (UV) protectant tested may be integrated to the bacterial formulations to enhance the resistance to UV. Lg=Log 10.

TABLE 4

Influence of UV protectant on ATY16, PT6 and PT26A exposed to UV.

| Treatment | Lg (cfu/mL) 1 hour after UV exposure | | % Lg (cfu/mL) change due to UV exposure |
|---|---|---|---|
| | No UV | UV | |
| ATY16 + 0.2% lignin | 6.41 a | 4.87 a | −24.1 |
| ATY16 + 0.3% lignin | 6.33 a | 4.62 a | −27.1 |
| ATY16 control | 6.52 a | 2.47 b | −62.1 |
| PT6 + 0.2% lignin | 6.54 a | 4.66 a | −28.7 |
| PT6 + 0.3% lignin | 6.37 a | 4.75 a | −25.4 |
| PT6 control | 6.32 a | 2.85 b | −54.9 |
| PT26A + 0.2% lignin | 6.44 a | 4.36 a | −32.2 |
| PT26A + 0.3% lignin | 6.63 a | 4.55 a | −31.4 |
| PT26A control | 6.25 a | 2.74 b | −56.2 |

Note:
The means of three replicates were shown. Data with different letter in the same column are significantly different at P < 0.05 (Student's t-test).

The assays for compatibility of ATY16, PT6 and PT26A with SAR inducers SA, ASM and INA indicated that these three bacteria could survive well at a 10-20 ppm concentration that is usually applied under field conditions. Results obtained in the present study showed that bacterial cell numbers were almost the same when the cells were cultured in the presence of SA, ASM or INA (10 and 20 ppm) as the growth of the cells without SA, ASM or INA. See Table 5, below.

TABLE 5

Effect of SAR inducers on population survival of ATY16, PT6 and PT26A strain in LB medium after 24 h of incubation period.

| Treatment | cfu/mL | Treatment | cfu/ml | Treatment | cfu/mL |
|---|---|---|---|---|---|
| ATY16 alone | $2.5 \times 10^8$ a | PT6 alone | $5.4 \times 10^{10}$ a | PT26A alone | $3.2 \times 10^{10}$ a |
| ATY16 + SA (10 ppm) | $1.8 \times 10^8$ a | PT6 + SA (10 ppm) | $3.5 \times 10^{10}$ a | PT26A + SA (10 ppm) | $2.4 \times 10^{10}$ a |
| ATY16 + SA (20 ppm) | $1.9 \times 10^8$ a | PT6 + SA (20 ppm) | $4.4 \times 10^{10}$ a | PT26A + SA (20 ppm) | $2.5 \times 10^{10}$ a |
| ATY16 + ASM(10 ppm) | $2.2 \times 10^8$ a | PT6 + ASM (10 ppm) | $3.9 \times 10^{10}$ a | PT26A + ASM (10 ppm) | $2.7 \times 10^{10}$ a |
| ATY16 + ASM (20 ppm) | $2.7 \times 10^8$ a | PT6 + ASM (20 ppm) | $4.8 \times 10^{10}$ a | PT26A + ASM (20 ppm) | $2.2 \times 10^{10}$ a |
| ATY16 + INA (10 ppm) | $2.1 \times 10^8$ a | PT6 + INA (10 ppm) | $4.5 \times 10^{10}$ a | PT26A + INA (10 ppm) | $3.9 \times 10^{10}$ a |
| ATY16 + INA (20 ppm) | $2.4 \times 10^8$ a | PT6 + INA (20 ppm) | $3.7 \times 10^{10}$ a | PT26A + INA (20 ppm) | $2.6 \times 10^{10}$ a |

Note:
The means of three replicates were shown. Data with different letter in the same column are significantly different at P < 0.05 (Student's t-test).

Example 3. Bacterial Tolerance to Stresses

A series of experiments were conducted to test bacterial tolerance of ATY16, PT6, and PT26A to heat shock, saline stress, and heavy metal (copper) stress. The assays were performed as described previously in the art, with modifications. Bacterial cultures at mid-exponential stage in LB were used to test survival under the aforementioned stresses. In each stress treatment, cell viability was determined by plate-counting of CFU. The survival rate was defined as the percentage of viable cell counts from the culture with stress treatment compared with those from the non-treated culture. The stress treatments were applied as follows: for heat-shock stress, the culture was transferred to 50° C. for 15 min (30° C. used as control); for sodium stress, NaCl was added to the bacterial culture at a final concentration of 5.0% (w/v) and incubated at 28° C. for 30 min; and then survival was estimated respectively. Copper stress assays were conducted by growing the tested bacterium in NB broth medium with different concentrations of $CuSO_4$. The growth of each strain was monitored by measuring the optical density at 600 nm after growth for 48 hours at 28° C. without shaking. Each stress test was repeated three times with three replicates each time. Student's t-test was used to test the significance of the difference. The copper resistant bacterium *Xanthomonas citri* subsp. *citri* strain A44 [XacA44(Cu—R) and copper sensitive bacterium X. cirri subsp. *citri* strain 306 [Xac306 (Cu—S) were used as positive and negative control respectively.

Figure 2:
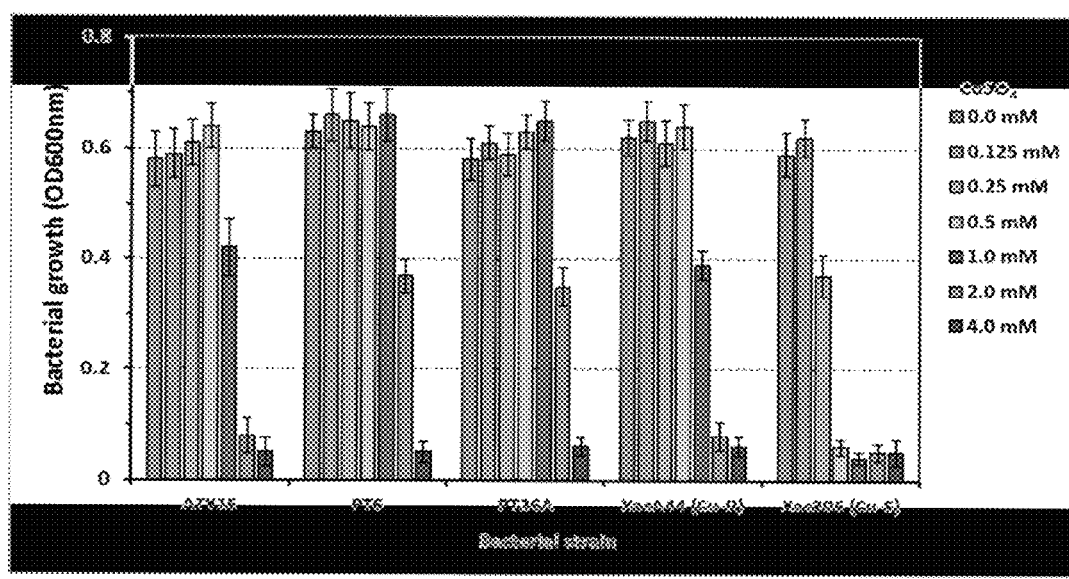
FIG. 2 is a graph showing the growth of bacterial strains under copper stress.

The results showed that ATY16 can resist 1.0 mM of $CuSO_4$, while PT6 and PT26A can resist 2.0 mM of $CuSO_4$ in nutrient broth (NB) (BD, Sparks, Md., USA). After 48 hours growth in NB with 1.0 mM of $CuSO_4$, the bacterial growth (optical density (OD) at 600 nm) of ATY16 was the same as the copper resistant bacterium *Xanthomonas citri* subsp. *citri* strain A44, and PT6 and PT26A was at a higher level than strain A44. See FIG. 2. In the case of 2.0 mM $CuSO_4$, the bacterial growth of PT6 and PT26A was also at a higher level than strain A44. These results suggested that ATY16, PT6, and PT26A can survive after release into the citrus groves, where copper formulations were usually applied to control plant diseases.

These assays revealed that ATY16, PT6, and PT26A was of certain tolerance to heat shock. Following 15 minutes of exposure of bacteria to heat (50° C.), which was thought able to kill most bacterial cells, there were about 0.5% of ATY16, about 1.0% of PT6 and PT26A viable cells in the broth medium. See Table 6, below.

TABLE 6

Survival of bacterial strains under heat stresses.

| Heat treatment | Bacterial survival (%) after challenge | | |
|---|---|---|---|
| (15 min) | ATY16 | PT6 | PT26A |
| 30° C. | 98.2 ± 4.6 a | 102.1 ± 5.3 a | 101.7 ± 4.8 a |
| 50° C. | 0.43 ± 0.25 b | 1.38 ± 0.36 b | 1.16 ± 0.35 b |

Note:

Data in the same column with different letters denote significant difference (P < 0.05; Student's t-test).

These assays also indicated that ATY16, PT6, and PT26A was of certain tolerance to salt stress. After 30 minutes of exposure of bacteria to 5.0% (wt/vol) NaCl, which was thought able to kill most bacterial cells, there were about 40-50% of ATY16, PT6 and PT26A viable cells in the broth medium. See Table 7, below.

TABLE 7

Survival of bacterial strains under salt stresses.

| NaCl (wt/vol) | Bacterial survival (%) after challenge for 30 min | | |
|---|---|---|---|
| | ATY16 | PT6 | PT26A |
| 1.0% | 104.5 ± 5.7 a | 105.2 ± 6.1 a | 102.9 ± 4.5 a |
| 5.0% | 40.4 ± 4.2 b | 51.3 ± 3.8 b | 47.6 ± 5.1 b |

Note:
Data in the same column with different letters denote significant difference ($P < 0.05$; Student's t-test).

Example 4. Bacterial Compatibility Tests

Figure 3:
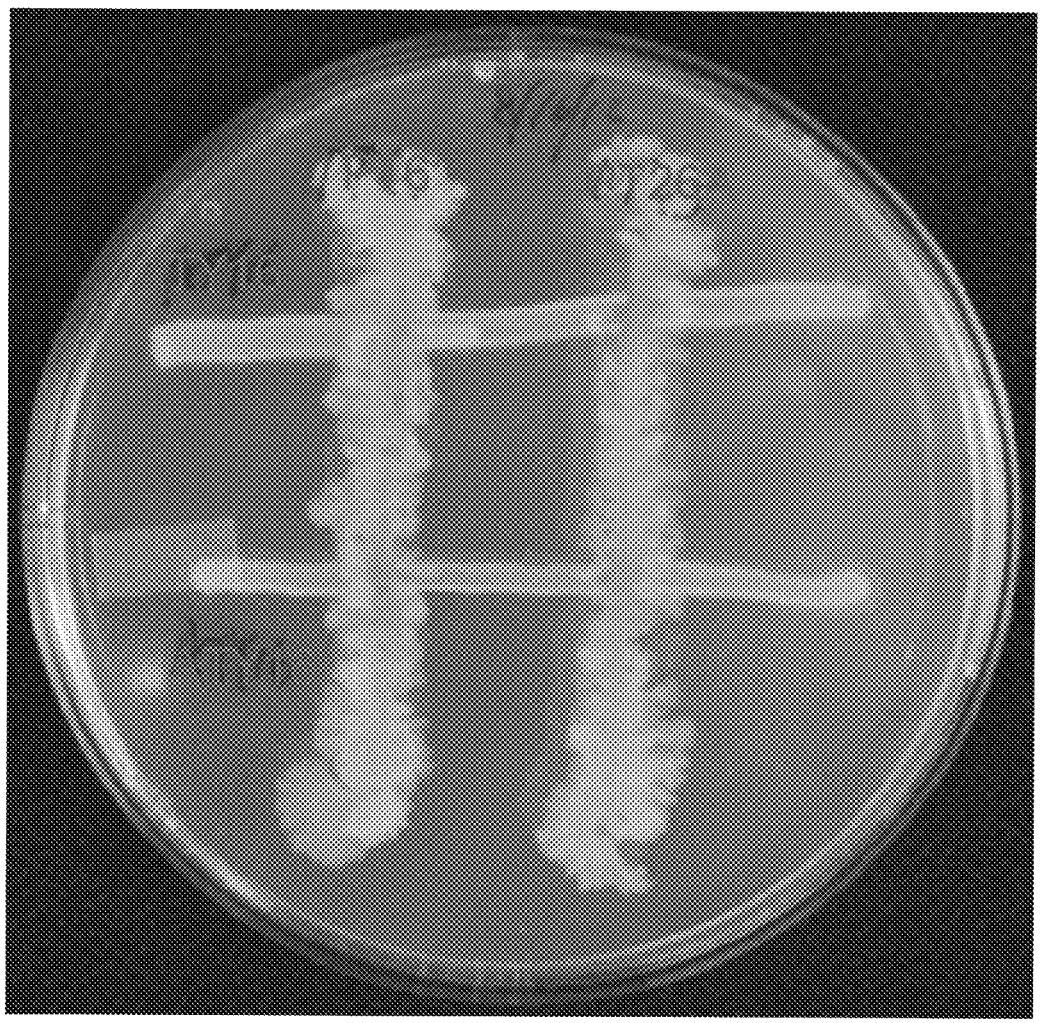
FIG. 3 is a photograph of an antagonistic survival test on a nutrient agar plate showing compatibility among bacterial isolates.

Bacterial combinations were tested for survival as follows. The three strains of ATY16, PT6, and PT26A were tested to be compatible with each other. Bacterial growth compatibility test was performed in vitro in Nutrient agar (NA) plates by cross-streaking a fresh culture of the two bacterial strains to be tested. Plates were incubated at 28° C. and results were photo recorded after 24 hours. The antagonistic survival tests on nutrient agar (NA) plates showed that these three bacteria, ATY16, PT6, and PT26A, can survive well with each other under the experiment conditions. No growth inhibition was observed after 24 hours post co-streaking on NA plates. There is no antagonistic effect between the bacterial isolates. See FIG. 3.

Example 5. Bacterial Survival on Roots

Grapefruit seedling plants were treated as follows. FIG. 4A shows a fluorescent microscopic analysis of the grapefruit seedling roots at five months after bacterial inoculation with the indicated bacterial strains expressing green fluorescent protein (GFP) as indicated. The bacteria were used to observe bacterial root colonization. FIG. 4B and FIG. 4C show data for bacterial survival for up to 224 days post inoculation. The bacteria therefore were long-lived and survived well after inoculation.

Example 6. Bacterial Colonization of Citrus Root and Rhizosphere

Rifamycin resistance was used as the antibiotic selection marker to track the bacteria following application. The spontaneous rifamycin resistance of the bacterium was obtained using a gradient-inducing method as described elsewhere.

For greenhouse test, the spontaneous rifamycin resistant mutant of bacterial strains was grown under optimal conditions (28° C. and 180 rpm) for 24 hours in LB medium with rifamycin (50 μg/mL) and diluted with fresh sterile LB medium to OD (600 nm)=0.3, equivalent to approximately $5 \times 10^8$ cfu/mL. Roots from 60 day-old citrus seedlings (Grapefruit) were carefully washed under a stream tap water to remove potting media, inoculated in bacterial suspensions for 60 minutes and transplanted into 0.5-liter pots containing sterile soil. Plants were transferred to a greenhouse as previously described. Once a week, the root systems of five independent plants initially inoculated with bacterial strains were collected and the roots and rhizospheric soil carefully separated, weighted and homogenized in sterile saline and platted on NA-agar plates with rifamycin (50 μg/mL) as described above. Finally, abundance of bacterial strains on root surfaces and in rhizospheric soil was expressed as log cfu/g fresh root weight and log cfu/g wet soil weight respectively.

Figure 5A:
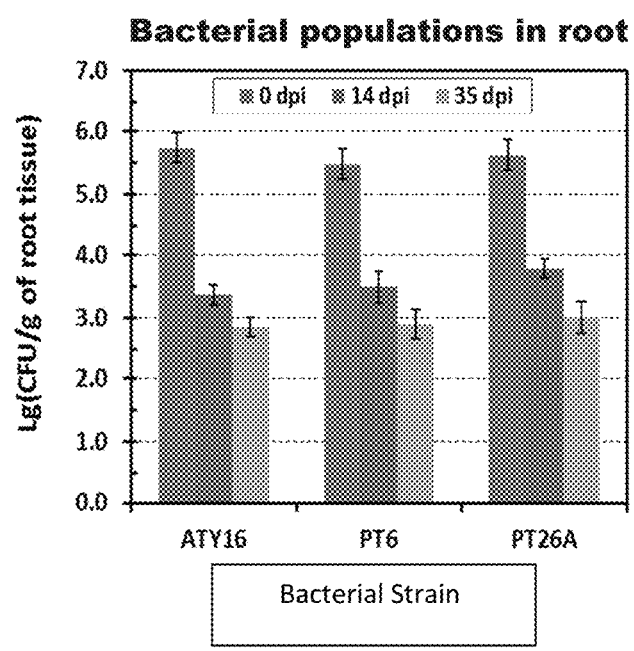
FIG. 5A is a graph showing colonization of root of citrus by bacterial inoculants under field conditions.
Figure 5B:
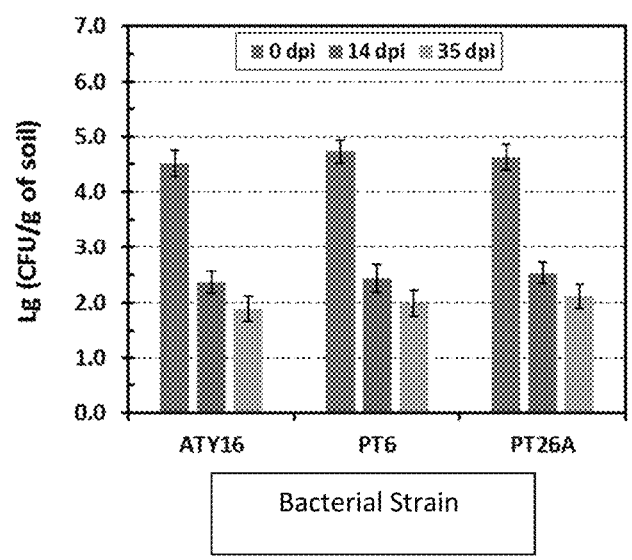
FIG. 5B is a graph showing colonization of rhizosphere of citrus by bacterial inoculants under field conditions.

For field experiments, the bacterial cultures ($5 \times 10^8$ cfu/mL) were applied as soil drench around the trunk of 6-year old Valencia sweet orange trees in a grove at CREC, Florida. Once a week, the root and rhizospheric soil samples from three trees were collected and bacterial populations were determined as described above. The data showed that these bacteria can establish a population of $10^4$-$10^5$ cfu/g root and $10^3$-$10^4$ cfu/g soil at one month after inoculation with an initial population of $10^5$-$10^6$ cfu/g root and $10^4$-$10^5$ cfu/g soil respectively in greenhouse. Under field conditions, these bacteria can establish a population of about $10^3$ cfu/g root and about $10^2$ cfu/g soil at one month after inoculation with an initial population of about $10^5$ cfu/g root and about $10^4$ cfu/g soil respectively. See FIG. 5.

Example 7. Tests Showing Plant Benefits for Bacterial Strains

The bacterial strains were cultured in Luria-Bertani (LB) broth at 28° C. with shaking at 180 rpm for 24 hours, then bacterial cells were collected by centrifugation (4000×g, 15 min). After subjecting the media to the conditions described above, they were tested for phosphate solubilization ability (P-sol) as an indicator of sufficient mineral nutrition; indole acetic acid production (IAA) as an indicator of plant development; siderophore production (Sid) as an indicator of sufficient mineral nutrition; antibiotic (antimicrobial) production (Anti-M) as an indicator of improved ability to defend against disease (antibiotic production was tested against several plant pathogenic fungi and bacteria including *Alternaria, Aspergillus, Fusarium, Rhizoctonia*, and the citrus canker bacterium *Xanthomonas citri* subsp. *Citri*); lytic enzyme production (Chitinase) as an indicator of production of antibiotic and lytic enzymes (plant health); salicylic acid production (SA) as an indication of systemic resistance induction and improved resistance to disease; nitrogen fixation (N-fix) as an indicator of nutritional health; and 1-aminocyclopropane-1-carboxylate deaminase production (ACCD) as an indicator of stress relief. The results showed that each of the three bacteria ATY16, PT6 and PT26A provided several effects that can be beneficial to plants, including phosphate solubilization ability, production of IAA, producing salicylic acid, nitrogen fixation ability, and producing ACC deaminase, and production of antibiotics against several pathogenic fungi and bacteria (including *Alternaria, Aspergillus, Fusarium, Rhizoctonia*, and the citrus canker bacterium *Xanthomonas citri* subsp. *citri*,). See Table 8, below. "+" indicates the presence of trait; "−" indicates the absence of trait.

TABLE 8

Plant growth promotion and biocontrol activities of selected bacteria

| Bacterial strains | Plant beneficial traits | | | | | | | |
|---|---|---|---|---|---|---|---|---|
| | P-sol | IAA | Sid | Anti-M | Chitinase | SA | N-fix | ACCD |
| ATY16 | + | + | + | + | + | + | + | − |
| PT6 | + | + | + | + | + | − | − | + |
| PT26A | + | + | + | + | + | − | − | + |

The above strains were isolated from a federal citrus farm belonging to the USDA Horticultural Research Laboratory, 2001 South Rock Road, Fort Pierce, FL 34945.

Figure 6A:
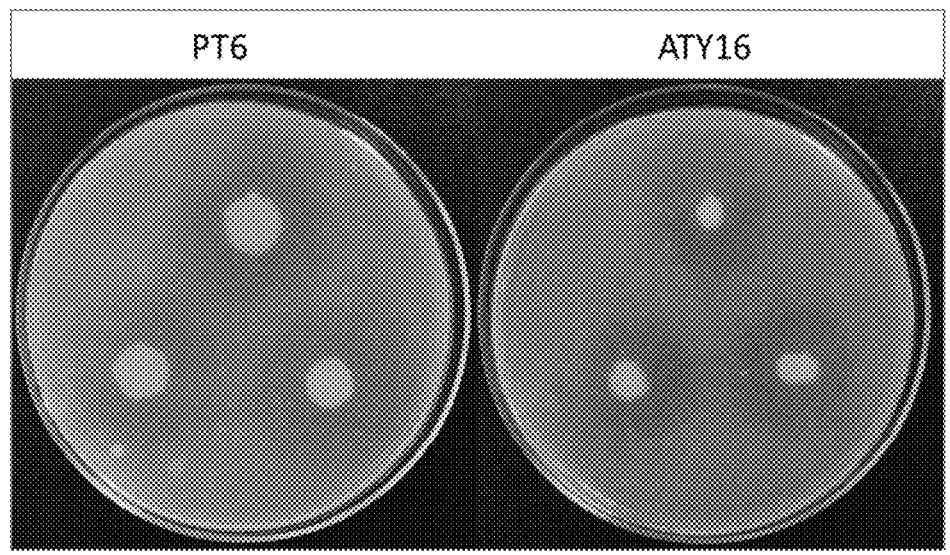
FIG. 6A shows the inhibitory effect of PT6 (left plate) and ATY16 (right plate) against the plant bacterium *Sinorhizobium melilori* 1021 on LB agar plates.

See FIG. 6 for data on activity against plant pathogenic fungi and bacteria. For FIG. 6A, a drop of 10 μL tested bacterial cell suspension (about $10^9$ cfu/mL) (three replicates) was inoculated onto an agar plate and incubated at 28°

Figure 6B:
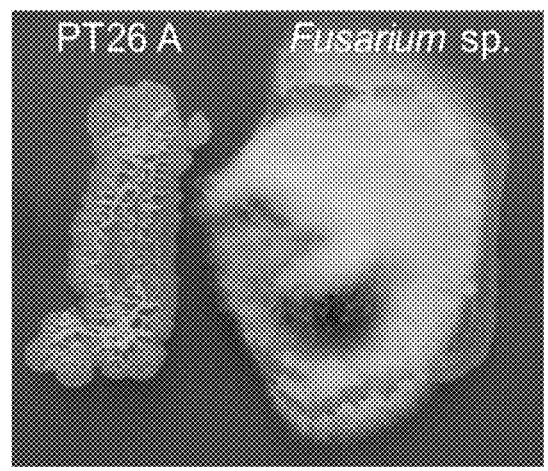
FIG. 6B shows the inhibitory effect of PT26A against plant pathogenic *Fusarium* sp. on a potato détox agar (PDA) plate.

C. for 3 days. Then the bacterial cells were killed with chloroform vapors. After evaporation of the chloroform, 5 mL of 0.7% nutrient broth soft agar containing 50 μL aliquots of *S. meliloti* target 1021 (about $10^8$ cfu/mL) was poured evenly over the surfaces of the agar plate. The plate was incubated at 28° C. for 48 hours, and the inhibition zone around the killed bacterial colony was observed. FIG. 6B shows similar results for plant pathogenic fungus, *Fusarium* species.

Example 8. Treatment Effects on HLB Infection in Citrus

Two-year old potted Valencia sweet orange (*Citrus sinensis*) plants were trimmed about 3 weeks prior to bacterial inoculation to get new flushes. Once new flush emarginated, the plants were immediately covered with an insect proof cage, transferred to a secured greenhouse at CREC, FL, and exposed to HLB-infected psyllids for HLB inoculation. Then bacterial cultures (ATY16, PT6 and PT26A) were applied in a single application per month as a soil drench (500 mL of $5 \times 10^8$ cfu/mL solution per pot). The plants were checked monthly for HLB symptoms and Las quantification using qPCR analysis (Trivedi et al. 2011). The experiments were carried out in triplicate and tap water was used as non-treated control. The plants were analyzed for effects on growth of the HLB causative bacterium as determined by qPCR. See Example 1 for molecular biological methods. Ct values (cycle threshold values and Las titers are reported for each bacterial strain at 0, 90 and 120 days after treatment (DAT). See Table 9, below. The results showed that the three bacteria ATY16, PT6 and PT26A delayed the development of HLB symptoms and Las populations in new flushes of citrus plants exposed to HLB infected psyllids in greenhouse assays over a period of 4 months.

TABLE 9

Effect of Bacterial Treatment on HLB bacterial titer in *Citrus* by qPCR[a]

| Treatment | Ct value | | | Las titer (cells/g plant tissue) | | |
|---|---|---|---|---|---|---|
| | 0 DAT | 90 DAT | 120 DAT | 0 DAT | 90 DAT | 120 DAT |
| CK (control) | ND | 25.36 | 24.79 | ND | $2.13 \times 10^4$ | $0.72 \times 10^6$ |
| ATY16 | ND | ND | ND | ND | ND | ND |
| PT6 | ND | 31.64 | 30.24 | ND | $3.09 \times 10^2$ | $0.69 \times 10^4$ |
| PT26A | ND | ND | 32.87 | ND | ND | $1.02 \times 10^2$ |

[a] qPCR and Las titer assays were performed as described by Trivedi et al (2009).
Ct value >32.00 is considered negative or not detected (ND) for Las.
DAT: days after the first treatment.

Example 9. Treatment Effects on Development of HLB Symptoms

Figure 7:
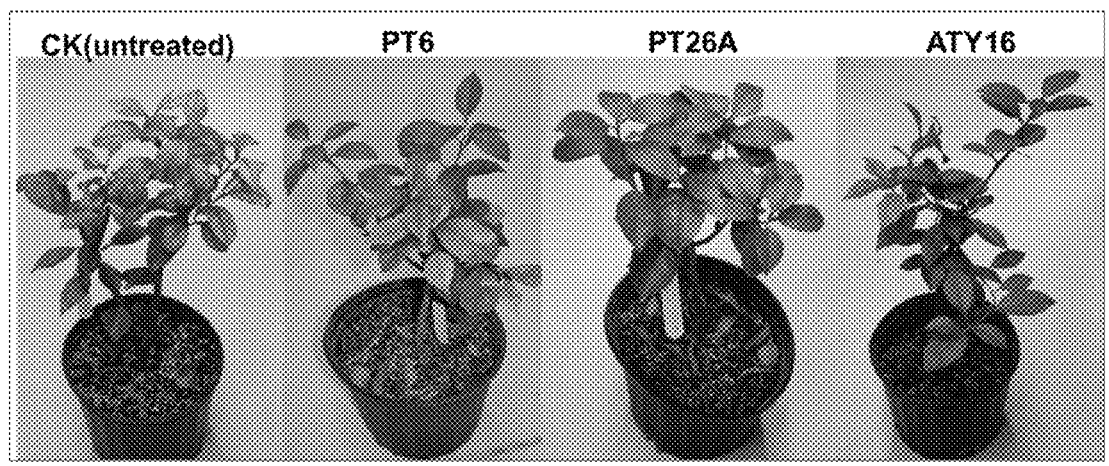
FIG. 7 is a photograph of Valencia sweet orange plant phenotypes after exposure to HLB-affected psyllids for 90 days in greenhouse, with the indicated treatments (control (CK) untreated, PT6, PT26A and ATY16).
Figure 8A:
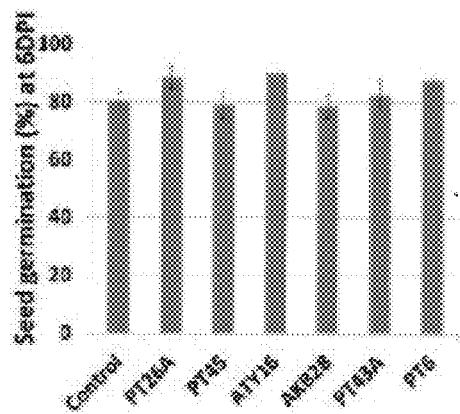
FIG. 8A provides data showing the ability of bacterial strains according to embodiments of the invention ($10^8$ cells/mL) to promote see germination at 6 days post inoculation (DPI).
Figure 8B:
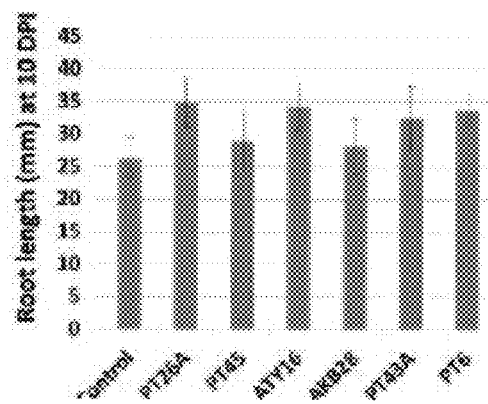
FIG. 8B provides data showing the ability of bacterial strains according to embodiments of the invention ($10^8$ cells/mL) to promote root length growth at 10 DPI.
Figure 8C:
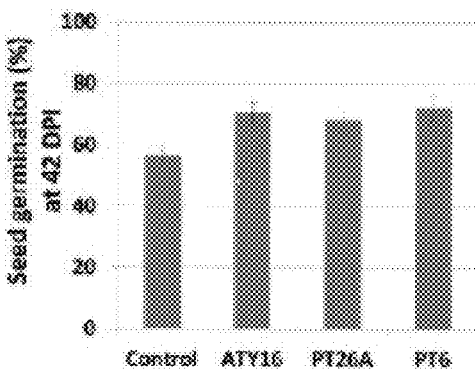
FIG. 8C shows the ability of bacterial strains according to embodiments of the invention to promote seed germination at 42 DPI.
Figure 8D:
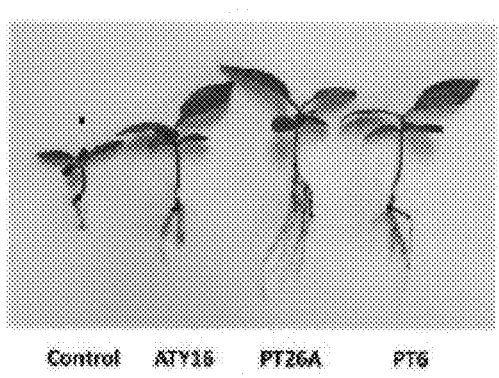
FIG. 8D shows a photograph of seedlings that were inoculated with select bacterial strains.

PT6, PT26A and ATY16 bacteria also delayed the development of HLB symptoms. Plants were treated as follows. Two-year old potted Valencia sweet orange (*Citrus sinensis*) plants were trimmed about 3 weeks prior to bacterial inoculation to get new flushes. Once new flush emarginated, the plants were immediately covered with an insect proof cage, transferred to a secured greenhouse at CREC, FL, and exposed to HLB-infected psyllids for HLB inoculation. Then bacterial cultures were applied in a single application per month as a soil drench (500 mL of $5 \times 10^8$ cfu/mL solution per pot). The plants were checked monthly for HLB symptoms and Las quantification using qPCR analysis (Trivedi et al. 2011). The experiments were carried out in triplicate and tap water was used as non-treated control. See FIG. 7, which shows Valencia sweet orange plant phenotypes after exposure to HLB-affected psyllids for 90 days in a greenhouse, with the indicated treatments (control (CK) untreated, PT26A and ATY16).

Example 10. Treatment Effects on *Arabidopsis* and Citrus Germination and Seedling Growth A series of experiments were conducted to determine the germination responses of *Arabidopsis*, citrus, corn, soybean and tomato seeds to plant beneficial bacteria inoculation. Seeds were inoculated with different bacterial strains of *B. megaterium* PT6, *B. subtilis* PT26A, and *Paenibacillus* sp. ATY16. *Arabidopsis* and Citrus seeds were treated as follows.

For assays with *Arabidopsis*, sterile Petri dish (150 mm diameter) containing 40 mL autoclaved water agar (0.65%) was used for seed germination. Petri dishes were partially sealed with parafilm to prevent water loss from evaporation. The set up was repeated three times with 40 seeds per replicate and arranged in a completely randomized design with three replications. The experiments were conducted in a light and temperature-controlled growing cabinet with a constant temperature of 28° C. and a daily cycle of 12 hours each light and darkness.

For assays with citrus (*Citrus paradisi* 'Duncan' Grapefruit), Deepot cells (containers) containing sterilized Metro-Mix professional growing soil was used for seed germination in a quarantine greenhouse at the Citrus Research and Education Center, Lake Alfred, Fla. The greenhouse was maintained at approximately 25-30° C. and 60% relative humidity. *Arabidopsis* and citrus seeds were surface sterilized using 1% NaClO and 70% ethanol. Seeds then were washed with autoclaved Millipore water four times to remove the residual bleach and ethanol.

Inoculum of each strain of ATY16, PT6, and PT26A was taken from a pure culture stored with glycerol at −80° C. and streaked onto the nutrient agar plate and incubated at 28° C. for 2 days. A loop full of each culture was transferred separately into the nutrient broth (25 mL) (for ATY16, with added 0.5% yeast extract and 0.5% xylan) and incubated for 16 hours at 28° C. with constant agitation (180 rpm). Prior to inoculation, bacterial cultures were pelleted by centrifugation (4000×g, 15 min), washed with autoclaved 0.85% (w/v) NaCl, and resuspended in the same buffer solution. The number of colony forming unit (cfu) was determined after series of dilution and agar plating. Seeds were inoculated at population log 8-9 cfu/mL by soaking the surface sterilized seeds in bacterial suspension for 1 hour to allow bacteria bind to the seed coat and for seed imbibition. A similar procedure was used for the control except seeds were soaked in buffer solution. Inoculated *Arabidopsis* seeds were spread out in a sterile Petri dish with autoclaved water agar (0.65%), and grapefruit seeds planted in the Deepot cells and maintained in the greenhouse.

The plant seeds were analyzed for seed germination and seedling growth (root length). See FIG. 8 for results.

The results showed that the three bacteria ATY16, PT6 and PT26A are able to promote seed germination and seedling growth of *Arabidopsis* in vitro; and increase seedling emergence and growth of citrus in greenhouse, with stronger root systems. The results also revealed that PT26A was able to promote seed germination and seedling growth of corn, soybean and tomato in vitro. Corn, soybean and tomato started to germinate on the following day post inoculation (DPI). Corn reached maximum germination 4 days from sowing while soybean and tomato reached peak germination after 3 days.

See FIG. 8 which shows the ability of bacterial strains according to embodiments of the invention ($10^8$ cells/mL) to promote *Arabidopsis* (FIG. 8 and FIG. 8B) and citrus (grapefruit) (FIG. 8C and FIG. 8D) growth under in vitro and greenhouse conditions respectively. DPI: days post inoculation of beneficial bacteria.

Example 11. Seed Treatments

Seeds were germinated as follows: a sterile petri dish (150 mm diameter) containing 40 mL autoclaved water agar (0.65%) was used for seed germination. Petri dishes were partially sealed with parafilm to prevent water loss from evaporation. This set-up was repeated three times with 40 seeds per replicate, completely randomized with three replications. The experiments were conducted in a light and temperature-controlled growing cabinet with a constant temperature of 28° C. and a daily cycle of 12 hours each of light and darkness.

Corn, soybean and tomato seeds were surface sterilized using 1% NaClO and 70% ethanol. Seeds were then washed with autoclaved Millipore water four times to remove the residual bleach and ethanol.

An inoculum of each strain of *Bacillus megaterium* PT6, *Bacillus subtilis* PT26A, and *Paenibacillus* sp. ATY16 was taken from a pure culture stored with glycerol in −80° C. and streaked onto the nutrient agar and incubated at 28 C for 2 days. A loop full of each culture was transferred separately into the nutrient broth (25 mL), and incubated for 16 hours at 28° C. with constant agitation (180 rpm). Prior to inoculation, bacterial cultures were pelleted by centrifugation (4000×g, 15 min), washed with autoclaved 0.85% (w/v) NaCl, and resuspended in the same buffer solution. The number of colony forming unit (cfu) was determined after series of dilution and agar plating. Seeds were inoculated at population log 8-9 cfu/mL by soaking the surface sterilized seeds in bacterial suspension for 1 hour to allow bacteria bind to the seed coat and for seed imbibition. A similar procedure was used for control except seeds were soaked in buffer solution.

Daily germination was recorded and the germination rate (percent germinated seeds) was calculated. Seedlings from germinated seeds were weighed at the final day of the experiment. Student's t-test ($P<0.05$) was used to test the significance of the mean differences.

Figure 9A:
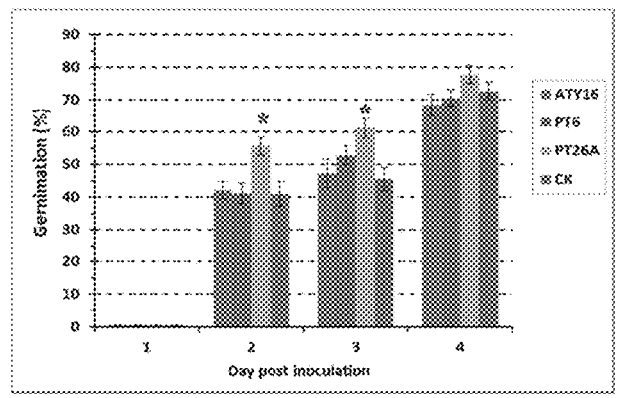
FIG. 9A presents data showing germination of corn (FIG. 9A) seeds at different days post inoculation with plant beneficial bacteria. The asterisk denotes significant difference (P<0.05, t-test) compared with the untreated control. Error bars indicate standard error. ATY16, PT6 and PT26A are bacterial strains of *Paenibacillus* sp., *Bacillus megaterium*, and *Bacillus subtilis* respectively. CK: untreated control.
Figure 9B:
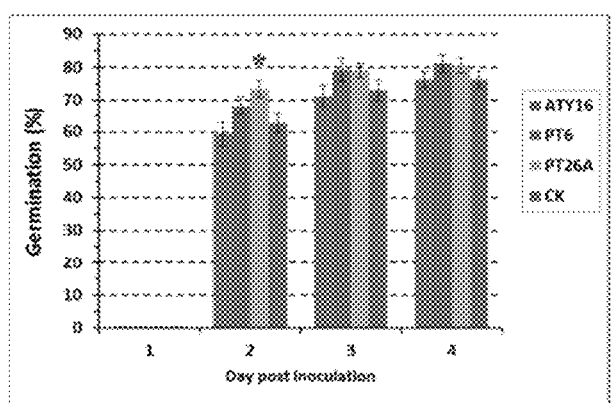
FIG. 9B present data showing germination of soybean seeds at different days post inoculation with plant beneficial bacteria. The asterisk denotes significant difference (P<0.05, t-test) compared with the untreated control. Error bars indicate standard error. ATY16, PT6 and PT26A are bacterial strains of *Paenibacillus* sp., *Bacillus megaterium*, and *Bacillus subtilis* respectively. CK: untreated control.
Figure 9C:
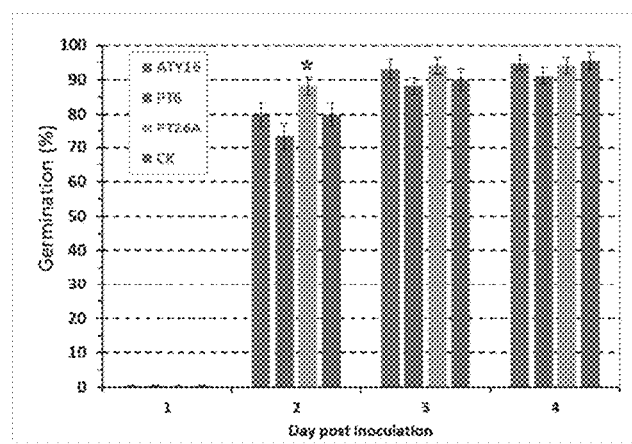
FIG. 9C presents data showing germination of tomato seeds at different days post inoculation with plant beneficial bacteria. The asterisk denotes significant difference (P<0.05, t-test) compared with the untreated control. Error bars indicate standard error. ATY16, PT6 and PT26A are bacterial strains of *Paenibacillus* sp., *Bacillus megaterium*, and *Bacillus subtilis* respectively. CK: untreated control.
Figure 10A:
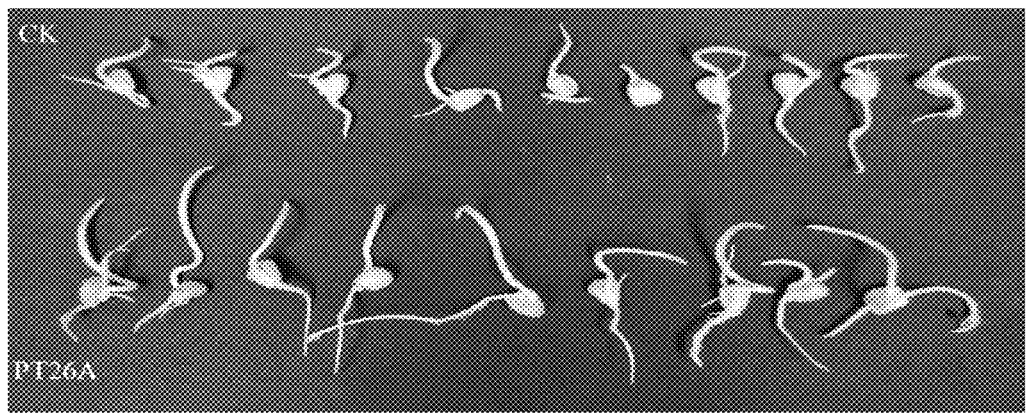
FIG. 10A shows seedlings of corn (at 4 days post inoculation of seeds with *Bacillus subtilis* PT26A. CK: untreated control.
Figure 10B:
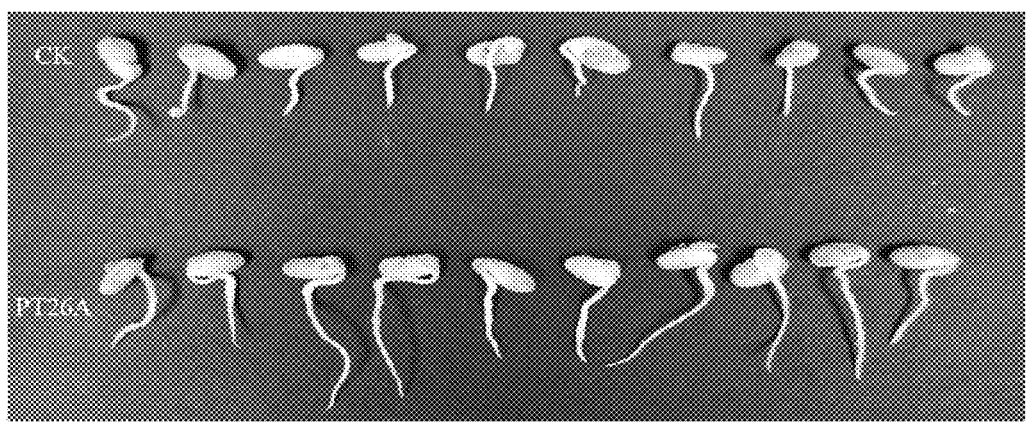
FIG. 10B shows seedlings of soybean at 4 days post inoculation of seeds with *Bacillus subtilis* PT26A. CK: untreated control.
Figure 10C:
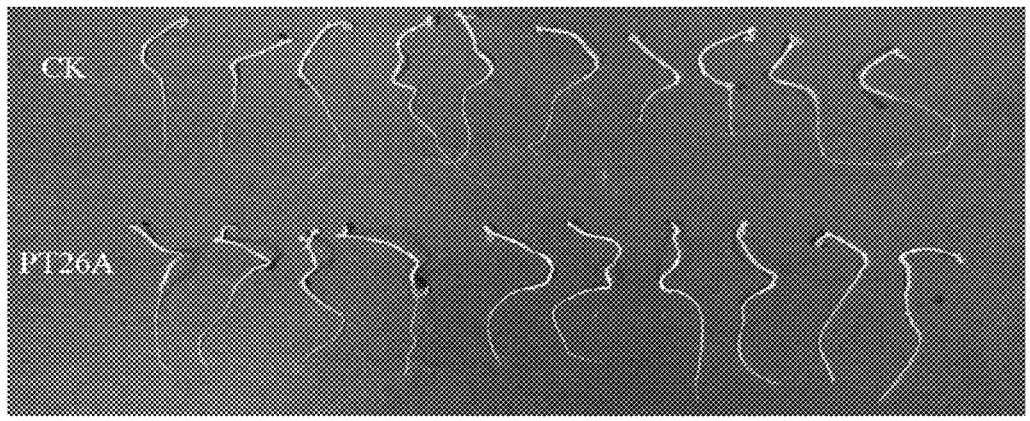
FIG. 10C shows seedlings of tomato at 4 days post inoculation of seeds with *Bacillus subtilis* PT26A. CK: untreated control.

Among the three bacterial strains tested, PT26A was able to promote seed germination and seedling growth of corn, soybean and tomato in vitro. Corn, soybean and tomato started to germinate on the following day post inoculation (DPI). Corn reached maximum germination 4 days from sowing whiles soybean and tomato reached peak germination after 3 days. Regardless of the crops, seeds inoculated with the bacterial strain PT26A generally germinated earlier and faster than non-inoculated ones, with a higher total germination at 2 days post inoculation (DPI); whereas inoculation with ATY16 or PT6 did not affect corn, soybean or tomato seed germination (FIG. 9A, FIG. 9B, and FIG. 19C). ATY16, PT6 and PT26A are bacterial strains of *Paenibacillus* sp., *Bacillus megaterium*, and *Bacillus subtilis* respectively. CK: untreated control. See also FIG. 10, which shows photographs of representative seedlings of corn (FIG. 10A, soybean (FIG. 10B), and tomato (FIG. 10C) at 4 days post inoculation of seeds with *Bacillus subtilis* PT26A. PT26A inoculation also improved the vigor of germinating seeds of the three crops. PT26A-inoculated corn and tomato seeds produced heavier seedlings compared to non-inoculated control. See FIG. 10.

Figure 11A:
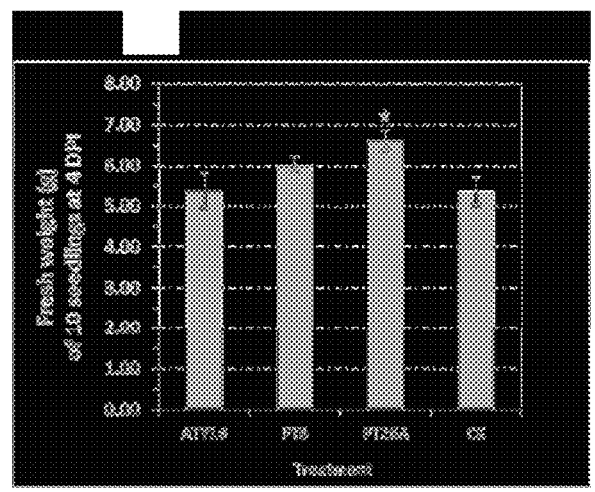
FIG. 11A shows the seedling fresh weight of corn at 4 days post inoculation of seeds with plant beneficial bacteria. The asterisk denotes significant difference (P<0.05, t-test) compared with the untreated control. Error bars indicate standard error. ATY16, PT6 and PT26A are bacterial strains of *Paenibacillus* sp., *Bacillus megaterium*, and *Bacillus subtilis* respectively. CK: untreated control.
Figure 11B:
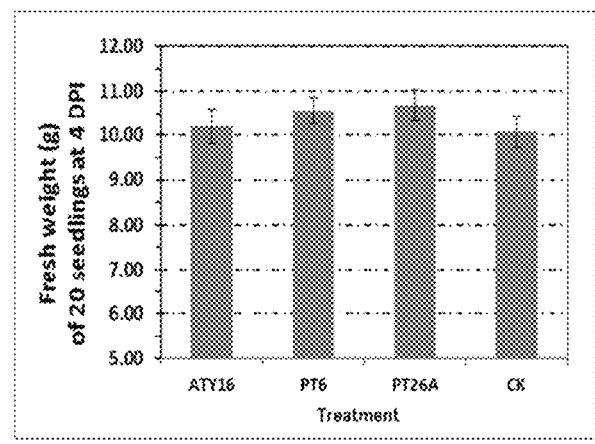
FIG. 11B shows the seedling fresh weight of soybean at 4 days post inoculation of seeds with plant beneficial bacteria. The asterisk denotes significant difference (P<0.05, t-test) compared with the untreated control. Error bars indicate standard error. ATY16, PT6 and PT26A are bacterial strains of *Paenibacillus* sp., *Bacillus megaterium*, and *Bacillus subtilis* respectively. CK: untreated control.
Figure 11C:
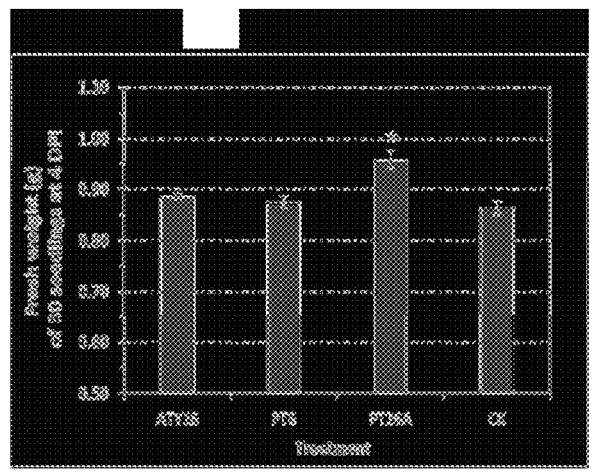
FIG. 11C shows the seedling fresh weight of tomato at 4 days post inoculation of seeds with plant beneficial bacteria. The asterisk denotes significant difference (P<0.05, t-test) compared with the untreated control. Error bars indicate standard error. ATY16, PT6 and PT26A are bacterial strains of *Paenibacillus* sp., *Bacillus megaterium*, and *Bacillus subtilis* respectively. CK: untreated control.

PT26A inoculation also improved the vigor of germinating seeds of the three crops. PT26A-inoculated corn and tomato seeds, produced heavier seedlings compared to non-inoculated control (FIG. 11A, FIG. 11B and FIG. 11C). ATY16, PT6 and PT26A are bacterial strains of *Paenibacillus* sp., *Bacillus megaterium*, and *Bacillus subtilis* respectively. CK: untreated control.

Example 12. Field Trials for Estimation of Citrus Productivity Improvement

The experiments of this study were performed in two citrus groves at Lake Wales, Fla. The first grove, subsequently noted as Mck block#15, was planted with Valencia sweet orange [*Citrus sinensis* (L.) Osbeck] Blanco] on Swingle citrumelo [*Citrus paradisi* Macf. "Duncan" grapefruit x *Poncirus trifoliata* (L.) in 2009. The second grove, subsequently noted as Hunt block#23, was planted with Murcott mandarin [*Citrus reticulata* (L.) Blanco] on Cleopatra mandarin [*Citrus reticulata* (L.) Blanco] rootstock in 2003. In each grove, the HLB disease severity was inspected and 20 HLB diseased trees were randomly selected for the study. A mixture of ATY16, PT6 and PT26A bacterial cultures ($5×10^9$ cfu/mL each) was applied monthly as a soil drench at 4.0 liters/tree to the soil surface in a crescent within 25 to 50 cm of the trunk on the top side of the bed to minimize runoff. The other 10 trees were provided water only as a non-treated control. Following the first application, the HLB disease severity and Las population was determined tri-monthly using visual inspection (Gottwald et al., 2007) and qPCR analysis (Trivedi et al., 2011) respectively.

Figure 12A:
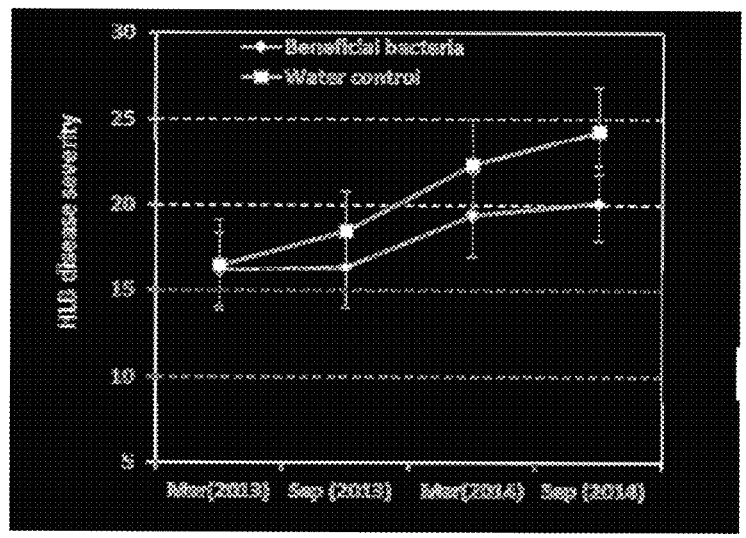
FIG. 12A presents HLB disease severity progress under treatment or control, in field trials at Hunt block#23 from March 2013 to September 2014.
Figure 12B:
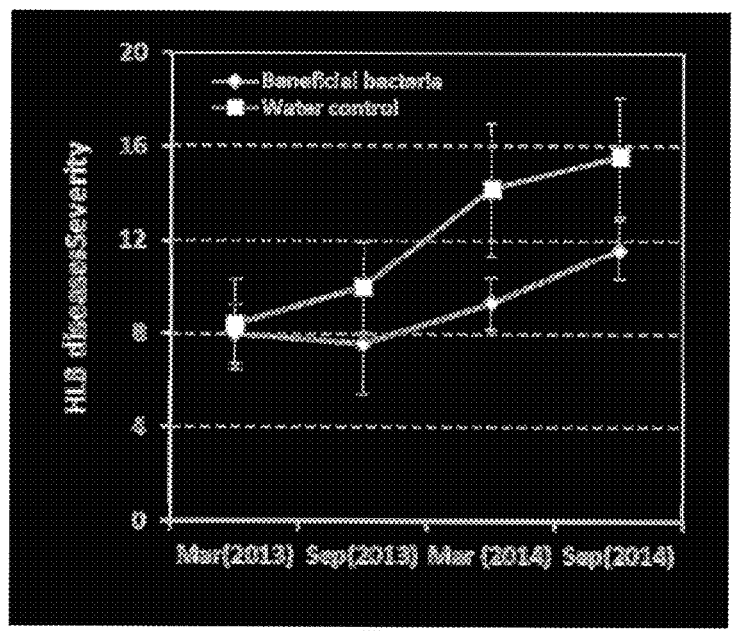
FIG. 12B presents HLB disease severity progress under treatment or control, in field trials at Mck block#15 from March 2013 to September 2014.

The data collected showed that applications of a consortium of the three beneficial bacteria ATY16, PT6 and PT26A reduces the HLB disease progress and slows the pathogen population growth, compared with the non-treated control in the field trial with mild HLB affected citrus trees. See FIG. 12 and Tables 10 and 11, below. Table 11 provides bacterial titers in citrus subjected to different treatments in field trial Mck block#15, using mildly HLB-affected citrus trees, determined by qPCR. The qPCR and Las titers assays were performed as described by Trivedi et al., 2009 (see Example 1). The means with standard errors of 10 replicates are shown. In both tables below, data shown with a different letter in the same column are significantly different at $P<0.05$ (Student's t-test).

TABLE 10

Area under Disease Progress Curve (AUDPC) in Field Trials.

| | AUDPC | |
|---|---|---|
| Treatment | Hunt block# 23 | Mck block#15 |
| Water control | 335.7 a | 217.2 a |
| Beneficial bacteria ($10^{9-10}$ | 326.1 a | 160.2 b |

TABLE 11

HLB Pathogenic Bacterial Titers in *Citrus*.

| Treatment | Las titer ($\times 10^5$ cells per gram of leaf tissue) | | | |
|---|---|---|---|---|
| | March 2013 | September 2013 | March 2014 | September 2014 |
| Water control | 0.55 ± 0.14 a | 0.35 ± 0.07 a | 1.23 ± 0.29 a | 2.51 ± 0..49 a |
| Bacteria ($10^{9-10}$ cfu/mL) | 0.23 ± 0.03 a | 0.15 ± 0.03 a | 0.38 ± 0.06 b | 0.68 ± 0.13 b |

6. References

All patents, patent applications, patent publications, technical publications, scientific publications, and other references referenced herein are hereby incorporated by reference in this application to the extent they are not inconsistent with the teachings herein. In particular, the following references are hereby incorporated by reference in their entirety.

1. Auber, 1990. Integrated activities for the control of Huanglongbing-greening and its vector *Diaphorina citri* Kuwayama in Asia. Pages 133-144 in: Rehabilitation of Citrus Industry in the Asia Pacific Region. Proc. Asia-Pac. Int. Conf. Citri Culture. B. Aubert, S. Tontyaporn, and D. Buangsuwon, eds. Chiang Mai, Thailand.
2. Aziz et al., 2008. The RAST server: Rapid Annotations using Subsystems Technology. BMC Genomics 9:75.
3. Bashan, 1986 Alginate beads as synthetic inoculant carriers for slow release of bacteria that effect plant growth. Applied and Environmental Microbiology 51, 1098-1098.
4. Bové, 2006. Huanglongbing: a destructive, newly-emerging, century old disease of citrus. J. Plant Pathol. 88:7-37.
5. Duan et al., 2009. Complete genome sequence of citrus huanglongbing bacterium, '*Candidatus Liberibacter asiaticus*' obtained through metagenomics. Mol. Plant-Microbe Interact. 22:1011-1020.
6. Durrant and Dong, 2004. Systemic acquired resistance. Annu. Rev. Phytopathol. 42: 185-209.
7. Gottwald et al., 2007. Citrus huanglongbing: the pathogen, its epidemiology, and impact. Plant Health Prog. http://www.plantmanagementnetwork.org/sub/php/review/2007/huanglongbing/.
8. Gottwald, 2010. Current epidemiological understanding of citrus Huanglongbing. Annu. Rev. Phytopathol. 48:119-139.
9. Gottwald et al., 2012. Inconsequential effect of nutritional treatments on huanglongbing control, fruit quality, bacterial titer and disease progress. Crop protection 36: 73-82.
10. Graham et al., 2012. Protection of citrus roots against infection by *Phytophthora* spp. By hypovirulent *P. nicotianae* is not related to induction of systemic acquired resistance. Plant Soil 358:39-49.
11. Kim et al., 2009. Response of sweet orange (*Citrus sinensis*) to '*Candidatus Liberibacter asiaticus*' infection: Microscopy and microarray analyses. Phytopathology 99:50-57.
12. Leonard et al., 2012. Complete genome sequence of *Liberibacter crescens* BT-1. Stand Genomic Sci 7:271-283.
13. Lin et al., 2011. The complete genome sequence of '*Candidatus Liberibacter solanacearum*', the bacterium associated with potato zebra chip disease. PLoS One 6:e19135.
14. Lugtenberga and Kamilova, 2009. Plant-growth-promoting Rhizobacteria. Annu. Rev. Microbiol. 63:541-556.
15. Porat et al., 2003. Induction of resistance to *Penicillium digitatum* in grapefruit by β-aminobutyric acid. Eur. J. Plant Pathol. 109(9):901-907.
16. Spoel and Dong, 2012. How do plants achieve immunity? Defence without specialized immune cells. Nature Reviews Immunology 12:89-100.
17. Tiwari et al., 2011. Insecticide resistance in field populations of Asian citrus psyllid in Florida. Pest Manag. Sci. 67:1258-1268.
18. Tiwari et al., 2013. Induced resistance against the Asian citrus psyllid, *Diaphorina citri*, by β-aminobutyric acid in citrus. Bulletin of Entomological Research 103:592-600.
18. Trivedi et al., 2009. Quantification of viable *Candidatus Liberibacter asiaticus* in hosts using quantitative PCR with the aid of ethidium monoazide (EMA). European Journal of Plant Pathology 124:553-563.
20. Trivedi et al., 2011. Isolation and characterization of beneficial bacterial community associated with citrus roots in Florida. Microbial Ecology 62: 324-36.15. Vallad and Goodman, 2004. Systemic acquired resistance and induced systemic resistance in conventional agriculture. Crop Science 44:1920-1934.
21. Vallad and Goodman, 2004. Systemic acquired resistance and induced systemic resistance in conventional agriculture. Crop Science 44:1920-1934.
22. van Loon et al., 2006. Significance of inducible defense-related proteins in infected plants. Annu. Rev. Phytopathol. 44:135-162.
23. Walters et al., 2013. Controlling crop diseases using induced resistance: challenges for the future. J. Exp. Bot. 64:1263-1280.18. Walters et al., 2005. Induced resistance for plant disease control: Maximizing the efficacy of resistance elicitors. Phytopathology 95:1368-1373.
24. Wang and Trivedi, 2013. Citrus Huanglongbing: an old problem with an unprecedented challenge. Phytopathology 103:652-665.
25. Zamioudis and Pieterse, 2012. Modulation of host immunity by beneficial microbes. Mol. Plant-Microbe Interact. 25:139-150.

7. Sequences

ATP-dependent DNA helicase UvrD/PcrA, *Paenibacillus* sp. ATY16.

(SEQ ID NO: 4)
atgtttaatccgataaatattgatcaagccgtacagaagctgaaccctcc
tcagagggatgccgttcaagcgacggatggaccattgcttatcatggcgg
gagcgggctccggcaagacccgcgtccttactcaccgtattgcctattta
atcgagaagaagcgggttgcccttggagcattctggccattacctttac
gaataaagcggccagggagatgcaggcgagggtggcggcgcttattggcc -continued

```
cttccggtcaggatatttgggtctctaccttccactccatgtgcgtacgg
attctccgcagggatatcgaccgcatcggctttacctccaatttctcgat
cctggattccgccgaccagctgtcggtcattcgcaattgcatgaaagagc
ttaatatcgacgtgaaaaagtttgaaccgaaagccgttcaggctgaaatc
agcggcgcgaagaatgagctgattacgccggagcgttatgagcagaagat
aggcgactattttaccgatattgtggcgaaagtatttaagatgtaccaga
agcggctgaagagcaacaactcgctggactttgacgatctgatcatgacg
acgattcagctgttcaaggaaatgccggaagtgcttgagttctaccagaa
caaattccgttatatccacgtggacgagtatcaggatacgaaccgcgcgc
aatacatgctttgccgcatgctggctgacaagcatcacaatatttgcgtt
gtcggcgacagcgaccagtcgatctaccgctggcgcggagcggacattac
gaacatcctgaactttgaggatgactatccggaagcccgtaccattatgc
tcgagcagaattaccgttctacggccaacattctggaagcggccaatgcc
gtcatcaagctgaacacgggccgcaagccgaagaagctgtggaccgacca
aggagaaggcgacatgatcaccttgtaccaagccgactccgagcatgatg
aaggatatttcgtaaccggcacgatcagcaaaaacgtgaaaagcggccgc
aggtacgatgaccatgcgattctgtaccgcaccaacgcccagtcccgcgt
aatcgaggaaatactgatcaagtcggacattccgtatcagattgtcggcg
gcatcaagttctacgaccgcaaagagattaaggatttgctcgcttacctc
agactgatctccaatccggacgacgatatcagcttgcagcggatcatcaa
tgttccgaagcggggaatcggcgatacgacggtagcgaagctggcggaag
aagcagttcgtcaaggcacgtctatctttaacgtgcttggcaatctgcaa
gggatagatctgaacgcccgggcacagggcctgctgcatgaattccggaa
tatgatcgataatctaacgcagatggtcgattatctgtccgtaaccgagc
tgacggagaaagtgttggaaatgtcgcaataccgcatggagttgcagcgc
gagaagacgcttgagtcgactgcccgcctcgagaacatcgacgagttcct
gtccgttacgatggacttcgagaagcgcaacgaagacaagacgttagtcg
ctttcctgacggatcttgcccttatcgcggatattgattccatggacaag
gacgatgacggaaaaccggcggacaacaattccgttgttctcatgacgat
gcatagcgcgaaaggcctggagttcccggttgtctttattatcgggatgg
aggaaagcatcttcccgcacagccgtgcgttaaacgataacgaagagctc
gaagaagagcgccgccttgcttacgtagggattacccgcgcggagaagca
gctttacctgacttgcgcgcgcagccggactctcttcggccgcatcagcg
ccaacctgccttcgcgtttcctgcaggaagtgccggacaacgtgaagacg
ctggcttcgccgggcggtacgatcggccgctccggcagctttgccggcgg
cgcaagccgcgcaagcttcggcagcagcggtagcggaccagctttggcg
cagggcgcgcgccatcctttggcgcttccggcgccggagcccgaaccccg
ggaccatcggggcgggagtgcgcgtgagcacgccgcttgacgcggccgc
gaaagcggcgtctaccgccggatcggccgcggggaatgccgcggaccgga
acttcgtagccggcgacaaggttgcgcacggcaaatggggcgaaggcgtc
atcgtttccgtcaaagggacgggcaacgatatggagctgcaaatcgcttt
```

```
ccctgcgccggttggcgtcaaacggcttttggccggatttgcaccaataa
caaaagtctaa
```

Protein export cytoplasm protein SecA ATPase RNA helicase (preprotein translocase subunit SecA), *Paenibacillus* sp. ATY16.

(SEQ ID NO: 5)
```
atgctcggactagtgaaaaaaatattcggtgatgcgaacgagcgcgaggt
caagcgtctcacgcgtacggtagaagaaattaacggacttgagtccaaga
tatcgccgctgtcagacgatgagctgcgtaataaaaacggaagagttcaag
ggacgtcttgaaaaaggcgaggatattgactcgattctgccggaagcttt
cgcggttgtgcgcgaagcatcgaagcgtacgcttggcatgcgccatttcg
acgtacagctgatgggtggtatggtgctgcacgaaggcaagatcgcagag
atgagaaccggtgaagtaaaacgctcgttgcgacgcttcctacttatct
gaatgcattgcaaggcaaaggcgtacacgttattacggtcaatgattacc
ttgcatctcgcgacagccagatcatggctgaactttataatttcctcgga
ctgactgtcggctgcaacctgcacggcttgacgcatgaagagaagcaaga
agcttatgctgcgatattacttacggaaccaataatgagttcggctttg
actatttgcgcgataacatggtgctgtacaaagagcaaatggttcaacgc
ccgctttattatgcaatcatagacgaagtggactccatcctggtcgacga
ggcgcgtacgccgctgatcatctccggacaagcacaaaaatcgacggagc
tgtattatgccgctgaccgtttcgtcagccgtttgaaagaggaagaggat
tacacggttgatattaagcttcgcaacgtaacgctgacggaagccggcgt
tgagaaagcggagaaagcattcggcatcgagaacttattcgatcatgcga
acgtaacgctgaaccatcacgtgcaacaagcgcttaaagcgcatgtcatc
atgaagcgcgacgtggattacgtggttaacgaagacgaagtcgtcatcgt
cgacgaattcacggccgtctgatggcgggccgccgttacagcgacggtc
tgcaccaagcgatcgaagcgaaggagcagctgaaggttcagaacgagagc
atgacgcttgcgacgattacgttccagaactacttccgtatgtaccggaa
gctgtcgggcatgaccggtacggcgaagacggaggaagaagagttcaaac
ggatctacggtctcgaggttattcaaattccgacaaaccgcgctctgatc
cgtaaagatatgcaggacgtggtctacaaatccgagaatggcaagtttaa
agccgttgttgaggaaatcgtagaacgtcacaagaagaaccagccggtac
tcgtgggtacaatctccatcgagaactcggagcgtctgtccgacatgctg
aaaaagcgcggcgtgcagcataaagtactgaacgcgaagttccatgcgga
ggaagcggaaatcatctcccgcgcgggtcaagcgggcgcggttacgatcg
cgacaaacatggcgggacgcggtacggacattttgctcggcgaaggcgtt
catgacgtaggcggtctgcacattatcggtacggagcgccatgagagccg
tcgtatcgataaccagctgcgcggtcgtgccggccgtcaaggcgacccgg
gctcctcgcagttctatctctcccttgaggatgaactgatgcgccgcttt
ggcgcggagaacattatgggcatgatggaccgtctgggtctggaagaaga
ccagccgatcgagagccgcctcattacgcgtgccgttgagtccgctcaga
```

-continued agcgcgtagagggcagcaacttcgatacccgtaaagtcgtcctgcaatat gacgatgtcatgaaccagcagcgggaagtgatttacaagcagcgccgtga cgtattgtactcggagaacatccgcgagatcgttatggaaatgatcatac cggttatcgagcatgtggttgaagccatacggaaggcgatattccggaa gagtgggatctgcaggaaatcgcggattacgcgaactcgaaccttctccc tgaagatacgttctcgaaggacgatctgtggggcaaagagaaggaagata ttatcgagcttatcaaggataaggttgttgcttattacgatgagcgcgag gctgagcttggcgccgaaacgatgcgcgaattcgagaaggttgtcgtact gcgcgcggtagacagcaaatggatggatcacatcgatgcgatggatcagc tccgccaaggtatccacctccgtgcatacggcggtacggatccgcttcgc gagtaccaattcgaaggcttcgagatgtttaaggaaatgatctacagcat ccaggaagaagtcgcgaagtacatcatgaaggcacgagtggagagcaacc tggagcgtcaagaggttgcgcaaggccagacgacgaccaacagcccggcg gaagcggaaaaacgccctgcgaagcgtgaagagcgtacgggacgcaacga cctttgcccatgcggcagcggcaagaaatacaaaatgtgccatggcatgg gcaagtaa Carbamoyl-phosphate synthase small chain cara, *Paenibacillus* sp. ATY16.

(SEQ ID NO: 6)
atgcaagcaagattattgttggaagacggaacgttgtttaccggacaatc tttcggcgcggagacgcaaacgttcggagaggttgttttaatacaggga ttacggggtaccaggaagtattgtccgatccatcctactgcggacaaatc gtatcgatgacttatccgctgattggcaactacggcatttcgcgcgatga cttcgagtcgatccgcccaagcattcacgggtttgttgtacgccgttatg agccggtgccaagcaactggcgcgcgcaatattcgctcggcgacctgctg aaggaatacaacattccgggcatcacaggcatcgatacgcgcatgctgac tcgtattctgcgtcagcacggtacaatgaaggcgttctgacaaccggca ccgaacgcgtggaagagcttcaggaacgtcttggcggcattcagctgatg acggatcaagttgcgcgcacatcgaccaaatcggtcttctcgagcccggg ctttggccctcgcatcgtgcttgtcgacttcggagctaagagcggtatcc ttcgcgagctgacgcagcgcggctgcgacgttgtggttgttcctcataac acaacggcggacgagattcgcaaattggctccggacggcattcagctgtc caacggccctggggatccgaaagacgttccttatgcggttcaaatgatca aagagctgctcggcgagattcctatcttcggcatctgccttggtcaccag ctgttcgctctggcttgcggcgcggatacgacaagacttaagttcggtca ccgcggcggcaaccatccggttaaagaactggctaccggccgatgctacg ttacttcgcagaaccatggctacacggttctcgaagattcgatcaacagc acggaactatccgttacgcacatcaataacatgacaagaccattgaagg tctgaaacataacaaatacccggcattctcggtgcaataccatccggaag ctgcgccaggcccgtttgattccagctatctgttcgatgaattcctggac atgatccgcgaccacaaacaaaacaacccgcaaaaacctcgtcaagctgt gctggcggcaacgttgaaaggagaacttcaatatgcccaaaaataa RecA protein, *Paenibacillus* sp. ATY16.

(SEQ ID NO: 7)
atgcaagttgaaaccgtaccaagcggttcaattgctttagatattgctct tggaatcggcggtatgccaagaggccgtattattgaatgctacggaccgg aatcctccggtaaaacaaccgttgcgcttcacgctattgcggaagtacaa cggatcggcggacaagctgcatttatcgatgcggagcatgcgcttgatcc attgtacgcgagcaagctgggcgtaaatatcgacgaactgctgttgtcgc agccggatacgggtgaacaggcgcttgagatcgcagaagcgcttgtacga agcggcgcggtcgacattatcgttatcgactccgtagcagcacttgtacc gaaagcagagattgaaggcgatatgggggattcccatgtcggtctgcagg cacgtctgatgtcgcaggctctgcgtaaattgggtggcgcgatcagcaag tcgaagacaatcgccatctttattaaccagttgcgcgagaaagtcggcgt tatgttcggtaacccggaaactacgcctggcggccgcgcactgaagttct attccagcgtgcgtctggaagtacgccggattgagcaatcaagcaaggc aacgatatggttggtaaccgtacgcggattaaagtcgtgaagaacaaagt agctcctccgttcaagcaagcggagattgatatcatgtacggcgaaggca tttcgagagaaggcagccttgtagatattggcgtagagatggatatcgtt cagaagagcggagcttggttctcctacaatggcgaccgtcttggccaagg tcgcgagaatgccaagcagttcctgaaggatcatccggaagtggctgctg taatcgagagacaaatccgcgagcaaagcaatttgtccgcttccgcgcag cctgcgaacttctcgcaggatgatgacgatgactttgatgagtcggaact tgacgattaa Chaperone protein DnaK, *Paenibacillus* sp. ATY16.

(SEQ ID NO: 8)
atgagtaaagttatcggtattgaccttggtactacaaactcttgtgttgc tgtaatggaaggcggcgaagctgtcgttatcccgaatccggaaggcaacc gcacaacgccatccgttgtaggcttcaaaaaagacggagagcgcattgtc ggcgaaacggcgaaacgccaagccatcacgaatcccgaccgtacggtaat gtcgatcaaacgtcatatgggtactaaccataaagaagttattgacggca agaatatacggctcaagagatttcggctattattttgcaaaaactgaaa tccgatgcggaagcctatctgggccaatccgtaacgcaagcggttattac cgttccggcttacttcaacgacagccagcgccaagcaacaaaagacgcag gcaaaatcgcgggacttgaagttcttcgtatcgtcaacgagccaacggcg gctgcgctggcttacggtcttgagaaaacagaagaccaaacgatcctcgt ctatgaccttggcggcggtacattcgacgtatcgatcctggaacttggcg acggcttcttcgaagttaaagcaacaagcggcgacaacaagctgggcggc gacgactttgaccaagtcatcatcgactacctcgtagccgaattcaagaa agagcaaggcgttgacctgtccaaagacaaagcggctgttcaacgtttga -continued

```
aagacgctgccgaaaaagcgaaaaaagatctgtccggcgtaatgtcgacg
acgatttcgcttccgtttatcacaatggccgatggcgttccacagcactt
ggagcttaacctgactcgcgcgaaattcgaagaattgtccgctcatctgg
ttgaacgttccctcgctcctacgcgccaagctttgagcgattccggtctc
tccgtaaatgacatcgataaagttgttcttgtcggcggttcgactcgtat
ccctgccgttcaagaagcggttaagaagctgatcggcaaagagccgcaca
aaggcgttaacccggatgaagtcgttgccctcggcgcagcggttcaagcc
ggcgtattgactggcgacgtaaaagacgtggtattgcttgacgtcactcc
gctgtccctcggcatcgagactgcaggcggcgtcttcacgaagatgattg
accgcaatacgacgatccctacaagcaaatcccaagtgttctccacttat
gcggataaccaaccgggcgttgaaattcacgttctgcaaggcgagcgtca
aatggctgccggcaacaaaacgcttggccgcttcacgctgaacgatattc
ctctcgcaccgcgcggcgttccgcaaatcgaagttaccttcgacatcgat
gcgaacggtatcgttaacgtatccgctcttgataaaggcacaggcaagag
ccaaaaaattacgatcacttcctcgggcggtctgagcgaggctgaaatcg
agcaaatgatgaaggatgccgagctgaacgcggaagaagatcgcaaacgc
cgcgagcttgttgaagcgaagaacagcgcagaccaactcgtttactcggt
tgacaaaacattgaaagatctgggcgataaagtagatgcttccgagatcg
agaaagctaacgccgcgaaagagaaagtaacaagcgcggtagcgacagac
gatctggatcaaattacgaaagctaccgaagagctgactgaaatcgtgca
acagctgtccgtgaagctgtatgagcaagcgcaagctgctcaaggcggcc
cggaagcaggcgctgaagcagccgatgcaggcgctcgcggcaaagacaat
gttgtggacgctgactatgaagtagttgacgaaaacaagaaataa
```

Heat shock protein 60 family chaperone GroEL, *Paenibacillus* sp. ATY16.

(SEQ ID NO: 9)
```
atggcaaaagaaattaaatttagcgaagacgctcgtcgcgcaatgctgcg
cggtgttgatcaacttgcaaacgcggttaaagtaacgcttggtcctaaag
gccgcaacgtggtactggagaagaaatttggcagcccgctcatcacgaac
gacggcgtttccatcgcgaaagaaatcgagctggaagacgcattcgagaa
catgggcgctcaactggttaaagaagtagcgactaaaacaaacgacgttg
ccggcgacggtacaacgacggctaccgttctggctcaagcgatgattcgc
gaaggcctgaaaaacgttacggcaggcgctaacccaatggttatccgcaa
aggcatcgaaaagcggttaaagctgcggttgaagagctgaaagctatcg
ctaaaccaatcgaaggcaaacaatcgatcgcgcaagtagcttcgatctcc
gctgctgacgatgaagttggccaactgattgcggaagctatggaaaaagt
gggcaacgacggcgttatcaccgttgaagagtcgaaaggcttcgtaacgg
aacttgaagtggttgaaggcatgcaattcgaccgcggttacgtttcccg
tacatgatcacggatacggataaaatggaagctgtcctcgacaatccata
cattctgatcacggacaaaagatctcgaacatccaagagatcctgcctg
ttctggagaaagtcgttcaatccggcaaacagctcctgatcatcgcggaa
```

-continued
```
gacatcgaaggcgaagcgcaagctacgctcgtactgaacaaactgcgcgg
cacattcacttgcgtaggcgttaaagctccgggcttcggcgaccgccgca
aagcgatgctggctgatatcgcggctctgactggcgcgcaagtcgtaacg
gaagaactcggccttgagctgaaatccgctactgtggaccaactcggttc
cgctcgccaagttcgcattacgaaagaaaacacgatcatcgttgacggca
gcggcaaccctgacgacatccaagctcgcgttaaccaaatccgcgtgcag
ctggaagaaacaacttccgagttcgaccgtgagaagctgcaagagcgtct
ggctaaactggctggcggcgtagcggtaatcaaagtcggcgcggctaccg
aaaccgaactgaaagagcgcaagctccgcattgaagatgccctgaactcg
actcgcgcagcggttgaagaaggcatcgtatccggcggcggtacagctct
gatcaatgtatacaaagcagttgcggctattcaaattggcggcgacgagc
aaacaggcgttaacatcgtattgcgctccctcgaagagccgcttcgcaca
atcgctgcgaacgctggccaagaaggttccgtcatcgttgagcgtctgaa
aaacgaaaaagttggcattggttacaatgccgcaaccggcgaatgggtga
acatgttcgaagcgggtatcgttgaccctgcgaaagtaactcgttccgct
ctgcaaaacgcagcttccgtagcggctatgttcctgactaccgaagcggt
tgttgccgacaagcctgagaaagacaaaccggctatgcctgatatgggcg
gcatgggcggtatgggcggcatgatgtaa
```

ATP synthase beta chain atpD, *Paenibacillus* sp. ATY16.

(SEQ ID NO: 10)
```
atgaaaaaaggacgcgttgtatccgtcatgggtccagtcgttgacttgga
gttcgaacgcggtaaccctgccggaaattttgaacgccgtcaaaatcgttc
aacaggccccagcaggcggcatcgatattaatctgacgcttgaagtagca
gttcacctgggtgataacctggttcgtgctgttgcgatgagcacaactga
cggtctggtccgcggcatggaagctgtagacacaggcgcgccaatcacaa
ttccagttggtgcgccaacactcggccgcgtatttaacgtactgggcgag
ccaatcgaccaagctggcgacgcaacttcggaaattaaccttccgattca
ccgtcaagctcctgcattcgacgaattgtccacgcaatcggaaattctcg
aaacaggcatcaaagttatcgacttgcttgctccgtacgcaaaaggcggt
aaaatcggtctgttcggcggcgcgggcgtaggcaaaacggtaacaatcca
ggaacttatcaacaacatcgcgcaagagcatggcggtatctccgtattcg
ccggcgtaggcgagcgtactcgtgaaggtaatgaccttaccacgagatg
aaagattccggcgtacttccaaaaacagcgatggtattcggacaaatgaa
cgaaccgccgggcgcacgtcaacgcgtagccctgacgggtctgacaatgg
ctgaatacttccgtgacgctgaaggcaaagacgtacttctgttcgtcgac
aacatcttccgcttcacgcaagcaggttccgaggtttcggccttctcgg
ccgtatgccttccgcggtaggttaccagccaacgctggcaactgaaatgg
gtcaattgcaagagcgtatcacatcgacgaaaaaggttcggttacttcg
atccaagcgatctacgtacctgccgatgactatactgacccggctcctgc
aacgacgtttgctcacttggacgctacaactaaccttgagcgtaaaatct
``` gyrB (DNA gyrase subunit B), *Paenibacillus* sp. ATY16.

(SEQ ID NO: 11)
```
atggcagagcaagtagatcttttcgcaaaaacagcggccccggaacggaa
ttacgaggccgatgacatacaagtgctcgaaggcttgaccgctgtcagaa
agcggccgggcatgtacattggcagcacgagcagctccggccttcatcat
ctggtctgggaaatcgtcgataacgccgtggacgagcatttagcgaaatt
ttgtacggcgatcgacgtcacgctgcacaagaatggcgcggttaccgtgc
aggataacgggcgcggcattccgacagggatgcataagacaggaattccg
acgccgcaggtcgtattcaccatcctgcacgcgggcggcaagttcggcgg
cggaggatacaagaaatccggcggtctgcacggcgtaggcgcttcggtaa
caaacgcattgtccgagtggcttgaagtgaaattttccgtgacgggaaa
atacataagatgcgcttcgaatactgggtagacgataaaggcaaggagca
tgtcggcgagccggtaacagggcttgagattacggggaacacgaaccgaa
cgggtagcaaggtaacgttcaaaccggacgcgcgcgtcttccagggcggc
acctcgctgaactacgataccctggccgagcgcctgcaggagattgcatt
cctgaactcgggccttaaggttacgatcaaggacgaccgcagcggcaaag
aggatattttccactacgaaggcggcgcccgccagttcgtgcaatatttg
aacgacgacaagaccgtcctgcacgatgtcgttcatttcacgggagagaa
ggacgagattgaagtggaagtagcacttcagtacaacgacggatataccg
agacgatcgcatccttcgtaaactcgatcccgacacgcggcggcggtacg
catgagaccggtttcaaaaccgcttatacgcgggttatgaacgaatatgc
ccgcaaggctggtctcctgaaggaaaaggaaaagaatctagaaggcaatg
atctgcgcgaaggcatgatgtcggtcattaacatcaagatgtccgaggtc
gaattcgtcggccagacgaaggaccagctgggcagcgcgtcggctcgcag
cgcggtagacgccgtagtctccgacaagatgcaggtgttcctggaagaga
atccacaggtcgcgcaaatgctgctgaagaaggcggtacaagcctccaag
gcaagagaagcggcacgcaaagcgcgcgaagagatccgcagcggcaagaa
gaagagcgaaagctccaatctgaacgcaagctgacgccggctcagtcga
aagatttctcgcgcaacgagctgtttatcgtcgaaggcgattcggcgggc
ggctcggcgaagcagggccgggattcgaagcatcaggctattctgccgct
gaagggcaagccgatgaacccggaaaaagcgaaattgctggatattctga
```

```
agaacgaggaatacaaagccataataagcgcgattggagcgggcgttggc
ccggagtttgacgcggatgaatgcaattacagcaaaatcattattatgac
cgacgcggatacggacggcgcgcatatccaagtgctgctgctgacgttct
tctatcggtacatgaaaccgctgatcgacaccgggcgcgtctatatcgct
cagccgcctttatacaagatcactcgcaaatcgggcaagctggagacggt
ccggtatgcatggacggatgaccagctgcaaaattatttgaaggaattcg
gcaagaactttgagcttcagcgctataaagggcttggcgagatgaatccc
gatcagctgtgggagaccacgatggatccggagacgcggacgctgctgca
ggtgcagatcatgcggcaaaagcggaacgccgcgtgtccgccctgatggg
cgacaaggttgacccgcgcaagcgttggattattgagaacgtagacttca
cagtatacgtagaatag
```

Translation initiation factor 2 (infB), *Paenibacillus* sp. ATY16.

(SEQ ID NO: 12)
```
ttgagcaaacaacaggacaacagcaaggacaataaagataaaacacgcgt
atacgaatacgcgaaatcgctaaacatgagcagtaaagaaattataacga
ttcttaaacggcttaatctgcccgttaataatcatatgagtgtcatggaa
aacgaaatggttcaaaaagtggaaggcttcttccgcgatatcaagcaaaa
tgcggctgcgaagcgtgcccaggaatcgggcagtgctaccgtatcggcgg
cacctcagccacaggcacagaccgcaagcaagcagcaaaatcaaacggta
caaaaaaatctatctcaggacagacaggggcctatgaattctattaaaac
gacatccgaaaccaaccaatcgcaacaagaacaacgtccgcaaagtcagc
aaggaaacgaaagtcaaacgaacgctagccaggctaacgccggcacaagc
gacaatagcgcaagcagcaataacagaccgcagaacagcggcaaccgtca
aggttcttatcaaggccaaggcggtcaaggcggcaatcgtccgcaaggcg
gcggcggatacaaccgtccgcaaggtcaaggcggtcaaggtggcaatcgt
ccgcaaggcggcggcggatacaaccgtccgcaaggtcaaggcggtcaagg
cggcaatcgtccgcaaggcggcggcggatacaaccgtccgcaaggtcaag
gcggccaaggcggcaatcgtccgcaaggtcaaggcggcggcggatttaac
cgtccgcaaggtcaaggcggcgcaccgggcggcaaccgtccgcaaggcgg
cggcgcaccaggcggtaaccgtccgcaaggtcaaggcggcggacaaaacc
gtacgttcgattcgtcccgtccggcaccaacttcgcgtggtactgcggca
ggcgaaaccaacaaccgtaaaggcaacaatgcggtaaacaaaaacagaac
gggtggcaacaacggaagccaaaagcgtttcgacgacgggaagccgaact
ttagaacgaatcctaacggtcgcggcaaaggcggcagaaacaaccgtaac
cattcgcagcagcctccacgcgagaaaatcgacaatacgcctaagaaaat
cattgtgcgcggtacgatgacagtaggcgatttggctaagctgcttcata
aggatgcttccgaagttatcaagaagcttatttctcttggcgtaatggct
actatcaaccaagaacttgacatggataccattcttttgatcgctcaaga
atttggcgtagaggttgaagtgaaaattccggttgaagaagatccttcg
```

-continued

```
aaaccgtggaagaagtggatgacgaagcggatttgacgactcgtccaccg
gttgtaacgattatgggtcacgttgaccatggtaaaacaacccttctcga
cgctatccgtcatacaaacgtaacgggcggcgaagcaggcggcatcactc
agcatatcggtgcttaccaagttgagatcaaccataagaaaattacgttc
ctcgatacaccgggtcacgaagcgtttacgctcatgcgcgcacgcggtgc
tcaagtaacggatattacgatcatcgttgttgcagccgatgacggctta
tgcctcagacggttgaagcagtcaaccatgcgaaagcggctggcgtgcct
attatcgtagcggttaacaaaatcgataaaccggacgcggatcctgacaa
aatcaaacaggcgcttacggaatacgaactcgttccggaagaatggggcg
gcgataccatcttcgttaacgtatcggctaagcaacgccttggtctggaa
gagctgctcgagatgattctgctcgtggctgaagttaatgattacaaagc
gaattccgacaaacgcgcacgcggtacggttattgaagccgagctggata
aaggtaaaggtccggtagcacgcgttctcgtacaacacggctcgctgaag
attggcgatgctttcgttgccggtaactgcttcggtcgtgtccgcgcaat
ggtgaacgataaaggccgccgtatcaaagaagccggtccttctactccgg
ttgagattaccggtttgacagaagtaccgcttgcaggcgatccgtttatg
gtatttgaagacgagcgcaaagcaagagcgattgctgaccgtcgttcgat
caaacaacgtcagtcggagcttggcgcgaattcccgcgttacgcttgacg
atctgttcaagcatattcaagaaggcgagatcaaagatcttaacatcatt
atcaagtctgacgttcaaggctcgacagaggccctcaaaggctcccttgg
gaaaattgaaatcgaaggcgttcgcatcaagatcattcacagcggcgtag
gcgcgatcacggaatccgatatcaacttggctgcggcatccaacgctatc
gtaatcggatttaacgttcgtcctgagccgcaagctgatcttgccgcaca
gcaagagaaagtggatgttcgtctgcaccgcgttatttacaacgtaatcg
aagagattgagcaagccatgaaaggcatgctggatccaatcttcaaagaa
gttgttcaaggtcaagcggaagtccgcaacatctttaagctcagcaaggt
tggcgctattgccggatgtatggttatcagcggcaaaattacgcgtaact
ccgaagttcgcgtcatccgcggcggtatcgttgtattcgaaggcaaaatg
gataccgttaaacgcttcaaggatgatgttaaagaagttgctcaaggcta
cgagtgcggtattacgatcgagcggtttagcgacttcaaagaaggggata
ttattgaagccttcgtaatggagtccgtagagaggtga
```

ATP-dependent DNA helicase UvrD/PcrA, *B. megaterium* PT6.

(SEQ ID NO: 13)
```
atgttcgatataggcggtgaaaacgtgaatttttaagtgaaaaattatt
aacaggattaaaccctcagcaacaagaggcagttaaaacgacagacggac
cactattacttatggccggtgcaggaagtggaaaaacacgtgtattaacg
catcgaattgcgttttaatggcagaaaaagaagttgcaccttggaatat
tttagccattacttttacaaacaaagcagctcgtgaaatgagagagcgtg
tttcaaatatcgttggcggagtggcagaagatatctggatttcaacgttc
cactcgatgtgcgtgcgtattttacgaagagatattgatcgtattggctt
```

-continued

```
taatcgtaactttacgattttagattcaacggatcagctgtccgttatta
aaaatatttaaaagatcaaaacatcgatccgaaaaaattcgatccgcgc
tcgttattaggaagcattagttcagctaaaaatgaactgaaagtagcgga
agaaatttgataaaacagcagcgggaccgtatgaagaagttgtaagcaaag
tctacaaagagtatgaaaagcgtttaaagaaaaaccaagcgcttgattt
gatgatttgattatgacaacgattcagctatttaaacgagttcctgaagt
gttaacttactatcagcgcaagtttcaatatattcatgtggacgagtatc
aagatacaaaccatgcacagtatatgctggttcgcttgctagctgcaaga
tttgaaaatgtatgcgtagtaggggattcagatcagtctatttaccgctg
gcgcggggctgatattacaaatatcttgtcatttgaaaagattacccaa
aagcgaaaaccattttgcttgaacaaaattatcgttcaactaaaacgatt
ttggctgcggcaaacggcgtcattgcaaacaatatgaatcgtaaagtgaa
aaacttatggacggaaaacgatgaaggccagaagatttaccattaccaag
caatgagtgagcatgatgaggcacagtttgtagcacgtaaaattaaagaa
gcagtagacagcggaaagcgtaaatacagtgattttgccattttgtatcg
tacaaatgcacagtctcgtgtgatggaggaagtgctgttaaaatccaata
ttaattatacaattgtcggcggcattaagttctacgaccgcaaagagatt
aaagatttacttgcgtacttgcgcttaattgccaaccaagatgatgacat
tagcttagctcgtattgtgaacgttccaaagcgcggagttggagctactt
cagtcgataaagtggccaattacggaaacgttcatgacatttcgattttc
aaagcactggatgaagtagaattaatgggggttaacaggcaaagcaacaaa
agcccttcgtgatttccaatcgatgatttcgaacttagctcaaatgcaag
actatatgtctgttacagagcttgtggaacaagtattagaaagaacggga
taccgtgaagcgcttaaagtggaaaaaacaattgaagcacaaagccgctt
agagaatattgatgagtttttatctgtcacaaaaacgtttgaagaagcaa
gtgaagataaaagcttagtagcatttttaaccgatttagcacttgttgct
gatatcgataagcttgacgacgaggaagaagaagagaacgaacaagtgat
tctgatgacgcttcactcggcaaaaggtctagagttcccggttgttttc
taatgggtatggaagaaggcgtattccctcatagccgatcattattcgaa
gataatgaaatggaagaggaacgacgcttagcctatgtaggaattacgcg
tgctgaacaagaattatatttattaaatgctcaaatgcgcacactatttg
gtaaaacaaacgttaatccaaaatcgcgcttcattggagaaatcccaagc
gagcttgtggaatctttaaatgaagcaatgcgcaaacctgctgctggtcg
ttcaggggcttcagcttcgccgtttgcagcgcgccgacaagcggccgtgg
caaaaacgaagcttgtgtcaacaggcagtgaatcaattggatggagcgtt
ggagacaaggctgagcataaaaaatggggaattggtacagttgtaagtgt
aaaaggagaaggagattcaaaagaattagacattgcttttcctagtccta
caggtgtaaaaagactgcttgctaaatttgccccggttacgaaagtgtaa
```

Protein export cytoplasm protein SecA ATPase RNA helicase, *B. megaterium* PT6.

(SEQ ID NO: 14)
atgcttggattatttaaaaaagtgtttgacggcaatcagcgccaaatcgg
ccgtttagaaaaaatggcggaccaaattgatgcgttaggtcctgaaatag
cgtctttaacagacgatcagcttcgtgaaaaaacggctgaatttcaacca
cgctaccaaaatggcgaatcgctcgataacctattagatgaagcttttgc
ggttgtacgtgaagcagcgaaacgtgtgttaggcatgtatccgtacaaag
ttcagctaatggggggtatttctctgcatgaagggaatatctcggaaatg
aaaacgggtgaaggtaaaacgttgacagctactatgcctgtatacttaaa
cgccattacaggaaaaggtgtacatgtagtaacagtcaatgaatacttag
cgagccgtgatgctagtgaaatgggtcgtttatatgaattcctaggtttg
aaagtaggtttaaatttaaaccatttaacgcgtgaagaaaagcaagaagc
atatgcagcggatattacgtatagtacaaataatgaactcggatttgact
atttacgtgataacatggtgctttacaaagaaacaaatggttcaacgtccg
cttcattttgccgtaatcgatgaagttgactctatcttaattgatgaagc
acgtacgccgcttattatatcgggcagcgcgcagaaatcgactgctcttt
atattcaagctaatgcattcgttcgcacgcttgataaagaaaccgatttt
acttttgatatcaaaacaaaagcgttcagctaaccgaagaaggtatgtc
aaaagcagagcgcgcatttggcattgaaaacttatttgatatttcacacg
tagcgctaaaccatcacatcaaccaagcgcttaaagcacatgtaacgatg
caaaatgatgtggattacgtaattgatgaagatcaggtcgtaatcgttga
ccaatttactggtcgtttaatgaaaggaagacgttttagcgacggcttgc
atcaagctatcgaagctaaagagaatgttgagattcaaaatgaaagcatg
acgttagctacaattacattccaaaactacttccgtatgtatgaaaaatt
atcaggtatgacgggtacagctaaaacggaagaagaagaattccgtaata
tctacaacatgcacgttgttgttattccgacaaacaaaccaattttcacgt
gatgataaagcggatttaattataagtcgatggaaggcaagtttaatgc
ggtagtagaagatattgccgagcgccacgcaaaaggacagcctgttcttg
ttggtacagttgcgatcgaaacatctgaagttttatcagctttattaaag
aaaaaaggcattcgccatcacgtgtttaaatgcaaaacagcatgagcgtga
agcggatattattgaaaatgcgggtcacaaaggtgcggtaacaatcgcaa
cgaatatggccggtcgtggtacggatatcaaactaggtgaaggtgtcgtt
gaagctggcggtcttgctgtaattggtacagagcgtcatgaatcacgccg
tattgataatcagcttcgcggacgtgctggacgtcaaggtgatccaggg
tatctcaattctatctatccatggaagatgaattaatgcgccgatttggt
tcagataatatgatggcaatgatggatcgccttggcatggatgactcaca
gccaattcaaagtaaaattgtaacaagagctgttgaatccgctcaaaaac
gcgttgaaggtaataacttcgatgcgcgtaaacaattgcttcaatatgat
gacgtgcttcgtcaacagcgtgaagttattacaaacagcgctttgaagt
acttgattcagacaacctgcgtgcgattgtagaacgtatgattgaatcaa
ctctacagcgtgtggttgaagtaaacacaccgcgtgaagaattagaagaa
gaatggaatttacaagcgattattgattacgtaaatgctaatgttctga ggaaggtgaagtcacagaagaagatcttcgccgtaaagagcctgaagaaa
tggtagaactgctggtagatcatgcaaaagctcgttataatgaaaagaa
gagcagctccctgaagaacaaatgcgtgaatttgaaaaagttgttgttct
tagagcagttgattctaaatggatggatcatatcgatacgatggatcagc
ttcgccaaggtatccaccttcgtgcgtacggccaaacagatcctcttcgc
gaataccaaatggaagtttttgcgatgtttgaaaatatgattgcaaccat
tgaagaagaagtgacgaagtatatcatgaaagcagaaattaacaacaacc
ttgagcgtcaagaggtagcgcaaggtcaggcggctgttcatccaaaagaa
ggagacgcgccggctaagaagaagccaaaagtaaatgcaatagaagttgg
ccgaaatgatccttgtatctgcggaagtggcaaaaagtataaaaactgct
gcggtaaagaatcataa carbamoyl-phosphate synthase small chain (carA), *B. megaterium* PT6.

(SEQ ID NO: 15)
atgaacggatatttacacttagcaaacggcgattcgttcgccggacacat
tgaacatacagcaacgcaccaggcagaaggagaaattgtttcttactg
gaatgactggttatcaagaagttgtgactgatccatcttacaaagatcaa
attatcgtctttacgtacccctttgattgggaactatggtatcaatgaaaa
agattatgaaagcaaaaagcctcacgtagcaggcgttgtcgtatacgaat
gttcagatgaagggttccattacgaagcgatgtacagctttaaacaatat
ttaaagaaatggaacattccgcttattacacatgtggatacgagagcggt
cgtaaaacgaattcgaaaagaaggtacgatgcaatctgccttttcgacat
ctgctgagccgccagcatttactgctgaatgcgatggatatgtagtaaaa
gaagtatcaacaaaagagcctgttacttacggaaacggtgaaaaacacgt
tgtattaatggactttggctataaaaaatcaattttacaagagctgttaa
atcgagagtgcaaagtaacagttgttccttattctacaagctcttcaaaa
gtaaaagagctgcagccgatggcattgtcttatcaaacggacctggaga
tccaacccaagtgagcagtcagctggatgaattaaaagaaattatttcat
cgtatccaactttgggaatttgctttggacatcagttaattgggcttgct
tttggggcacaaaccaaaaagctggcgttcggtcaccgaggagctaatca
gcctgtaattgatttaacgaataacaaagtgtgtatgacttctcaaaacc
atagctatgtcgtggacgaacagacgattacgtctacgccattaaatgtt
cggtttaaaaatgtgaatgacggatcggttgaaggtttaatgcataaaga
ccttcctgttatgtcggttcaatatcatccagaagcacaccctggaccaa
gtgacagcacgtatatcttttgatgaattatgacgaaagtacagcaagta
gggagcggaaaagtatatgcctaa RecA, *B. megaterium* PT6.

(SEQ ID NO: 16)
gtgaacgatcgtcaagcagcccttgatatggctttaaaacaaattgaaaa
gcaatttggtaaaggttcaattatgaaattaggtgaacaaacgaaaaaa
gaatttctacaattccaagtggttcattagcgttagatatagccttaggt -continued

```
gtaggtggatatccacgtggacgtgtagttgaagtatatggtccagaaag
ctcaggtaaaacaacagttgctcttcatgcgattgcagaagttcaacagc
agggcggacaggctgcatttatcgatgcggagcacgcgttagatcctgta
tatgctcaaaaattaggtgtgaatattgatgagctattattatctcagcc
tgatacgggagaacaagctttagaaattgctgaagctttagttcgaagcg
gtgcagtagatattatcgttgttgactcagtagcagcattagtgccaaaa
gcagaaattgaaggagaaatgggagactctcacgtgggtctacaagctcg
tttaatgtctcaagcattgcgtaaactatctggagctatcaacaagtcta
aaacaatcgctatctttattaaccaaattcgtgaaaaagtcggcgttatg
tttggtaaccctgaaacaactcctggtggacgtgcgcttaaattctattc
ttcagtgcgtctagaagtgcgtcgtgcagagcagttaaagcaaggaaacg
atattgtaggtaacaaaacaagaattaaagttgtgaaaaacaaagtagct
ccgccattccgtgctgctgaagtagatattatgtacggagaaggtatttc
aaaagagggcgaaattttggatatcgcttctgaactagatattgttcaaa
aaagtggatcttggtattcatataatgacgagcgtctaggtcaaggtcgt
gaaaatgcaaaacaattcttaaaagaaaatactgatattcgtcaggaaat
tgcgggacaagtgcgtgaacatcatggtttagaccaagatggagagccag
ctcctgaggatgacgatcaaggcgatttaaatatttaa
```

DnaK, *B. megaterium* PT6.

(SEQ ID NO: 17)
```
atgagtaagatcattggtatcgatttaggtacaactaactcttgtgtcgc
tgtattagaaggcggcgaaccaaaagtaattccaaatccagaaggaaacc
gtacaacaccatcagttgtggcattcaaaaacggtgagcgtcaagttggg
gaagtagcgaaacgtcaagctattacaaaccctaacacaattatttcagt
taaacgtcatatgggtacagaccataaggtggaagctgaaggcaagcaat
acacgcctcaagaaatgtcagctatcattcttcaacatttaaaaggttat
gctgaagagtatttaggtgagcctgtaacaaaagctgttatcacagttcc
tgcttactttaatgatgctgagcgtcaagcaacaaaagatgctggtaaaa
ttgctggtttagaagtagagcgtattattaacgagcctactgcagcagca
cttgcatacggattagaaaaaacagatgaagatcaaacagttttagttta
tgaccttggtggcgtacgtttgacgtatctattctagaacttggcgacg
gcgtatttgaagttcgcgcaactgcaggtgacaaccgccttggtggtgac
gactttgaccaagtaatcatcgactatttagtcgctgaattcaaaaaga
aaacggcgttgatttaagcaaagataaaatggcgcttcaacgtttaaaag
atgcggctgaaaaagcgaaaaaagatttatcaggtgtaacatctacacaa
atttcttaccatttatcactgctggagaagctggccctcttcacttaga
ggtatctttatcacgtgctaaatttgatgagttatcagcaggtcttgtag
agcgtacaatggctcctgtgcgtcaagctttaaaagatgcaggcctttct
gcaagcgaacttgataaagtaatcttagttggtggttcaactcgtatccc
agcggtacaagatgcgatcaaaaaagaaactggtcaagatcctcacaaag
```

Heat shock protein 60 family chaperone GroEL, *B. megaterium* PT6.

(SEQ ID NO: 18)
```
gtgtaaaccctgatgaagtagttgcacttggtgcagcaattcaaggtggc
gtattaactggtgatgtaaaagacgttgtattactagacgtaacgcctt
atcactaggtatcgaaacaatgggtggcgtatttacaaagctaattgagc
gtaatacgacgattccaacaagtaaatcacaagtattctcaacggctgca
gatagccaaacggctgtagatattcatgttcttcaaggtgagcgtccaat
gtctgcagacaataaaacgctaggtcgtttccagttaactgatattccac
ctgcaccacgcggagtacctcaaatcgaagtatcattcgatattgacaaa
aacggtatcgtaaacgttcgtgcaaaagatttaggtacaaacaaagagca
agctattacaattaaatcttcaacaggtttatcagatgatgaaatcgacc
gtatggtaaaagaagcggaagaaaacgcagatgctgataagcaacgtaaa
gaagaagtggaactacgcaatgaagcagatcaattagtgtttacaactga
aaaaacattaaaagatcttgaaggaaaagtagaagaagctgaagtaacaa
aagctaacgaagcaaaagatgctttaaaagcagcgattgaaaagaatgac
cttgaagaaatcaaagcgaaaaaagatgaacttcaagaaatcgttcaagc
gttaactgtaaaattgtatgagcaagctcaacaagctcagcaagcaggtg
aacaaggcgctcaaaatgatgatgttgtagatgcagagtttgaagaagta
aacgacgacaaaaaataa
```

ATP synthase beta chain (atpD), *B. megaterium* PT6.

(SEQ ID NO: 19)
```
caggaaacgcagaagatatcctagcacgcgtaaaccaaatcaaagctcag
cttgaagaaacaacttcagagtttgaccgtgaaaaattacaagagcgctt
agcaaaacttgctggtggcgtagctgtaattaaagttggtgcggcaactg
aaactgagttaaaagaacgtaaattacgtattgaagatgcattaaactct
acgcgtgctgcggttgaagaaggtatcgtagctggtggtggtactgcatt
agtaaatatctataataaagtagcaagcatcgaagctgacggtgacactg
ctacaggtatcaacatcgtattacgtgcgattgaagagcctgtacgtcaa
atcgctcacaacgctggtttagaagggtcagtaatcgttgagcgtctaaa
aggcgaagctgttggaactggatttaacgctgcaactggcgagtgggtaa
atatgctagacactggtatcgttgacccaacaaaagtaacgcgttcagct
cttcaaaatgcttcttctgtagcggctatgttcttaacaactgaagcagt
tgttgctgacaagccagaagaaggcggagcacctgcaatgcctgacatgg
gcggcatgggtggaatgggcggcatgatgtaa
```

ATP synthase beta chain (atpD), *B. megaterium* PT6.

(SEQ ID NO: 19)
```
atgacaaaaggacgcgttactcaaatcatgggtccagttgtagacgtaaa
gtttgacaacggacaccttccggcaatttataacgcccttaaaatttcac
ataaaccgagcagtgcaagtgaagttgcaatcgaattaacattagaagtt
gcgattcacttaggtgataacacagttcgtacagtagcaatgtcatccac
tgacggcttagttcgtggattagaagtagaagatacaggtgcagcaatct
cagtaccagttggtgacgttacattaggtcgtgtatttaacgtattaggt
gaaaaaatcgacttagacgctccaatcgatgcaggtgcacgtcgtgatcc
aatccaccgtcaagcaccaaagttcgaaaatctatctacacaagctgaaa
ttcttgaaacaggtattaaagtagtagacttattagctccttacattaaa
ggtggaaaaatcggtctattcggtggtgccggtgtaggtaaaacagtatt
aattcaagagttaatcaataacattgctcaagagcacggcggtattccgg
tattcgctggtgtaggtgagcgtacgcgtgaaggtaatgacttataccat
gaaatgacagattccggtgttattaagaagacggctatggtatttggaca
aatgaatgagccacctggtgcacgtcaacgtgttgcattaacaggattaa
caatggcagaatacttccgtgacgaacaaggtcaagacgtattattcttt
atcgataatatcttccgttttcacacaagcgggttcagaagtatcagcatt
acttggccgtatgccatcagcagtaggttatcagccaacattagcgacgg
aaatgggtcagcttcaagagcgtatcacgtcaacaagcgtaggttctgta
acatcgattcaagcgatttacgtaccagccgatgactatacggatccagc
tccagcgacaacatttgctcacttagatgcaacaacaaacttagagcgta
aattatcagagatgggtatttaccctgcggtagatccattagcatctaca
tctcgcgctttatctcctgaaattgttggagaagagcactatgcaattgc
gcgtcaagttcaacaaacgttacagcgttataaagagttacaagatatca
ttgcaatcctaggtatggatgagttatctgatgaagataaacttgttgta
caacgtgctcgtcgcgttcaattcttcttgtctcaaaacttccacgtagc
```

```
agagcaatttacaggtcaaaaaggttcttatgttcctgtaaaagaaactg
ttaaaggatttaaagagatcttggaaggtaaatacgatcatttacctgaa
gatgcgttccgtttagttggtcgcattgaagaagttattgaaaatgcgaa
acgtatgggagtagaagtttaa
``` gyrB (DNA gyrase subunit B), *B. megaterium* PT6.

(SEQ ID NO: 20)
```
atggaacaaaaagaagtacaagcatatgaagctgatcagatacaagtatt
agaaggattagaagctgttcgtaaacgtccggggatgtatattggatcga
cgagcgcaaagggtttacatcatcttgtatgggaaattgtagataatagt
attgatgaagcgctggccggctattgcgatgaaattaatgttattatcga
aaaggataatagtattacagtcaaagataacggtcgtggaattccggttg
gtattcaagaaaaaatgggcagacctgctgttgaagttatcttaacggtt
cttcatgccggaggtaaatttggcggtggcggctataaagtatccggtgg
attacacggtgtaggtgcctcagttgttaacgcactttctacctctttgg
aagtgcacgtacatcgtgacggtaaagttcattatcaaaaatatgaacga
ggtgtaccggctgctgacttaaaagtagttggagaaacagataaaacagg
tactgttattcaattccgtccagacagtgaaattttttacagaaacgcttg
aatacgattttgatacgttagctaatcgtctgcgtgagttagctttctta
aatcgcggcattaaaattacgattgaagataaacgtgaagaagataaaag
acgtgaatatcactatgaaggcggaattaagtcttacgttgaacacttaa
accgttcgaaagaagtgattcacgaagagccgatctatattgaaggtaat
cgagacaacatttctgtagaaattgctattcaatataacgatagctatac
aagtaatttatattcttttgcaaacaacattcacacatatgaaggtggaa
cgcacgaagcaggatttaaaacagcgttaacgcgtgtaattaacgactat
gcacgtaaaaacagcgtatttaaagacagtgacgccaatctaacgggtga
agatgttcgtgaaggaattacagctatcatctctattaagcacccagatc
cgcagttcgaaggacaaacaaaaacaaagctgggaaatagtgaagcaaga
acaattactgactctgtgtttgcagaacacttagaaacttacttgctaga
gaacccatttgtggcgaaaaaggtaattgaaaaaggtttaatggctgcaa
gagcaagaatggcagctaaaaaagctcgtgagcttacacgccgtaaaagc
gcgcttgaaatttcaaacttaccgggtaaattagcagattgttcatcaaa
agatccttctattagcgaactttatgtagtagagggtgactctgccggag
gttcagctaagcagggaagaagccgtcatttccaagctattttgcctttg
cgtggtaaaattatcaacgtagagaaagcgcgtttagataaaattttatc
taataacgaaattcgtacaatcattaccgctctaggaacgggtattggtg
acgattttgatatttcgaaagcccgctaccataaaattgtgattatgaca
gatgcagacgtagacggtgcgcatattcgtacgcttcttctaacgttctt
ctatcgctatatgagacagattattgagcacggatatgtgtacattgccc
agccgcctctttacaaagttacacagggtaaaaaagtggagtatgcgtac
aacgatcgtcaattagaagaggtattagcttcttttccctgaaggtgcaaa
```

-continued

```
accaaaccttcagcgttacaaaggtttaggagagatgaatcctgaacaat tatgggaaacaacaatggatccagagttccgtacccttcttcaggtgaac ttgcaagatgcaattgaagctgatgagacatttgaaattttaatgggcga caaagtagaaccacgccgtaatttcattgaagaaaatgctcagtacgtaa aaaatcttgatatttaa
```

Translation initiation factor 2 (infB), *B. megaterium* PT6.

(SEQ ID NO: 21)
```
atgggggtgaaagtattgaataaaaatacaaaatcaacagctaacaaagg aaacaataaaggtaacaaaaagccacaggcacaaaagtcacaggcaccaa aaggtagaccagctccagcagctgcaaaagagttaccggaaaaagtaacg tttgtcggaagcttaacggtttctgagttagcaaaagaattaggcaaaga gccttctgaaattattaaaaaactatttatgcttggtgtaatggcaacaa ttaaccaagagttagataaagattctatcgaactaattgccggagaatac ggtgtagaagttgaagaagaagtagtagtagatgacactgcttttgaatc attagaaatcattgatgacgaaaaagaccttcaagtgcgtcctccagttg ttacaatcatgggtcacgttgaccacggtaaaacgacgcttcttgactct atccgtaacacaaaagtaacggctgcagaagcaggcggtatcacgcagca tatcggtgcttatcaagttgtggttgatgaaaagaaaattacattccttg atacaccagggcatgctgcatttacaacgatgcgtgctcgcggtgcgcaa gtaacggatattacaatccttgttgttgcagcagacgatggtgtaatgcc tcaaacaattgaagcgattaaccatgcaaaagcggcagaagtgccaatta ttgttgcggttaacaaaatggataaagaagcagcaaatccagatcgcgtg atgcaagaactaatggagcacggccttgtagctgaagagtggggcggaga aacaatcttctgtaagctttcagccatttcaggtgaagggatcgatcaat tgcttgaaatgattttacttgtaagtgaagtagaagagttaaaagcaaat ccgaaccgtcgtgcagcaggtacagttgtagaagcacagctagataaagg ccgtgggtctgtagcaacgcttcttgttcaaactggtacactacgcgtag gtgatccaatcgtagtcggaaatacgtttggccgtgttcgcgcaatggta aatgatatcggccgcgtgtgaaggaagtaggaccatctactccggttga gattactggcttaaacgaagttccgttagctggagatcgtttcttagtgt ttgaagatgagaaacagctcgtcaaatcggagaagctcgtgctcaaaag cagcttgaacaacagcgcggtgaaaaatctcgcgtaagcttagatgattt atttgaaaaaattaaacaaggcgaaatgaaagacttaaaccttatcgtaa aagcagacgtacaaggttctgtagaagcattggctgctgctcttcaaaag attgatgtagagggtgtaaatgttcgtattatccatacgggtgtaggtgc gattacagaatctgatatcattcttgcaactgcttctaacgcaatcgtta tcggctttaacgtgcgtccggatgctggagcaaaacgtacagctgacgta gaaaacgtagatattcgtcttcaccgcattatttataaagtaattgaaga aattgaatctgcgatgaaaggaatgcttgatcctgagtttgctgaaaaaa tcatcggtcaagtggaagtacgtcaaacattcaaagtatcaaaagttggt
```

ATP-dependent DNA helicase Uvr/PcrA, *B. subtilis* PT26A.

(SEQ ID NO: 22)
```
ttgaattatattagcaatcaattactaagcggtttaaaccccgttcagca ggaagcagtcaaaacaacggacgggccccttttgctgatggcgggagcgg gaagcggaaagacgcgtgtcctgacacacagaattgcttatttaatggca gaaaagcatgtggcgccgtggaacattctggcgatcacatttacaaataa agcggcacgcgaaatgaaagaacgtgtggaaagcatcctcggacccggcg cggacgatatctggatttccacattccacagcatgtgcgtgcggatcttg cgcagagatatcgaccggattgggatcaaccgaaatttctccatccttga tacggctgaccagctttcagtgattaaggggattttgaaggagcgcaatc ttgatccgaagaagtttgacccgagaagcatcctcggcacgatcagcagt gcgaaaaacgaattgaccgaaccggaggaattctctaaggttgccggcgg ctactacgatcaggtggtcagcgatgtatatgctgattatcagaagaagc tattgaaaaaccagtcgctcgatttcgacgatttgattatgacgacgatt aaactgtttgaccgagtgccggaagtacttgaattttatcagcgcaaatt ccaatacatccatgttgatgagtatcaggatacgaacagggcgcaataca tgcttgttaagcagcttgccgagcgtttccagaaccttttgcgttgtgggg gattctgatcagtcaatctacagatggcgcggcgcggatatcaccaacat cctttcatttgaaaaagattatccgaatgcaagcatgattttgctagaac aaaactatcgttcaacgaaacggattttgcgtgcggctaacgaggtcatc aaaaacaactctaaccgcaaaccgaaaaatttgtggacggaaaacgatga aggcataaaaatttcctattatcgcggtgataatgaattcggagaaggac agtttgtggccggtaaaattcatcagcttcacagctcaggcaagcggaag ctgtctgatatcgccatattataccggacaaacgcgcagtcccgtgtgat tgaggaaacgcttctcaaagcgggcttgaactataacattgtcggcggca caaagttctatgacagaaaagaaattaaagacattcttgcgtacctgcgc ctcgtatccaatccggatgacgatatcagtttcacgcgcattgtcaatgt gccgaagcgcggagtcggcgcgacatcacttgaaaaaatcgcttcgtatg cggccataaacggcttgtcattttttccaagcgattcagcaggttgatttt atcggcgtcagtgccaaagcggcaaacgcgcttgacagctttagacagat gattgagaatctgaccaatatgcaggattacttatccattacagagctga cagaagaaattcttgataagacgaatacagagaaatgctgaaggctgag aaatcgatcgaagcccaaagccgtttagaaaatatcgacgagttcctgtc tgttacgaaaaacttttgaacagaaaagtgaagacaagacactcgttgcgt tcctgacagacttggcattgatcgcagatattgatcagctcgatcagcag
```

-continued gaggaagagtcaggcggcaaggatgcgatcaccctgatgacactgcacgc cgcgaaaggactggagttcccggttgttttcttgatggggcttgaagaag gcgtcttcccgcacagccgttctctcatggaggaagcggaaatggaagaa gaacgccgccttgcgtacgttgggattacaagggcggaacaggagcttta tctgaccaatgctaaaatgcgcaccttgtttggccggacaaatatgaacc cggaatctcgcttcattgctgaaataccggatgatttattggaaaaccta aatgagaaaaagaaacgagagcgacgtctgcgagaaaaatgcagccgag acgcggccctgtttcacgcccggtatcctacgccagcaaaacaggcggcg acaccttgaactgggcagtcggagataaggcgggccataaaaaatgggga acaggaactgttgtcagcgtgaaggagaaggagaagggacggagctcga tattgccttcccgagccctgtcggcgtgaaacgcctgttagcagcatttg ctcctattgaaaagcagtaa Protein export cytoplasm SecA ATPase RNA helicase (TC3.A.5.1.1), *B. subtilis* PT26A.

(SEQ ID NO: 23)
atgcttggaattttaaataaaatgtttgatccaacaaaacgtacgctgaa tagatacgaaaaaattgctaacgatattgatgcgattcgcggagactatg aaaatctctctgacgacgcgttgaaacataaaacaattgaatttaaagag cgccttgaaaaggggcgacaacggatgatcttcttgttgaagctttcgc tgttgttcgagaagcttcacgccgcgtaacaggcatgtttccgtttaaag tccagctcatgggggcgtggcgcttcatgacggaaatatcgcggaaatg aaaacaggggaagggaaaacattaacgtctactctgcctgtttatttaaa tgcgttaacaggtaaaggcgtacacatcgtgactgtcaacgaatacttgg caagccgtgacgctgagcaaatggggaaaattttcgagtttctcggtttg actgtcggtttgaatttaaactcaatgtcaaaagacgaaaaaagggaagc ttatgccgctgatattacttactccacaaacaacgagcttggcttcgact atttgcgtgacaatatggttctttataaagagcagatggttcagcgcccg cttcattttgcggtaatagatgaagttgactctattttaattgatgaagc gagaacaccgcttatcatttctggacaagctgcaaaatccactaagctgt acgtacaggcaaatgctttgtccgcacgttaaaagcggagaaggattac acgtacgatatcaaaacaaaagctgtacagcttactgaagaaggaatgac gaaggcggaaaaagcgttcggcatcgataacctctttgatgtgaagcatg tcgcgctcaaccaccatatcaaccaggccttaaaagctcacgttgcgatg caaaaggacgttgactatgtagtggaagacggacaggttgttattgttga ttccttcacgggacgtctgatgaaaggccgccgctacagtgaggggcttc accaagcgattgaagcaaaggaagggcttgagattcaaacgaaagcatg accttggcgacgattacgttccaaaactacttccgaatgtacgaaaaact tgccggtatgacgggtacagctaagacagaggaagaagaattccgcaaca tctacaacatgcaggttgtcacgatccctaccaacaggcctgttgtccgt gatgaccgcccggatttaatttaccgcacgatggaaggaaagtttaaggc agttgcggaggatgtcgcacagcgttacatgacgggacagcctgttctag tcggtacggttgccgttgaaacatctgaattgatttctaagctgcttaaa aacaaaggaattccgcatcaagtgttaaatgccaaaaaccatgaacgtga agcgcagatcattgaagaggccggccaaaaaggcgcagttacgattgcga ctaacatggcggggcgcggaacggacattaagcttggcgaaggtgtaaaa gagcttggcgggctcgctgtagtcggaacagaacgacatgaatcacgccg gattgacaatcagcttcgaggtcgttccggacgtcagggagacccgggga ttactcaattttatctttctatggaagatgaattgatgcgcagattcgga gctgagcggacaatggcgatgcttgaccgcttcggcatggacgactctac tccaatccaaagcaaaatggtatctcgcgcggttgaatcgtctcaaaaac gcgtcgaaggcaataacttcgattcgcgtaaacagcttctgcaatatgat gatgttctccgccagcagcgtgaggtcatttataagcagcgctttgaagt cattgactctgaaaacctgcgtgaaatcgttgaaaatatgatcaagtctt ctctcgaacgcgcaattgcagcctatacgccaagagaagagcttcctgag gagtggaagcttgacggtctagttgatcttatcaacacaacttatcttga tgaaggtgcacttgagaagagcgatatcttcggcaaagaaccggatgaaa tgcttgagctcattatggatcgcatcatcacaaaatataatgagaaggaa gagcaattcggcaaagagcaaatgcgcgaattcgaaaaagttatcgttct tcgtgccgttgattctaaatggatggatcatattgatgcgatggatcagc tccgccaagggattcaccttcgtgcttacgcgcagacgaacccgcttcgt gagtatcaaatggaaggttttgcgatgtttgagcatatgattgaatcaat tgaggacgaagtcgcaaaatttgtgatgaaagctgagattgaaaacaatc tggagcgtgaagaggttgtacaaggtcaaacaacagctcatcagccgcaa gaaggcgacgataacaaaaaagcaaagaaagcaccggttcgcaaagtggt tgatatcggacgaaatgccccatgccactgcggaagcgggaaaaaatata aaaattgctgcggccgtactgaatag Carbamoyl-phosphate synthase small chain (carA, macromolecular synthesis operon), *B. subtilis* PT26A.

(SEQ ID NO: 24)
atgaagagacgattagtattggaaaacggagcggtattcgagggagaagc cttcggaagcttagaacacaacatgggagaagtcgtttttaatactggga tgacaggctatcaggaaattttatctgacccttcttactgcggacagatc gtaacattaacatacccgcttatcggaaattacggcattaaccgtgatga ttttgaatccattaccccttttgtgaaagggctgatcatcaaagaattat gtgagctgccttccaactggcgttcagcatacaccttagacgagtattta aaaataaaaaacattcccggactccaggggattgatacaaggaagctgac aagaatgatccgcacggcaggcgcgctaaaaggaacattcgcttcatctg atgaagatatcgaagcagtgctgaaaagactgaacgaaacggaattgcca agaaatcaagtatcccaagtatcagccaaaacagcatatccgagcccggg aagaggcaaacgcattgtcttggttgacttcggcacgaaacacgggattc taagagagctgaacaaacggaaatgtgacgtcatcgttgtgcccttacaac attacagcggaagaggtgcttcagctgaaaccggacggtatcatgctttc taacggacctggagacccgaaggatgtgcctgaagcgattgaaatgatta aaggtgttcttggaaaagtgccattattcggaatatgtctcggccaccaa ttattcgcgctggcgtgcggggcgaatactgaaaaaatgaaattcggcca cagggctcaaaccacccggtaaaagagctggctacaggaaaagttgcct taacatctcaaaaccatggatatacagtttcgtctatcagtaaaacagaa ctggaagtgacgcatatcgcaattaacgacgatacgattgaagggctgaa gcataaaacattgccggcatttacggttcaatatcatcccgaagcctcac ctggtcctgaggatgccaaccatctatttgacagattcatcgaaatgatc gaaacaacagagaagaagggggaagcggtatgccaaaacgcgtag RecA protein, *B. subtilis* PT26A.

(SEQ ID NO: 25)
atgagtgatcgtcaggcagccttagatatggctcttaaacaaatagaaaa acagttcggcaaaggttccattatgaaactgggagaaaagacagatacaa gaatttctactgtaccaagcggctccctcgctcttgatacgcactggga attggcggatatcctcgcggacggattattgaagtatacggtcctgaaag ctcaggtaaaacaactgtggcgcttcatgcgattgctgaagttcagcagc agggcggacaagccgcgtttatcgatgcggagcatgcgttagatccggta tacgcgcaaaagctcggtgttaacatcgaagagcttttactgtctcagcc tgacacaggcgagcaggcgcttgaaattgcggaagcattggttcgaagcg gggcagttgacattgtcgttgtcgactctgtagccgctctcgttccgaaa gcggaaattgaaggcgacatgggagattcgcatgtcggtttacaagcacg cttaatgtctcaagcgcttcgtaagctttcaggggccattaacaaatcga agacaatcgcgattttcattaaccaaattcgtgaaaagtcggtgttatg ttcgggaacccggaaacaacacctggcggccgtgcgttgaaattctattc ttccgtgcgtcttgaagtgcgccgtgctgaacagctgaaacaaggcaacg acgtaatggggaacaaaacgaaaatcaaagtcgtgaaaaacaaggtggct ccgccgttccgtacagccgaggttgacattatgtacggagaaggcatttc aaaagaaggcgaaatcattgatctaggaactgaacttgatatcgtgcaaa aaagcggttcatggtactcttatgaagaagagcgtcttggccaaggccgt gaaaatgcaaaacaattcctgaaagaaaataaagatatcatgctgatgat ccaggagcaaattcgcgaacattacggcttggataataacggagtagtgc agcagcaagctgaagagacacaagaagaactcgaatttgaagaataa Heat shock DnaK gene cluster chaperone protein, *B. subtilis* PT26A.

(SEQ ID NO: 26)
gtgagtaaagttatcggaatcgacttaggaacaacaaactcatgtgtggc agtgcttgaaggcggcgagcctaaagttattgctaacgctgaaggaaacc gcacaacgccatcagttgttgcatttaaaaacggcgaacgtcaagtaggg gaagtggctaaacgccaatctattacaaaccctaacacaattatgtctat caaacgtcatatgggtactgattataaagttgaaattgaaggaaaggatt acactccacaagaagtgtctgctatcatccttcaacaccttaaatcatac gctgaaagctatcttggcgaaacagtatcaaaagcagttatcacagttcc agcatactttaacgatgctgagcgtcaagctacaaaagacgctggtaaaa ttgcaggtcttgaagtagaacgtatcatcaacgagccgactgcagcagcg cttgcatacggacttgataaaacagatgaagatcaaacgatcctagtata cgaccttggcggcggtacattcgacgtttccatccttgagcttggcgacg gtgtattcgaagttcgttcaactgccggcgacaaccgtctgggcggggac gattttgaccaagttatcatcgatcatcttgtgtctgaattcaaaaaaga aaacggcattgatttgtcaaaagacaaaatggcgcttcagcgtttgaaag acgcagctgaaaaagcgaaaaagatcttccggcgtatcttctacgcaa atttctttaccgtttatcacagctggagaagcaggaccgcttcaccttga acttacattaacacgcgctaaattcgaagagcttttcttctcattagtag agcgcacaatgggtcctgtccgtcaagcgcttcaagatgcaggactttct gcaagcgaaatcgacaaagtcatccttgtcggcggatcaactcgtatccc tgccgtacaagaagcaatcaaaaaagaaactggaaaagaagcgcataaag gcgtaaacccggatgaagttgtagcgcttggtgctgcgattcagggcggc gttatcacaggtgacgtaaaagatgttgttcttcttgacgttacaccgct ttctctcggtatcgaaacaatgggcggcgtgtttacaaaactgatcgacc gcaacacgacgatcccgacaagcaaatctcaagtgttctcaactgctgct gataaccaaacagctgttgatatccatgttcttcaaggtgagcgcccaat gtctgccgacaacaaaacactcggccgcttccagcttactgatatcccgc cagcaccgcgcggcgtgcctcaaatcgaagtttctttcgatattgacaaa aacggtatcgtaaacgtaagagcaaaagacttaggcacagggaaagaaca aaacattacaatcaaatcttcttcaggtcttttcagatgaagagatcgaac gcatggtaaaagaagcggaagaaaatgctgacgctgatgcgaagaaaaaa gaagaaatcgaagtccgcaacgaagcagatcagcttgttttccaaactga gaaaacattaaaagatcttgaaggcaaagtagacgaagaacaagtgaaaa aagccaacgatgccaaagatgctttaaaagcagcgattgagaaaaacgaa tttgaagagatcaaagcgaaaaagatgagcttcaaacaatcgttcaaga gctttctatgaagctttatgaagaagctgctaaagcacagcaagctcaag gcggagcaaacgctgaaggcaaagcggatgacaacgttgtcgacgctgaa tacgaagaagtaaacgacgaccaaaacaaaaaataa Heat shock protein 60 family chaperone GroEL, *B. subtilis* PT26A.

(SEQ ID NO: 27)
atggcaaaagaaattaagtttagtgaagaagctcgccgcgcaatgcttcg cggtgtcgatgcacttgctgatgctgttaaagtaactttaggaccaaaag gacgcaacgtggttctagagaaaaaattcggttctccgttaatcacaaat gacggtgtaacaatcgctaaagaaatcgagctagaagacgcgtttgaaaa catgggtgctaagcttgttgctgaagtagccagcaaaacaaacgacgttg

```
ccggtgacggtacaacaactgcaacagttcttgcgcaagcaatgatccgt
gaaggccttaaaaacgtaacagcaggcgctaaccctgtaggcgtgcgtaa
agggatggaacaagctgtagcggttgcgatcgaaaacttaaaagaaattt
ctaagccaatcgaaggcaaagagtctatcgctcaggttgctgcgatctct
gctgctgatgaggaagtcggaagccttatcgctgaagcaatggagcgcgt
aggaaacgacggcgttatcacaatcgaagagtctaaaggcttcacaactg
agcttgaagttgttgaaggtatgcaattcgaccgcggatatgcgtctcct
tacatggtaactgactctgataagatggaagcggttcttgacaatcctta
catcttaatcacagacaaaaaaatcacaaacattcaagaaatccttcctg
tgcttgagcaggttgttcagcaaggcaaaccattgcttctgatcgctgag
gatgttgaaggcgaagcacttgctacacttgttgtgaacaaacttcgcgg
cacattcaacgcagttgctgttaaagctcctggcttcggtgaccgccgta
aagcaatgcttgaagacatcgctgtccttactggcggagaagtcatcaca
gaagatcttggccttgacctgaaatctactcaaatcgctcaattgggacg
cgcttctaaagttgtcgttactaaagaaaacacaacaatcgttgaaggcg
ctggcgaaacagacaaaatttctgcccgcgtgactcaaatccgcgctcaa
gtggaagaaacaacttctgaattcgacagagaaaaattacaagagcgtct
tgctaaacttgctggcggcgtagctgtcatcaaagtcggtgctgcgactg
aaaactgaactgaaagagcgtaaacttcgcatcgaagacgccctgaactca
actcgcgcagctgttgaagaaggcatcgtatccggtggtggtacagcgct
tgtaaacgtatataacaaagtcgctgcagttgaagctgaaggcgatgctc
aaacaggtatcaacatcgtgcttcgcgcgcttgaagagccaatccgtcaa
atcgcacacaatgctggtcttgaaggatctgtcatcgttgaacgcctcaa
aaacgaagaaatcggcgtaggcttcaacgctgcaactggcgaatgggtaa
acatgatcgaaaaaggtatcgttgacccaacgaaagttacacgctcagct
cttcaaaacgctgcgtctgtagctgcaatgttcttaacaactgaagccgt
tgtcgctgacaagccagaagaaaacgctggcggcggaatgcctgatatgg
gcggcatgggcggtatgggcggaatgatgtaa
```

ATP synthase beta chain (atpD), *B. subtilis* PT26A.

(SEQ ID NO: 28)
```
atgaagaaaggacgcgttagccaggtattaggaccggtcgtcgacgtgcg
ttttgaagacggtcacttgcctgaaatttataatgcgattaaaatttcac
agccagctgcaagtgaaaacgaagtaggtattgatttaacgcttgaggtc
gctcttcatttaggtgatgatacagtccgtacaatcgcaatggcatctac
ggatggtgttcagcgcggtatggaagctgtagatacaggagcgccaatct
cagtaccggttggtgatgtaacacttggacgtgtatttaacgttctcgga
gaaaatattgatttgaatgagccggttcctgcggatgcgaaaaaggatcc
gattcacagacaggcgcctcattcgatcagctttcaacagaagttgaaa
ttcttgaaacaggtattaaagttgttgatttgcttgctccttacattaag
ggcggtaaaatcggattgttcggtggtgccggtgtaggtaaaaccgtatt
```

```
aatccaggaattaatcaacaacatcgcgcaagagcacggcggtatctctg
tattcgccggcgtaggagagcgtactcgtgaagggaacgacctttctac
gaaatgagtgactctggcgtaatcaacaaaacagccatggtattcggaca
aatgaacgagccgccgggcgcacgtatgcgtgttgctttgacaggcctta
caatggctgagcacttccgtgatgtacaaggacaggacgtactgttcttc
atcgataacatttccgtttcacacaagcgggttcagaggtttcagccct
tcttggccgtatgccttcagcggttggttatcagccgacgcttgcaactg
agatgggtcagctccaagagcgtatcacgtctacgaacgttggatcagtt
acatctatccaggcgatctacgtgcctgccgatgactacactgacccggc
gccggcgacaacgttcgctcacttggatgcgacaacaaaccttgagcgta
aattaactgaaatgggtatttaccctgcggttgatccgttggcatctaca
tcacgcgcccttgctcctgaaattgtcggagaagagcattatgcagttgc
gcgtgaagtacagtcaacgcttcagcgttacaaagagcttcaagatatca
ttgcgattctcggtatggatgaattaggcgaggaagacaaacttgtcgtt
caccgcgcacgccgtatccagttcttcctttctcagaacttccacgtggc
tgaacagttcactggacaaaaaggttcttacgtgcctgtaaaagagacgg
tacaaggcttcaaagaaatcttagccggtaaatacgaccatcttccagaa
gatgcgttccgtcttgtaggccgtatcgaagaagttgttgagaaagcaaa
agaaatgggtgtagaagtttaa
``` gyrB (DNA gyrase subunit B), *B. subtilis* PT26A.

(SEQ ID NO: 29)
```
atggctgataaacaaacccacgagacagaattaacattcgaccaagtaaa
agagcaattaacagagtctggtaaaaaacgtggcgttttgacatatgaag
aaattgctgagcgtatgtccagctttgaaatttgaatcagaccaaatggat
gagtattatgaattttaggtgaacaaggtgttgaattaattagtgagaa
tgaagaaacagaagatcctaatattcagcagcttgccaaagccgaagaag
aatttgaccttaatgacctaagtgtaccgcctggcgttaaaatcaatgac
ccagttcgtatgtatttaaaggaaatcggtcgggttaaccttctttctgc
aaaagaagaaatcgcctacgctcaaaagattgaagaaggtgacgaagaat
ctaaacgcagattggctgaagcgaacctgcggcttgttgtcagtatcgca
aaacggtatgtcggacgcggtatgctgttccttgatctgatccaggaagg
aaacatgggcctgatgaaagccgttgaaaaatttgattatcgcaaaggtt
ataaattcagtacgtatgctacgtggtggatcagacaggcgattacacgc
gccattgccgatcaggcgagaacgatccggattcccgttcatatggttga
aaccattaataaattaatccgtgtgcagcgtcaattactgcaagacttag
gcagagaaccaacacctgaagaaattgcggaagatatggatttaacgcct
gaaaagtacgcgaaatcttaaagattgctcaagagccggtatctctgga
aacaccgatcggtgaagaggatgactcgcaccttggtgatttcattgaag
accaagaagcaacttcaccttctgaccacgccgcatacgagctattgaaa
gagcagctggaagatgtgcttgatacgttaactgatcgtgaagaaaatgt
```

-continued attgcgtcttcgattcggtcttgatgacggccgtacaagaacattagaag aggtcggcaaagtatttggagtaacgagagagcgtattcgacaaatcgaa gccaaagcgttgcggaaactaagacatcctagcagaagtaaacgtttgaa agatttccttgaataa Translation initiation factor 2 (infB), *B. subtilis* PT26A.

(SEQ ID NO: 30)
atggctaaaatgagagtatatgaatatgcaaaagcgttaaatgtttcaag taaggaaattttgaccgcactgaagaacatggatttagaagtgaataatc acatggccatgcttgaagaaaaggccattaaaaagctagatgccaaatat aaaaaaggcggcgcagctgctaaatctcaaaagccagcagatacgaacaa aaacaaaccacaaggggttaatcagcaatcagctggaaatcaaccaa ataaaattcgagacggaaagaagaatgacgtgcagaataatcaatttaac aaaaacaagaagaataacaacaacaaaaaaaataaacgcaacaacaacaa taataaaaaccaacatcagcaaaagcctgtaaagccgaaaaaagagcttc ctgagaaaattacattctctggcacttttaacagttggcgcacttgctgaa gagcttggcaaagagccttcagaaatcattaaaaagctgatgcttcttgg cgtaatggcaaccattaaccaagagcttgataaagacacaatcgaactca ttgcatcagaatatggtgttgaaacagaagaggtcattgtgcttgaagaa acagagctggaaaaatacgaagagcctgataatgaagaggatcttgaaat tcgtcctcctgtcgtgacaatcatgggccacgttgaccatgggaaaacaa cgcttcttgacagcatccgtaaaacaaaggttgttgaaggagaagcaggc ggaatcactcagcatatcggcgcttatcaaattgaagagaacggcaagaa aatcacgttcttggatacaccgggccacgccgcatttacaacaatgcgtg cacgcggtgcagaagtaactgatattacgattcttgtcgtagctgccgat gacggtgtcatgccgcaaacagttgaagcgattaaccatgcaaaagcagc agaggttccaatcatcgttgctgtgaataaaatagataaagaatctgcaa accctgaccgtgtaatgcaagaactgacggaatacggacttgtccctgaa gcttggggcggagaaaccattttttgtgccgctttccgctttaactggaaa aggcattgatgagctcgttgaaatgattttgcttgtcagtgaggtagagg aactgaaagcgaatccgaaccgtcaggcaaaaggaacggttattgaagct gaactcgataaaggcagagggtcagttgcgacgttgctcgtacagactgg aacactgcatgtcggtgatccgatcgtagtcggcaatacatttggccgtg tccgtgcaatggtcaacgacattggccgccgtgtgaaaactgccggcccg tcaactccggttgaaattaccggtttgaatgatgtccctcaagcgggaga ccaattccttgtctttaaggatgaaaaaacagctcgttctgtcggtgaag cccgtgcttcgaaacagcttgaagagcagcgcagcgataaagcgaagctc agtcttgatgatttattcgagcaaattaagcaaggtgatgtaaaagacat caacctcatcgtaaaagctgacgttcaaggatctgctgaagctttaacgg ctgcgcttcaaaaaattgaagtagaaggcgttaaagtgaaaatcatccat acaggcgttggtgcgattactgaatctgacattatcttggcatctgcttc caatgcaattgttatcgggtttaatgtgagaccggacggaaatgctaaga gtacggctgaagctgaaaatgtagatattcgacttcaccgtatcatttac aaagtaatcgacgagattgaagctgccatgaaaggtatgcttgatcctga atatgaagaaaagtaattggtcaagtagaagtacgccaaacattcaaag tatctaaaatcggtacaattgccggcggatatgttactgaaggaaccatt acgcgcgacagcggcctccgtttaattcgtgatggcgtcgtcatctttga aggcgaagtagatgttctgaaacgctttaaagacgatgtgaaagaagttt cacaaggctatgaatgtggtattacaattaagaaatacaatgacattcgt gaaggtgacatcctagaagcgtttgtcatgcaagaaattgaaagaacgtg
a

---

What is claimed is:

1. A seed which is treated or coated with a bacterial composition comprising at least one isolated bacterial strain selected from the group consisting of *Bacillus megayerium* PT6 having accession number PTA-122799 and *Bacillus subtilis* PT26A having accession number PTA-122797.

2. A plant defense inducer composition comprising at least one isolated bacterial strain selected from the group of *Bacillus megaterium* PT6 having accession number PTA-122799 and *Bacillus subtilis* PT26A having accession number PTA-122797, and a plant defense inducer compound selected from the group consisting of β-aminobutyric acid (BABA) or a salt thereof, and salicylic acid (SA) or a salt thereof.

3. A method of improving the health and vigor of a plant, comprising administering to the plant an effective amount of a bacterial composition comprising at least one isolated bacterial strain selected from the group of *Bacillus megaterium* PT6 having accession number PTA-122799 and *Bacillus subtilis* PT26A having accession number PTA-122797,
wherein the improvement in health and vigor is one or more of:
a) improved resistance to disease;
b) improved ability to defend against disease;
c) reduction of disease symptoms;
d) faster growth;
e) improved crop productivity;
f) improved crop quality;
g) improved seed germination; and
h) improved seedling emergence.

4. The method of claim 3, wherein the at least one bacterial strain is *Bacillus subtilis* PT26A having accession number PTA-122797.

5. The method of claim 4, wherein the plant is a crop plant.

6. The method of claim 3, wherein the plant is a citrus plant.

7. The method of claim 6, wherein the citrus is selected from the group consisting of *Citrus maxima* (Pomelo), *Citrus medica* (Citron), *Citrus micrantha* (Papeda), *Citrus reticulata* (Mandarin orange), *Citrus paradisi* (grapefruit), *Citrus trifolata* (trifoliate orange), *Citrus japonica* (kumquat), *Citrus australasica* (Australian Finger Lime), *Citrus australis* (Australian Round lime), *Citrus glauca* (Australian Desert Lime), *Citrus garrawayae* (Mount White Lime), *Citrus gracilis* (Kakadu Lime or Humpty Doo Lime), *Citrus inodora* (Russel River Lime), *Citrus warburgiana* (New Guinea Wild Lime), *Citrus wintersii* (Brown River Finger Lime), *Citrus halimii* (limau kadangsa, limau kedut kera) *Citrus indica* (Indian wild orange), *Citrus macroptera*, *Citrus latipes*, *Citrus x aurantiifolia* (Key lime), *Citrus x aurantium* (Bitter orange), *Citrus x latifolia* (Persian lime), *Citrus x limon* (Lemon), *Citrus x limonia* (Rangpur), *Citrus x sinensis* (Sweet orange), *Citrus x tangerina* (Tangerine), Imperial lemon, tangelo, orangelo, tangor, kinnow, kiyomi, Minneola tangelo, oroblanco, sweet orange, ugli, Buddha's hand, citron, lemon, orange, bergamot orange, bitter orange, blood orange, calamondin, clementine, grapefruit, Meyer lemon, Rangpur, tangerine, and yuzu.

8. The method of claim 4, wherein the crop is selected from the group consisting of almond, apple, banana, cacao, carrot, cassava, chili, citrus, coconut, coffee, corn, cotton, cucumber, grape, legume, lettuce, mango, olive, onion, palm, peach, peanut, potato, rapeseed, rice, rubber, soybean, strawberry, sugar beet, sugar cane, sunflower, sweet potato, tea, tomato, walnut, wheat, and yam.

9. The method of claim 8, wherein the crop is selected from the group consisting of corn, soybean, and tomato.

10. The method of claim 3, wherein the plant is not affected by a plant disease.

11. The method of claim 3, wherein the plant is affected by a plant disease or plant disease symptoms.

12. The method of claim 11, wherein the plant disease is a bacterial disease.

13. The method of claim 11, wherein the plant disease is a fungal disease.

14. The method of claim 11, wherein the plant disease is selected from the group consisting of huanglongbing (HLB) disease, Fusarium, Phytophthora, citrus canker disease, citrus bacterial spot disease, citrus variegated chlorosis, citrus food and root rot, citrus and black spot disease.

15. The method of claim 14, wherein the administering to the plant is by a method selected from the group consisting of soil injection, soil drenching, application to seed, and foliar spraying.

16. The method of claim 14, wherein the administering to the plant provides at least $10^2$ cfu of the isolated bacterial strain per gram of plant root thirty days after administration.

17. The method of claim 14, wherein the administering to the plant provides at least $10^3$ cfu of the isolated bacterial strain per gram of plant root thirty days after administration.

18. A method of improving seed germination of a seed of a plant, the method comprising administering to the seed of the plant a bacterial composition comprising at least one isolated bacterial strain selected from the group consisting of *Bacillus megaterium* PT6 having accession number PTA-122799 and *Bacillus subtilis* PT26A having accession number PTA-122707.

19. A method of enhancing growth of a plant, the method comprising administering to a seed of the plant, prior to planting, a bacterial composition comprising at least one isolated bacterial strain selected from the group consisting of *Bacillus megaterium* PT6 having accession number PTA-122799 and *Bacillus subtilis* PT26A having accession number PTA-122797.

20. A method of treating a plant disease in a plant in need thereof, which comprises administering to the soil within a ten foot radius surrounding the plant a composition according to claim 2.

21. The method of claim 20, wherein the plant is a Citrus plant and the disease is huanglongbing (HLB) disease.

22. The seed of claim 1, wherein the seed comprise $10^3$-$10^{11}$ cfu/mL of the at least one bacterial strain coated thereon.

23. The seed of claim 1 wherein the at least one bacterial strain is *Bacillus megaterium* PT6 having accession number PTA-122799.

24. The seed of claim 1, wherein the at least one bacterial strain is *Bacillus subtilis* PT26A having accession number PTA-122797.

25. The seed claim 1, wherein the seed comprises at least $10^3$ cfu/mL of the at least one bacterial strain coated thereon.

26. The seed of claim 25, wherein the seed comprise at least $10^5$ cfu/mL of the at least one bacterial strain coated thereon.

27. The seed of claim 25, wherein the seed comprise at least $10^7$ cfu/mL of the at least one bacterial strain coated thereon.

28. The method of claim 3, wherein the bacterial composition comprises $10^3$-$10^{11}$ cfu/mL of the at least one bacterial strain.

29. The method of claim 3, wherein the bacterial composition comprises at least $10^3$ cfu/mL of the at least one bacterial strain.

30. The method of claim 29, wherein the bacterial composition comprises at least $10^5$ cfu/mL of the at least one bacterial strain.

31. The method of claim 30, wherein the bacterial composition comprises at least $10^7$ cfu/mL of the at least one bacterial strain.

* * * * *